(12) United States Patent
Freese et al.

(10) Patent No.: US 9,125,951 B2
(45) Date of Patent: Sep. 8, 2015

(54) **COMPOSITIONS AND METHODS FOR PREPARING *STAPHYLOCOCCUS AUREUS* SEROTYPE 5 AND 8 CAPSULAR POLYSACCHARIDE CONJUGATE IMMUNOGENIC COMPOSITIONS**

(75) Inventors: Stephen John Freese, Cornwall-on-Hudson, NY (US); Annaliesa Anderson, Upper Saddle River, NJ (US); Viliam Pavliak, Montebello, NY (US); Kathrin Ute Jansen, Allendale, NJ (US); Ingrid Lea Scully, Cornwall, NY (US); Tracy Dee Scott, Foristell, MO (US); Jasdeep Singh Nanra, Suffern, NY (US); A. Krishna Prasad, Chapel Hill, NC (US); Bruce Arthur Green, New City, NY (US)

(73) Assignee: Wyeth LLC, New York, NY (US)

( * ) Notice: Subject to any disclaimer, the term of this patent is extended or adjusted under 35 U.S.C. 154(b) by 0 days.

(21) Appl. No.: 13/379,291

(22) PCT Filed: Jun. 22, 2010

(86) PCT No.: PCT/US2010/039473
§ 371 (c)(1),
(2), (4) Date: Dec. 19, 2011

(87) PCT Pub. No.: WO2011/041003
PCT Pub. Date: Apr. 7, 2011

(65) Prior Publication Data
US 2012/0276137 A1 Nov. 1, 2012

Related U.S. Application Data

(60) Provisional application No. 61/219,143, filed on Jun. 22, 2009, provisional application No. 61/219,151, filed on Jun. 22, 2009.

(51) Int. Cl.
*A61K 39/00* (2006.01)
*A61K 39/085* (2006.01)
*A61K 39/385* (2006.01)
*A61K 47/48* (2006.01)

(52) U.S. Cl.
CPC ........... *A61K 47/4833* (2013.01); *A61K 39/085* (2013.01); *A61K 2039/55505* (2013.01); *A61K 2039/6037* (2013.01); *A61K 2039/627* (2013.01); *A61K 2039/64* (2013.01)

(58) Field of Classification Search
None
See application file for complete search history.

(56) References Cited

U.S. PATENT DOCUMENTS

| | | |
|---|---|---|
| 4,134,214 A | 1/1979 | Graham et al. |
| 4,673,574 A | 6/1987 | Anderson |
| 4,708,871 A | 11/1987 | Geysen |
| 4,902,506 A | 2/1990 | Anderson et al. |
| 4,912,094 A | 3/1990 | Myers et al. |
| 5,057,540 A | 10/1991 | Kensil et al. |
| 5,078,996 A | 1/1992 | Conlon, III et al. |
| 5,254,339 A | 10/1993 | Morein |
| 5,614,382 A | 3/1997 | Metcalf |
| 5,723,127 A | 3/1998 | Scott et al. |
| 6,027,925 A | 2/2000 | Pollock et al. |
| 6,113,918 A | 9/2000 | Johnson et al. |
| 6,146,902 A | 11/2000 | McMaster |
| 6,149,919 A | 11/2000 | Domenighini et al. |
| 6,165,995 A | 12/2000 | Hilgers |
| 6,207,646 B1 | 3/2001 | Krieg et al. |
| 6,299,884 B1 | 10/2001 | Van Nest et al. |
| 6,596,861 B1 | 7/2003 | Moreau |
| 6,610,310 B2 | 8/2003 | Hilgers |
| 6,703,025 B1 | 3/2004 | Patti et al. |
| 7,115,730 B1 | 10/2006 | Pizza et al. |
| 7,252,828 B2 | 8/2007 | Pier et al. |
| 7,285,281 B2 | 10/2007 | Green et al. |
| 7,291,588 B2 | 11/2007 | Pizza et al. |
| 7,332,174 B2 | 2/2008 | Green et al. |
| 7,361,355 B2 | 4/2008 | Green et al. |
| 7,384,640 B1 | 6/2008 | Holmes et al. |
| 7,537,766 B2 | 5/2009 | Pavliak et al. |
| 7,666,438 B1 | 2/2010 | Patti et al. |
| 8,017,133 B2 | 9/2011 | Patti et al. |
| 2004/0185058 A1 | 9/2004 | Zagury et al. |
| 2007/0087014 A1 | 4/2007 | Pavliak et al. |
| 2007/0141077 A1 | 6/2007 | Pavliak et al. |
| 2008/0286838 A1 | 11/2008 | Yuan et al. |

FOREIGN PATENT DOCUMENTS

| | | |
|---|---|---|
| CA | 2351018 A1 | 9/2003 |
| EP | 0468714 A2 | 1/1992 |

(Continued)

OTHER PUBLICATIONS

Berti et al. Biophys J Jan. 2004; 86(1):3-9.*
McKenney, D., et al., "Broadly Protective Vaccine for *Staphylococcus aureus* Based on an in Vivo-Expressed Antigen", Science, 284(5419):1523-1527 (1999).
McKenney, D., et al., "The ica Locus of *Staphylococcus epidermidis* Encodes Production of the Capsular Polysaccharide/Adhesin", Infection and Immunity, 66(10):4711-4720 (1998).
Moreau, M., et al., "Structure of the type 5 capsular polysaccharide of *Staphylococcus aureus*", Carbohydrate Research, 201:285-297 (1990).

(Continued)

*Primary Examiner* — Oluwatosin Ogunbiyi
(74) *Attorney, Agent, or Firm* — Victoria S. Molenda

(57) ABSTRACT

The present invention relates to immunogenic conjugates comprising *S. aureus* serotype 5 and 8 capsular polysaccharides conjugated to carrier proteins and methods for their preparation and use. Methods for making the immunogenic conjugates of the invention involve covalent conjugation of the capsular polysaccharides with the carrier proteins using conjugation chemistry involving either 1,1-carboyl-di-1,2,4-triazole (CDT) or 3-(2-pyridyldithio)-propionyl hydrazide (PDPH).

27 Claims, 11 Drawing Sheets

(56) References Cited

FOREIGN PATENT DOCUMENTS

| | | |
|---|---|---|
| EP | 1296713 B1 | 9/2003 |
| EP | 1326634 B1 | 4/2006 |
| JP | 4078417 B | 2/2008 |
| WO | 8606635 A1 | 11/1986 |
| WO | 9204915 A1 | 4/1992 |
| WO | 9309811 A1 | 5/1993 |
| WO | 9508348 A1 | 3/1995 |
| WO | 9903871 A1 | 1/1999 |
| WO | 9927109 A2 | 6/1999 |
| WO | 0012131 A1 | 3/2000 |
| WO | 0056357 A2 | 9/2000 |
| WO | 0056359 A2 | 9/2000 |
| WO | 0170685 A2 | 9/2001 |
| WO | 0172337 A1 | 10/2001 |
| WO | 03/080678 A1 | 1/2003 |
| WO | 03061558 A2 | 7/2003 |
| WO | 03086471 A2 | 10/2003 |
| WO | 2004/019992 A1 | 3/2004 |
| WO | 2004043405 A2 | 5/2004 |
| WO | 2004080490 A2 | 9/2004 |
| WO | 2004083251 A2 | 9/2004 |
| WO | 2005033148 A1 | 4/2005 |
| WO | 2005/058940 A2 | 6/2005 |
| WO | 2006032472 A2 | 3/2006 |
| WO | 2006032475 A2 | 3/2006 |
| WO | 2006032500 A2 | 3/2006 |
| WO | 2006065553 A2 | 6/2006 |
| WO | 2007000322 A1 | 1/2007 |
| WO | WO 2007/000322 * | 1/2007 |
| WO | 2007113222 A2 | 10/2007 |
| WO | 2007113223 A2 | 10/2007 |
| WO | WO 2007/113223 * | 10/2007 |
| WO | 2007127668 A2 | 11/2007 |
| WO | WO 2007/113223 * | 11/2007 |
| WO | 2009109550 A1 | 9/2009 |
| WO | 2010151544 A1 | 12/2010 |
| WO | 2011015591 A1 | 2/2011 |
| WO | 2011051917 A1 | 5/2011 |
| WO | 2012085872 A2 | 6/2012 |

OTHER PUBLICATIONS

Nanra, J.S., et al., "Heterogeneous in vivo expression of clumping factor A and capsular polysaccharide by *Staphylococcus aureus*: Implications for vaccine design", Vaccine, 27:3276-3280 (2009).
Nilsson, I.M., et al., "The Role of Staphylococcal Polysaccharide Microcapsule Expression in Septicemia and Septic Arthritis", Infection & Immunity 65(10):4216-4221 (1997).
Opdebeeck, J.P., et al., "The expression of capsule in serum-soft agar by *Staphylococcus aruues* isolated from human clinical sources", J. Med. Microbiol., 20(2):275-278 (1985).
O'Riordan, K., et al., "*Staphylococcus aureus* Capsular Polysaccharides", Clinical Microbiology Reviews, 17 (1):218-234 (2004).
Paoletti, L.C., "Potency of clinical group B streptococcal conjugate vaccines", Vaccine, 19:2118-2126 (2001).
Park, H.M., et al., "Immunogenicity of Alpha-Toxin, Capsular Polysaccharide (CPS) and Recombinant Fibronectin-Binding Protein (r-FnBP) of *Staphylococcus aureus* in Rabbit", J. of Vet. Med. Sci., 61(9):995-1000 (1999).
Reeves, P.R., et al., "Bacterial polysaccharide synthesis and gene nomenclature", Trends in Microbiology, 4 (12):495-503 (1996).
Reynaud-Rondier, L., et al., "Conjugation of capsular polysaccharide to α-haemolysin from *Staphylococcus aureus* as a glycoprotein antigen", FEMS Microbiol. Immunol., 76:193-199 (1991).
Risley, A.L., "Capsular Polysaccharide Masks Clumping Factor A-Mediated Adherence of *Staphylococus aureus* to Fibrinogen and Platelets", Journal of Infectious Diseases, 196:919-927 (2007).
Romero-Steiner, S., et al., "Standardization of an opsonophagocytic assay for the measurement of functional antibody activity against *Streptococcus pneumoniae* using differentiated HL-60 cells", Clin. Diagn. Lab. Immunol., 4 (4):415-422 (1997).

Sau, S., et al., "The *Staphylococcus aureus* allelic genetic loci for serotype 5 and 8 capsule expression contain the type-specific genes flanked by common genes", Microbiology, 143:2395-2405 (1997).
Schaffer, A.C., et al., "Vaccination and passive immunisation against *Staphylococcus aureus*", International Journal of Antimicrobial Agents, 32(1):S71-S78 (2008).
Schneerson, R., et al., "Evaluation of Monophosphoryl Lipid A (MPL) as an Adjuvant. Enhancement of the Serum Antibody Response in Mice to Polysaccharide-Protein Conjugates by Concurrent Injection with MPL", The Journal of Immunology, 147(7):2136-2140 (1991).
Shinefield, H., et al., "Use of a *Staphylococcus aureus* conjugate vaccine in patients receiving Hemodialysis", New England Journal of Medicine, 346(7):491-496 (2002).
Sompolinsky, D., et al., "Encapsulation and Capsular Types in Isolates of *Staphylococcus aureus* from Different Sources and Relationship to Phage Types", Journal of Clinical Microbiology, 22(5):828-834 (1985).
Suhrbier, A., "Multi-epitope DNA vaccines", Immunol. Cell Biol., 75(4):402-408 (1997).
Tanizaki, M.M., et al., "Purification of meningococcal group C polysaccharide by a procedure suitable for scale-up", J. Microbiol. Methods, 27(1):19-23 (1996).
Thakker, M., et al., "*Staphylococcus aureus* Serotype 5 Capsular Polysaccharide is Antiphagocytic and Enhances Bacterial Virulence in a Murine Bacteremia Model", Infection and Immunity, 66(11):5183-5189 (1998).
Tollersrud, T., "*Staphylococcus aureus* capsular polysaccharide type 5 conjugate and whole cell vaccines stimulate antibody responses in cattle", Vaccine, 19(28-29):3896-3903 (2001).
Tzianabos, A.O., et al., "Structural rationale for the modulation of abscess formation by *Staphylococcus aureus* capsular polysaccharides", Proceedings from the National Academy of Sciences, 98(16):9365-9370 (2001).
Vann, W.F., et al., "Structure and immunochemistry of *Staphylococcus aureus* capsular polysaccharide", UCLA Symp. Mol. Cell. Biol. New. Ser., 64:187-198 (1987).
Verheul, A.F.M., et al., "Preparation, Characterization, and Immunogenicity of Meningococcal Immunotype L2 and L3,7,9 Phosphoethanolamine Group-Containing Oligosaccharide-Protein Conjugates", Infection and Immunity, 59 (3):843-851 (1991).
Vernachio, J.H., et al., "Human Immunoglobulin G Recognizing Fibrinogen-Binding Surface Proteins is Protective against both *Staphylococcus aureus* and *Staphylococcus epidermidis* Infections in Vivo", Antimicrobial Agents and Chemotherapy, 50(2):511-518 (2006).
Wang, X, et al., "The pgaABCD Locus of *Escherichia coli* Promotes the Synthesis of a Polysaccharide Adhesin Required for Biofilm Formation", Journal of Bacteriology, 186(9):2724-2734 (2004).
Watts, A., et al., "*Staphylococcus aureus* strains that express serotype 5 or serotype 8 capsular polysaccharides differ in virulence", Infection and Immunity 73(6):3502-3511 (2005).
Welch, P.G., et al., "Safety and Immunogenicity of *Staphylococcus aureus* Type 5 Capsular Polysaccharide-*Pseudomonas aeruginosa* Recombinant Exoprotein a Conjugate Vaccine in Patients on Hemodialysis", Journal of the American Society of Nephrology, 7(2):247-253 (1996).
Pavliak, V., "*Staphylococcus aureus* capsular polysaccaride-MSCRAMM protein conjugate vaccines", 232nd ACS National Meeting, San Francisco, CA (Sep. 10-14, 2006) (Abstract).
Arbeit, R.D., et al., "Predominance of two newly described capsular polysaccharide types among clinical isolates of *Staphylococcus aureus*", Diagn. Microbiol. Infect. Dis., 2(2):85-91 (1984).
Bergmann, C., et al., "An endogenously synthesized decamer peptide efficiently primes cytotoxic T cells specific for the HIV-1 envelope glycoprotein", Eur. J. Immunol., 23(11):2777-2781 (1993).
Bergmann, C.C., et al., "Flanking residues alter antigenicity and immunogenicity of multi-unit CTL epitopes", J. Immunol., 157(8):3242-3249 (1996).
Bhasin, N., et al., "Identification of a gene essential for O-acetylation of the *Staphylococcus aureus* type 5 capsular polysaccharide", Molecular Microbiology, 27(1):9-21 (1998).
Chen, H.L., "Research development on the immunomodulatory effect of polysaccharide and its mechanism", Chinese Pharmacological Bulletin, 18(3): 249-252 (2002) (English Abstract).

(56) References Cited

OTHER PUBLICATIONS

Cocchiaro, J.L., et al., "Molecular characterization of the capsule locus from non-typeable *Staphylococcus aureus*", Mol. Microbiol., 59(3):948-960 (2006).

Collier, R.J., "Diphtheria Toxin: Mode of Action and Structure", Bacterological Reviews, 39(1):54-85 (1975).

Doe, B., et al., "Induction of HIV-1 envelope (gp120)-specific cytotoxic T lymphocyte responses in mice by recombinant CHO cell-derived gp120 is enhanced by enzymatic removal of N-linked glycans", Eur. J. Immunol., 24.(10):2369-2376 (1994).

Dunne, W.M., "Bacterial Adhesion: Seen Any Good Biofilms Lately?", Clin. Microbiol. Rev., 15(2);155-166 (2002).

Erickson, A.L., et al., "Hepatitis C virus-specific CTL responses in the liver of chimpanzees with acute and chronic hepatitis C", J. Immunol., 151(8):4189-4199 (1993).

Farres, J., et al., "A simple and efficient method for the purification of an exopolysaccharide from *Klebsiella* sp. I-714", Biotechnol. Tech., 10(5):375-380 (1996).

Fattom, A. et al., "Effect of conjugation methodology, carrier protein, and adjuvants on the immune response to *Staphylococcus aureus* capsular polysaccharides", Vaccine, 13(14):1288-1293 (1995).

Fattom, A., et al., "Synthesis and immunologic properties in mice of vaccines composed of *Staphylococcus aureus* type 5 and type 8 capsular polysaccharides conjugated to *Pseudomonas aeruginosa* exotoxin A", Infection and Immunity, 58(7):2367-2374 (1990).

Fattom, A., et al., "Comparative immunogenicity of conjugates composed of the *Staphylococcus aureus* type 8 capsular polysaccharide bound to carrier proteins by adipic acid dihydrazide or N-succinimidyl-3-(2-pyridyldithio) propionate", Infection and Immunity, 60(2):584-589 (1992).

Fattom, A., et al., "Epitopic overload at the site of injection may result in suppression of the immune response to combined capsular polysaccharide conjugate vaccines", Vaccine, 17(2):126-133 (1999).

Fattom, A., et al.,"Laboratory and clinical evaluation of conjugate vaccines composed of *Staphylococcus aureus* type 5 and type 8 capsular polysaccharides bound to *Pseudomonas aeruginosa* recombinant exoprotein A", Infection and Immunity, 61(3):1023-1032 (1993).

Fattom, A., et al., "Safety and immunogenicity of a booster dose of *Staphylococcus aureus* types 5 and 8 capsular polysaccharide conjugate vaccine (StaphVAX®) in hemodialysis patients", Vaccine 23:656-663 (2004).

Fattom, A.I., et al., "A *Staphylococcus aureus* capsular polysaccharide (CP) vaccine and CP-specific antibodies protect mice against bacterial challenge", Infection and Immunity, 64(5):1659-1665 (1996).

Fattom, A.I., et al., "Antigenic Determinants of *Staphylococcus aureus* Type 5 and Type 8 Capsular Polysaccharide Vaccines", Infection and Immunity, 66(10):4588-4592 (1998).

Fattom, A.I., et al., "Development of StaphVAX™, a polysaccharide conjugate vaccine against *S. aureus* infection: from the lab bench to phase III clinical trials", Vaccine, 22(7):880-887 (2004).

Fattom, A.I., et al., "Staphylococcal Vaccines: a Realistic Dream", Annals of Medicine, 28(1):43-46 (1996).

Fattom, A.I., et al., "*Staphylococcus aureus* vaccination for dialysis patients—an update", Advances in Renal Replacement Therapy, 3(4):302-308, (1996).

Fey, P.D., et al., "Characterization of the relationship between polysaccharide intercellular adhesin and hemagglutination in *Staphylococcus epidermidis*", Journal of Infectious Diseases, 179(6):1561-1564 (1999).

Fournier, J.M., et al., "Isolation of Type 5 Capsular Polysaccharide from *Staphylococcus aureus*", Ann. Inst. Pasteur/Microbiol., 138:561-567 (1987).

Fournier, J.M., et al., "Purification and characterization of *Staphylococcus aureus* type 8 capsular polysaccharide", Infection and Immunity, 45(1):87-93 (1984).

Garcia-Lara, J., et al., "Anti-*Staphylococcus aureus* immunotherapy: current status and prospects", Current Opinion in Pharmacology, 9:552-557 (2009).

Miller, M.D., et al., "Poster Session 41214:HIV-1 expressing the 3TC-associated M184V mutation in Reverse Transcriptase (RT) shows increased sensitivity to Adefovir and PMPA as well as decreased replication capacity in vitro", 12th World AIDS Conference, Geneva, Switzerland (Jun. 28 to Jul. 3, 1998).

Geysen, H.M., et al., "A priori delineation of a peptide which mimics a discontinuous antigenic determinant", Molec. Immunol., 23(7):709-715 (1986).

Geysen, H.M., et al., "Use of peptide synthesis to probe viral antigens for epitopes to a resolution of a single amino acid", Proc. Natl. Acad. Sci. USA, 81(13):3998-4002 (1984).

Gilbert, F.B., et al., "Immunogenicity in cows of *Staphylococcus aureus* type 5 capsular polysaccharide-ovalbumin conjugate", Vaccine, 12(4):369-374 (1994).

Goncalves, V.M., et al., "Simple and efficient method of bacterial polysaccharides purification for vaccines production using hydrolytic enzymes and tangential flow ultrafiltration", Communicating Current Research and Educational Topics and Trends in Applied Microbiology, A. Mendez-Vilas, ed., (Formatex), vol. 1, pp. 450-457 (2007).

Havaei, S.A., et al., "The capsular turnover product of *Staphylococcus aureus* strain Smith", FEMS Microbiology Letters, 118(1-2):37-44 (1994).

Hestrin, S. "The Reaction of Acetylcholine and Other Carboxylic Acid Derivatives with Hydroxylamine, and its Analytical Application", J. Biol. Chem., 180:249-261 (1949).

Jones, C., "Revised structures for the capsular polysaccharides from *Staphylococcus aureus* Types 5 and 8, components of novel glycoconjugate vaccines", Carbohydrate Research, 340(6):1097-1106 (2005).

Jones, C., et al., "Use and validation of NMR assays for the identity and O-Acetyl content of capsular polysaccharides from *Neisseria meningitidis* used in vaccine manufacture", Journal of Pharmaceutical and Biomedical Analysis, 30:1233-1247 (2002).

Jones, T., "Staff VAX Nabi", Current Opinion in Investigational Drugs, 3(1):48-50 (2002).

Karakawa, W.W., "The Role of Capsular Antigens in *Staphylococcus aureus* Immunity", Zentralblatt fur Bakteriologie, 277(4):415-418 (1992).

Karakawa, W.W., et al., "Capsular Antibodies Induce Type-Specific Phagocytosis of Capsulated *Staphylococcus aureus* by Human Polymorphonuclear Leukocytes", Infection and Immunity, 56(5):1090-1095 (1988).

Karakawa, W.W., et al., "Chapter 40: Capsular Polysaccharides of *Staphylococcus aureus*", Seminars in infectious disease, vol. IV: Bacterial Vaccines, L. Weinstein and B.N. Fields, eds., (Thieme—Stratton, New York), pp. 285-293 (1982).

Karakawa, W.W., et al., "Method for the Serological Typing of the Capsular Polysaccharides of *Staphylococcus aureus*", J. Clin. Microbiol. 22(3):445-447 (1985).

Klevens, R.M., et al., "Invasive Methicillin-Resistant *Staphylococcus aureus* Infections in the United States", JAMA, 298(15):1763-1771 (2007).

Lee, C.J., et al., "Protective Immunity of Pneumococcal Glycoconjugates", Crit. Rev. Microbiol., 29(4):333-349 (2003).

Lee, C.J., et al., "Chapter 28: Vaccine-Based Strategies for Prevention of Staphylococcal Diseases", The Staphylococci in Human Disease, K.B. Crossley and G.L. Archer, eds., (Churchill Livingston, New York), pp. 631-654 (1997).

Lee, J.C., "The prospects for developing a vaccine against *Staphylococcus aureus*", Trends in Microbiology, 4 (4):162-166 (1996).

Lee, J.C., et al., "Protective efficacy of antibodies to the *Staphylococcus aureus* type 5 capsular polysaccharide in a modified model of endocarditis in rats", Infection and Immunity, 65(10):4146-4151 (1997).

Lee, J.C., et al., "Purified capsular polysaccharide-induced immunity to *Staphylococcus aureus* infection", J. Infect. Dis., 157(4):723-730 (1988).

(56) References Cited

OTHER PUBLICATIONS

Lemercinier, X., et al., "Full 1H NMR assignment and detailed O-acetylation patterns of capsular polysaccharides from *Neisseria meningitidis* used in vaccine producction", Carbohydrate Research, 296:83-96 (1996).

Mack, D., et al., "The Intercellular Adhesin Involved in Biofilm Accumulation of *Staphylococcus epidermidis* is a Linear β-1,6-Linked Glucosaminoglycan: Purification and Structural Analysis", Journal of Bacteriology, 178(1):175-183 (1996).

Maira-Litran, T., et al., "Comparative Opsonic and Protective Activities of *Staphylococcus aureus* Conjugate Vaccines Containing Native or Deacetylated Staphylococcal Poly-N-Acetyl-β-(1-6)-Glucosamine", Infection and Immunity, 73(10):6752-6762 (2005).

Maira-Litran, T., et al., "Immunochemical Properties of the Staphylococcal Poly-N-Acetylglucosamine Surface Polysaccharide", Infection and Immunity, 70(8):4433-4440 (2002).

Gilbert, F.B., et al., "Purification of type 5 capsular polysaccharide from *Staphylococcus aureus* by a simple efficient method", Journal of Microbiological Methods, 20:39-46 (1994).

Ho, M.M., et al., "Preclinical Laboratory Evaluation of a Bivalent *Staphylococcus aureus* Saccharide-Exotoxin a Protein Conjugate Vaccine", Human Vaccines, 2(3):89-98 (2006).

Imabori, K., et al., "Seikagaku Jiten (Biochemistry Encyclopedia)", 3rd edition (Tokyo-kagakudoujin K.K., Tokyo, Japan), pp. 490 & 1419 (1998).

Nishioka, K., et al., "Yakunitatsu Meneki Jikkenhou (Useful Immunological Experimental Protocols)", (Kodansha K. K., Tokyo, Japan), pp. 7-17 (1985).

Molecularinfo.com, "Protein Purification by Gel Filtration Chromatography", Available at http://www.molecularinfo.com/MTM/G/G3/G3-1/G3-1-1.html, Last accessed on Jan. 27, 2014.

* cited by examiner

[-3)-β-D-ManNAcA(4-O-Ac)-(1-3)-α-L-FucNAc-(1-3)-α-D-FucNAc-(1-]$_n$

FIGURE 2
A.
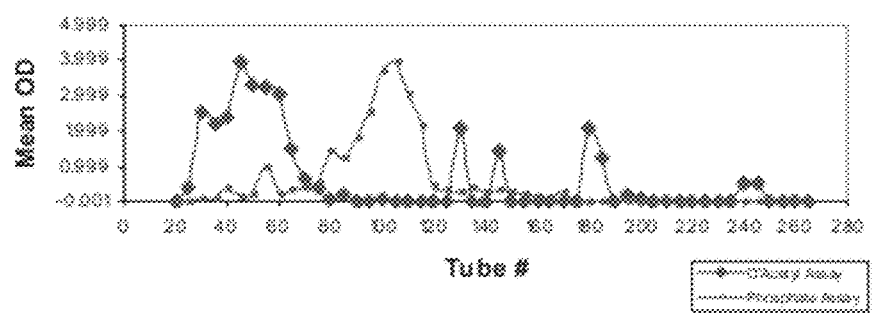
B.
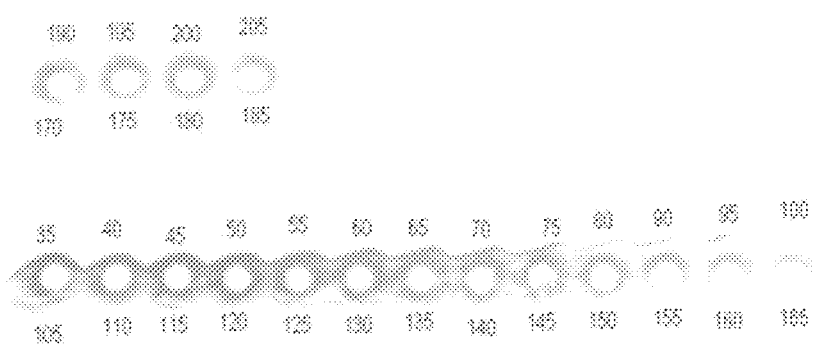

FIGURE 3
A.
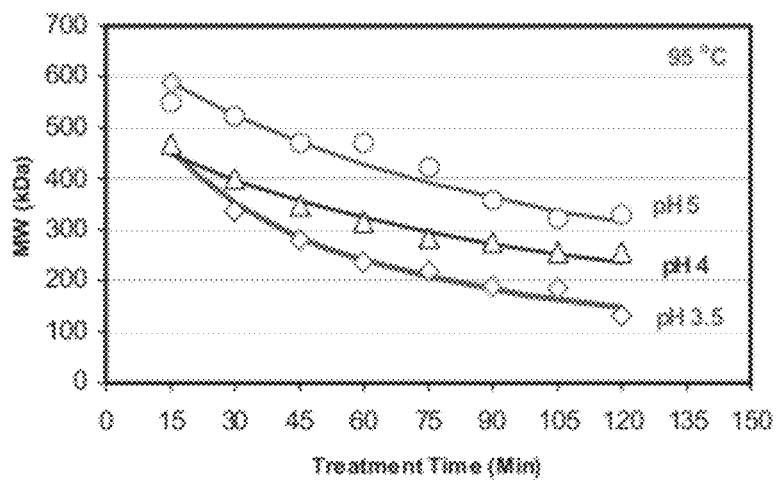
B.
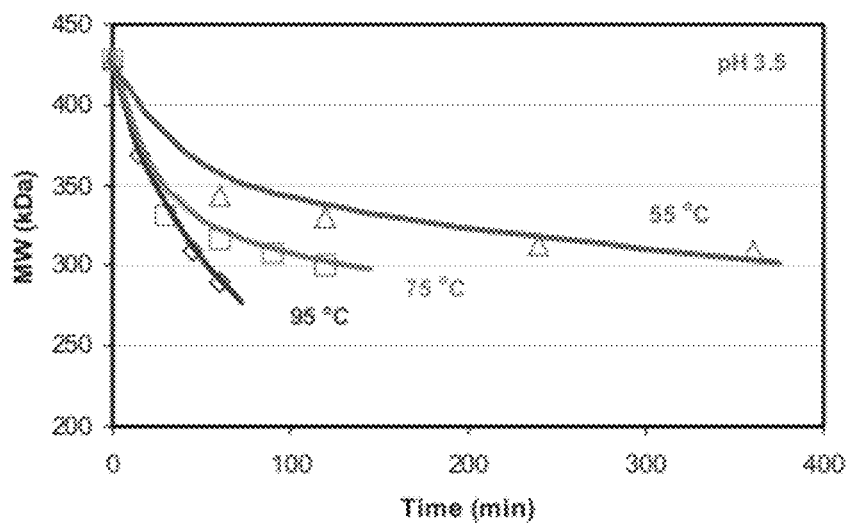

{-4)-β-D-ManNAcA-(1-4)-α-L-FucNAc(3-O-Ac)-(1-3)-β-D-FucNAc-(1-}ₙ

FIGURE 7
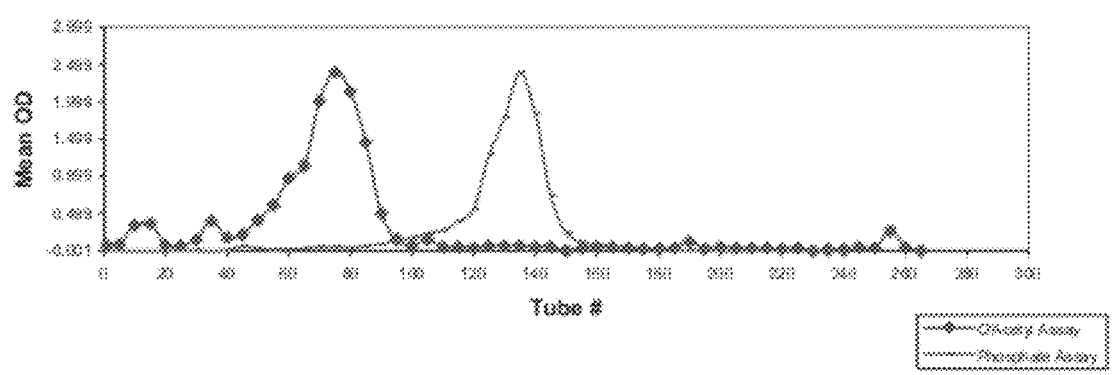
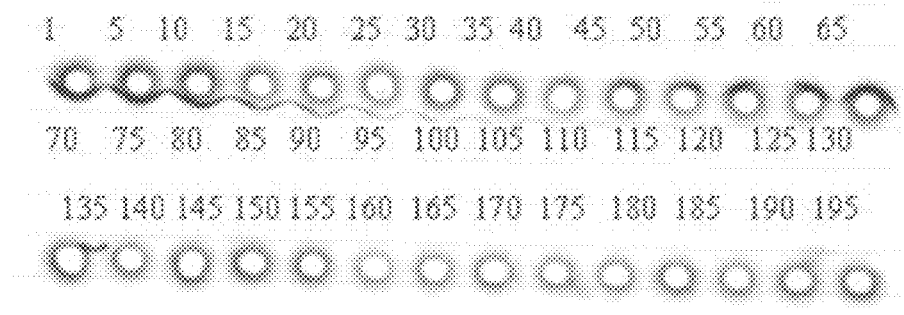

FIGURE 8
A.
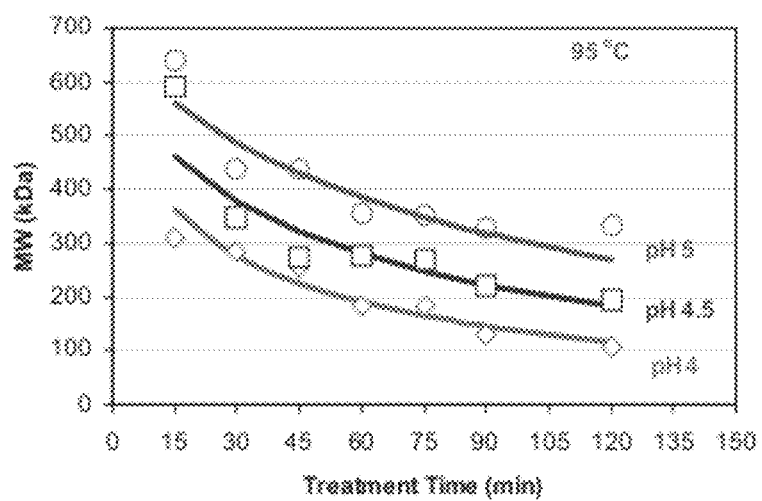
B.
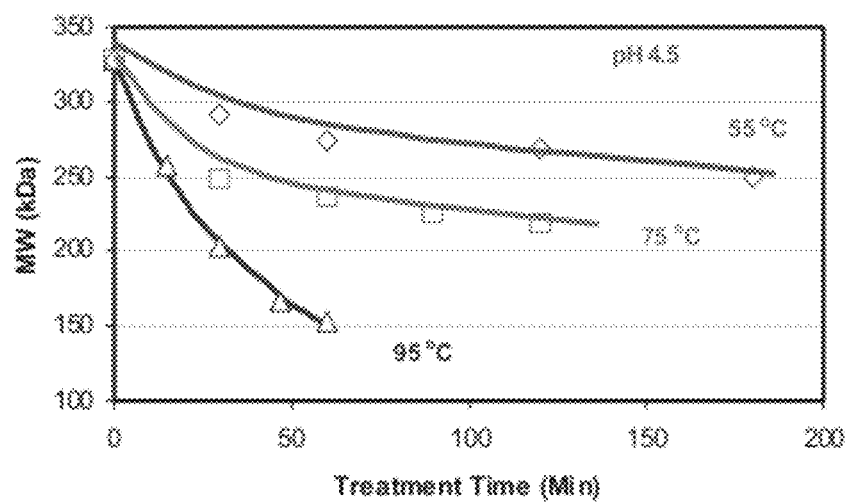

FIGURE 10
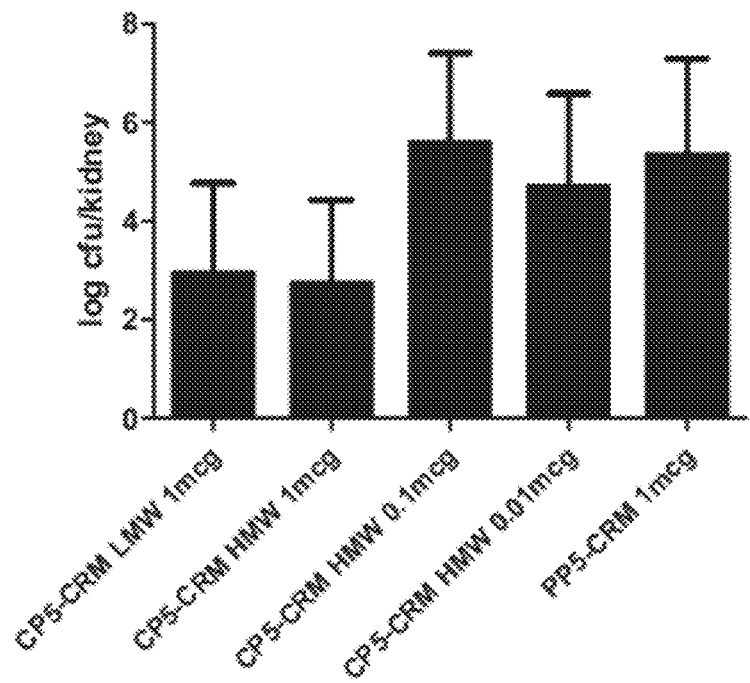
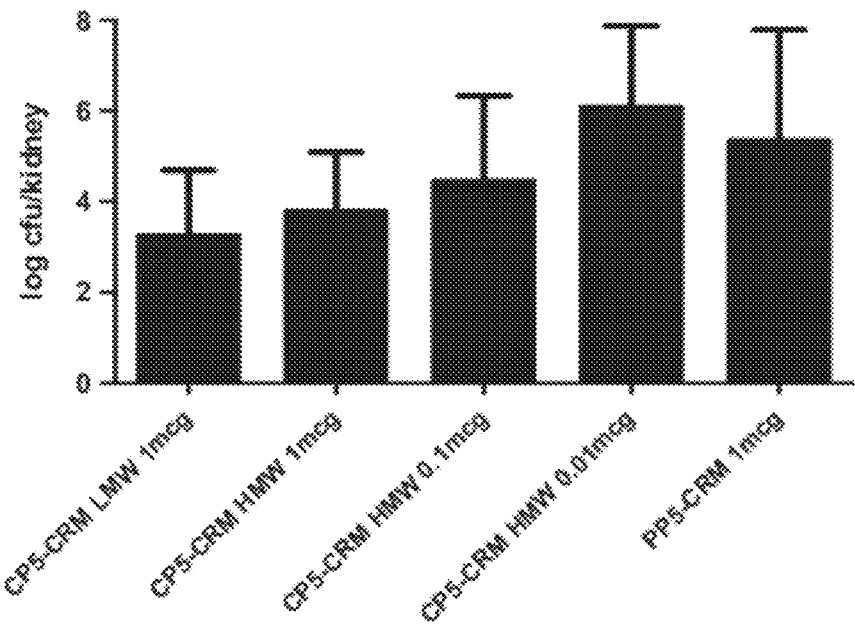

COMPOSITIONS AND METHODS FOR PREPARING *STAPHYLOCOCCUS AUREUS* SEROTYPE 5 AND 8 CAPSULAR POLYSACCHARIDE CONJUGATE IMMUNOGENIC COMPOSITIONS

CROSS REFERENCE TO RELATED APPLICATIONS

This application claims the priority benefit of U.S. Provisional Patent Application Nos. 61/219,143 and 61/219,151, filed Jun. 22, 2009, the entire disclosures of which are each hereby incorporated by reference herein in their entirety.

FIELD OF THE INVENTION

The invention relates generally to *Staphylococcus aureus* serotype 5 and 8 capsular polysaccharide conjugate immunogenic compositions and methods for their preparation and use.

BACKGROUND OF THE INVENTION

Humans are a natural reservoir for Gram-positive *Staphylococcus aureus*. For example, *S. aureus* can colonize the skin, nares and throat, either permanently or transiently, without causing disease. *S. aureus* infections range from mild skin infections to endocarditis, osteomyelitis, bacteremia and sepsis. *S. aureus* also causes a majority of nosocomial infections, and its prevalence in community-onset infections is increasing. Moreover, in 2005, methicillin-resistant *S. aureus* (MRSA) infections were estimated at 31.8 per 100,000 individuals, including 16,650 deaths in the United States in 2005 (Klevens et al. (2007) *J. Am. Med. Assoc.* 298:1763-1771). Disease subsequently occurs when individuals become immunocompromised due to breaches in immune barriers, such as during surgery, placement of indwelling catheters or other devices, trauma or wounds.

*S. aureus* produces a large number of extra- and intracellular antigens, including numerous toxins and enzymes. Of particular interest herein are capsular polysaccharide serotypes of *S. aureus* (see, Karakawa & Vann, "Capsular polysaccharides of *Staphylococcus aureus*," In: Weinstein & Fields, eds. Seminars in Infectious Disease. IV. Bacterial Vaccines. (New York, N.Y.; Thieme Stratton; 1982. pp. 285-293), especially serotype 5 and 8 capsular polysaccharides. Epidemiological studies on a large number of strains of *S. aureus* isolated from individuals showed that 70% to 80% were either serotype 5 or 8 capsular polysaccharide (Arbeit et al. (1984) *Diagn. Microbial. Infect. Dis.* 2:85-91). Unfortunately, the capsular polysaccharides are poor immunogens by themselves.

Staphylococcal infections and diseases dramatically increased in the last twenty years, as has use of intravascular devices and invasive procedures. The rise in disease incidence is more troubling because of a parallel rise of antibiotic resistance; therefore, there is an urgent need for immunogenic compositions to prevent Staphylococcal infections and diseases.

SUMMARY OF THE INVENTION

The present invention is directed towards immunogenic conjugates comprising a *S. aureus* serotype 5 or 8 capsular polysaccharide conjugated to a caner protein, and methods for making such conjugates. *S. aureus* serotype 5 or 8 capsular polysaccharides may be obtained directly from the bacteria using isolation procedures known to those skilled in the art, may be produced using synthetic protocols, or may be recombinantly produced using genetic engineering procedures also known to those skilled in the art. In addition, the present invention provides methods for inducing an immune response against a *Staphylococcus bacterium*, methods for preventing a disease caused by a *Staphylococcus bacterium*, and methods for reducing the severity of at least one symptom of a disease caused by infection with a *Staphylococcus bacterium*.

In one embodiment, the invention comprises an immunogenic polysaccharide-protein conjugate comprising an isolated *Staphylococcus aureus* serotype 5 or 8 capsular polysaccharide conjugated to a carrier protein, wherein the polysaccharide has a molecular weight of between 20 kDa and 1000 kDa. In some embodiments, the immunogenic conjugate has a molecular weight of between 200 kDa and 5000 kDa. In one embodiment the polysaccharide portion of the immunogenic conjugate has a molecular weight range of between 70 kDa and 300 kDa. In one embodiment the immunogenic conjugate has a molecular weight range of between 500 kDa and 2500 kDa.

In one embodiment, the serotype 5 or 8 capsular polysaccharide has a degree of O-acetylation between 10-100%. In one embodiment, the degree of O-acetylation is between 50-100%. In one embodiment, the degree of O-acetylation is between 75-100%. In one embodiment, the immunogenic conjugate generates an antibody that is functional as measured by killing bacteria in either an animal efficacy model or via an opsonophagocytic killing assay.

In one embodiment, the immunogenic conjugate carrier protein comprises $CRM_{197}$. In one embodiment, the $CRM_{197}$ is covalently linked to the polysaccharide through a carbamate linkage, an amide linkage, or both, in one embodiment, the molar ratio of conjugated lysines to $CRM_{197}$ can be about 10:1 to about 25:1. In one embodiment, the conjugate comprises one covalent linkage between $CRM_{197}$ and polysaccharide for at least every 5 to 10 saccharide repeat units of the polysaccharide. In one embodiment, the linkage between carrier protein and polysaccharide occurs for once in every 5 repeat units of the polysaccharide.

In one embodiment, the immunogenic conjugate comprising $CRM_{197}$ comprises 5 to 22 lysines or 8 to 15 lysines covalently linked to the polysaccharide. In one embodiment, the immunogenic conjugate comprising $CRM_{197}$ comprises 5 to 23 lysines or 8 to 12 lysines covalently linked to the polysaccharide.

In one embodiment, the immunogenic conjugate comprises a type 5 or 8 polysaccharide that is 10-100% O-Acetylated. In one embodiment, the immunogenic conjugate comprises a type 5 or 8 polysaccharide that is 50-100% Acetylated. In one embodiment, the immunogenic conjugate comprises a type 5 or 8 polysaccharide that is 75-100% O-Acetylated. In some embodiments, the immunogenic composition can be used to generate antibodies that are functional in an animal efficacy model or an opsonophagocytic assay.

In one embodiment, the immunogenic conjugate comprises less than about 30% free type 5 or 8 polysaccharide compared to the total amount of type 5 or 8 polysaccharide.

In one embodiment, the immunogenic conjugate comprises less than about 20% free type 5 or 8 polysaccharide compared to the total amount of type 5 or 8 polysaccharide.

In one embodiment, the invention comprises an immunogenic composition comprising an immunogenic conjugate as described herein and at least one of an adjuvant, diluent, or carrier.

The adjuvant can be an aluminum-based adjuvant, such as one or more of aluminum phosphate, aluminum sulfate and aluminum hydroxide, in one embodiment the adjuvant comprises aluminum phosphate.

In one embodiment, the immunogenic composition comprises less than about 30% free type 5 or 8 polysaccharide compared to the total amount of type 5 or 8 polysaccharide.

In one embodiment, the immunogenic composition comprises less than about 20% free type 5 or 8 polysaccharide compared to the total amount of type 5 or 8 polysaccharide.

In one embodiment, the invention comprises a method of inducing an immune response to a *Staphylococcus aureus* serotype 5 or 8 capsular polysaccharide conjugate in a subject, comprising administering to the subject an immunologically effective amount of an immunogenic composition as described herein.

In one embodiment, the invention comprises a method of producing an immunogenic polysaccharide-protein conjugate comprising an isolated *Staphylococcus aureus* serotype 5 or 8 capsular polysaccharide conjugated to a carrier protein, the method comprising the steps of: reacting an isolated *S. aureus* serotype 5 or 8 capsular polysaccharide with 1,1-carbonyl-di-(1,2,4-triazole) (CDT) in an organic solvent to produce an activated serotype 5 or 8 polysaccharide; and reacting the activated serotype 5 or 8 polysaccharide with a carrier protein in an organic solvent to produce a serotype 5 or 8 polysaccharide: carrier protein conjugate.

In one embodiment, the method of activating *Staphylococcus aureus* serotype 5 or 8 capsular polysaccharide further comprises lyophilizing the isolated serotype 5 or 8 polysaccharide and re-suspending the lyophilized polysaccharide in an organic solvent. In one embodiment, the resuspended polysaccharide is activated and then directly reacted with the carrier protein. In one embodiment, the activated isolated serotype 5 or 8 polysaccharide is isolated prior to reacting with the carrier protein. In one embodiment, the isolated activated isolated serotype 5 or 8 polysaccharide is lyophilized to produce a lyophilized activated isolated serotype 5 or 8 polysaccharide prior to reacting the polysaccharide with carrier protein. In one embodiment, the method of producing an isolated polysaccharide-carrier protein conjugate comprises a step of lyophilizing the carrier protein to produce a lyophilized carrier protein prior to reacting the carrier protein with the polysaccharide. In one embodiment the method of producing an isolated polysaccharide-carrier protein conjugate comprises the step of re-suspending lyophilized activated isolated serotype 5 or 8 polysaccharide and lyophilized carrier protein in an organic solvent as part of the reaction of the activated isolated serotype 5 or 8 polysaccharide with a carrier protein.

In one embodiment the method of producing an isolated *S. aureus* type 5 or 8 capsular polysaccharide-carrier protein conjugate comprises the step of diluting the reaction mixture of activated polysaccharide and carrier protein and maintaining a pH of about 8.8 to about 9.2 for at least 4 hours at about 20° C. to about 26° C.

In one embodiment, the reaction mixture of activated *S. aureus* type 5 or 8 capsular polysaccharide and carrier protein is maintained at a pH of about 9.0 for at least 4 hours at about 23° C.

In one embodiment the method of producing an isolated *S. aureus* type 5 or 8 capsular polysaccharide-carrier protein comprises the step of isolating the isolated serotype 5 or 8 polysaccharide-protein conjugate after it is produced.

In one embodiment, the organic solvent used in the method of producing an isolated *S. aureus* type 5 or 8 capsular polysaccharide-carrier protein conjugate is a polar aprotic solvent. In one embodiment, the polar aprotic solvent is selected from the group consisting of dimethyl sulfoxide (DMSO), In one embodiment, the method of producing an isolated polysaccharide-carrier protein conjugate the organic solvent is DMSO.

In one embodiment, the method of producing isolated *S. aureus* type 5 capsular polysaccharide-carrier protein conjugate comprises the step of adjusting the water concentration of the reaction mixture comprising type 5 capsular polysaccharide and CDT in an organic solvent to between about 0.1 and 0.3%. In one embodiment, the water concentration of the reaction mixture comprising type 5 capsular polysaccharide and CDT in an organic solvent is adjusted to about 0.2%.

In one embodiment, the step of activating isolated *S. aureus* type 5 capsular polysaccharide comprises reacting the polysaccharide with about an amount of CDT that is 20 molar excess to the amount of polysaccharide present in the reaction mixture comprising type 5 capsular polysaccharide and CDT in an organic solvent.

In one embodiment, the method of producing isolated *S. aureus* type 8 capsular polysaccharide:carrier protein conjugate comprises the step of determining the water concentration of the reaction mixture comprising type 8 capsular polysaccharide. In one embodiment, the amount of CDT added to the reaction mixture to activate the polysaccharide is provided in about an amount of CDT that is equimolar to the amount of water present in the reaction mixture comprising type 8 capsular polysaccharide and CDT in an organic solvent.

In one embodiment, the amount of CDT added to the reaction mixture to activate the polysaccharide is provided in about an amount of CDT that is at a molar ratio of about 0.5:1 compared to the amount of water present in the reaction mixture comprising type 8 capsular polysaccharide and CDT in an organic solvent. In one embodiment, the amount of CDT added to the reaction mixture to activate the polysaccharide is provided in about an amount of CDT that is at a molar ratio of 0.75:1 compared to the amount of water present in the reaction mixture comprising type 8 capsular polysaccharide and CDT in an organic solvent.

In one embodiment, the method which comprises the step of isolating the activated polysaccharide comprises the step of diafiltration.

In one embodiment, the method which comprises lyophilization of the carrier protein, prior to lyophilization the carrier protein is diafiltered against NaCl and the w/w ratio of NaCl/protein carrier protein is adjusted to about 0.5 to about 1.5. In one embodiment, the ratio of NaCl to carrier protein is about 1.

In one embodiment, the carrier protein used in the method of producing an isolated *S. aureus* type 5 or 8 capsular polysaccharide-carrier protein conjugate comprises $CRM_{197}$.

In one embodiment, the $CRM_{197}$ used in the method of producing an isolated *S. aureus* type 5 or 8 capsular polysaccharide-carrier protein conjugate is reacted with the activated serotype 5 or 8 polysaccharide at a ratio by weight of about 1:1.

In one embodiment, the method of producing an isolated *S. aureus* type 5 or 8 capsular polysaccharide-carrier protein conjugate comprises the step of mixing the type 5 or 8 capsular polysaccharide with imidazole or triazole prior to mixing with CDT in an organic solvent.

In one embodiment, the method of producing an isolated *S. aureus* type 5 or 8 capsular polysaccharide:carrier protein conjugate comprises the step of hydrolyzing the serotype 5 or 8 polysaccharide-carrier protein conjugate to remove unreacted activation groups.

In one embodiment, the invention provides a method of producing an immunogenic conjugate comprising an isolated *Staphylococcus aureus* serotype 5 or 8 capsular polysaccharide conjugated to a carrier protein, the method comprising the steps of: reacting a *S. aureus* serotype 5 or 8 capsular polysaccharide with 3-(2-pyridyldithio)-propionyl hydrazide (PDPH) and a carbodiimide in an organic solvent to produce a PDPH-linked polysaccharide; reacting the PDPH-linked polysaccharide with a reducing agent to produce an activated polysaccharide; isolating the activated serotype 5 or 8 polysaccharide to produce an isolated activated serotype 5 or 8 polysaccharide; providing an activated carrier protein; reacting the isolated activated serotype 5 or 8 polysaccharide with the activated carrier protein to produce a serotype 5 or 8 polysaccharide-carrier protein conjugate; whereby an immunogenic conjugate comprising an isolated *S. aureus* serotype 5 or 8 capsular polysaccharide conjugated to a carrier protein is produced. In one embodiment, the activated carrier protein is isolated prior to reacting the activated carrier protein with the activated polysaccharide.

In one embodiment, the step of isolating the activated carrier protein further comprises lyophilizing the isolated activated serotype 5 or 8 polysaccharide to produce a lyophilized activated serotype 5 or 8 polysaccharide.

In one embodiment, the bromoacetic acid is a N-hydroxysuccinimide ester of bromoacetic acid (BAANS).

In one embodiment, the method of producing serotype 8 capsular polysaccharide-carrier protein conjugate which utilizes PDPH comprises the use of an organic solvent that is a polar aprotic solvent. In one embodiment, the polar aprotic solvent is selected from the group consisting of dimethyl sulfoxide (DMSO), dimethylformamide (DMF), dimethylacetamide, N-methyl-2-pyrrolidone, and hexamethylphosphoramide (HMPA). In one embodiment, the organic solvent is dimethyl sulfoxide (DMSO).

In one embodiment, the carbodiimide used in the method of producing serotype 5 or 8 capsular polysaccharide-carrier protein conjugate which utilizes PDPH is 1-Ethyl-3-(3-dimethylaminopropyl)-carbodiimide (EDAC).

In one embodiment, the method of producing serotype 5 or 8 capsular polysaccharide-carrier protein conjugate which utilizes PDPH and EDAC comprises the step of reacting the serotype 5 or 8 capsular polysaccharide with PDPH and EDAC in an organic at a polysaccharide:PDPH:EDAC ratio by weight of about 1:5:3.

In one embodiment, the reducing agent used in the method of producing serotype 5 or 8 capsular polysaccharide-carrier protein conjugate which utilizes PDPH and EDAC is dithiothreitol (DTT).

In one embodiment, activation of the carrier protein in the method of producing serotype 5 or 8 capsular polysaccharide-carrier protein conjugate which utilizes PDPH and EDAC comprises reacting the carrier protein with a bromoacetic acid.

In one embodiment, the step of isolating the activated serotype 5 or 8 polysaccharide in the method of producing serotype 5 or 8 capsular polysaccharide-carrier protein conjugate which utilizes PDPH and EDAC comprises diafiltration.

In one embodiment, the method of producing serotype 5 or 8 capsular polysaccharide-carrier protein conjugate which utilizes PDPH and EDAC comprises the step of hydrolyzing the serotype 5 or 8 polysaccharide-carrier protein conjugate to remove unreacted activation groups. In one embodiment, the step of hydrolyzing the serotype 5 or 8 polysaccharide-carrier protein conjugate comprises the addition of cysteamine hydrochloride.

In one embodiment, the method of producing serotype 5 or 8 capsular polysaccharide-carrier protein conjugate which utilizes PDPH and EDAC further comprises isolating the immunogenic conjugate comprising an isolated *S. aureus* serotype 5 or 8 capsular polysaccharide conjugated to a carrier protein.

In one embodiment, the isolation of the serotype 5 or 8 polysaccharide-carrier protein conjugate comprises diafiltration.

In one embodiment, the carrier protein used in the method of producing serotype 5 or 8 capsular polysaccharide-carrier protein conjugate which utilizes PDPH and EDAC comprises $CRM_{197}$.

In one embodiment, the $CRM_{197}$ in the method of producing serotype 5 or 8 capsular polysaccharide-$CRM_{197}$ conjugate which utilizes PDPH and EDAC is added in a ratio by weight of about 1:1 $CRM_{197}$:capsular polysaccharide molecule.

In one embodiment, activated type 5 or 8 capsular polysaccharide used in the method of producing serotype 5 or 8 capsular polysaccharide-carrier protein conjugate which utilizes PDPH and EDAC has a size, between about 50 kd and about 500 kd.

In one embodiment, immunogenic conjugate produced in the method of producing serotype 5 or 8 capsular polysaccharide-carrier protein conjugate which utilizes PDPH and EDAC has a size between about between 400 kd and about 5000 kd.

In one embodiment, the invention provides an immunogenic composition comprising a type 5 or 8 capsular polysaccharide-carrier protein conjugate produced by any of the methods described herein.

In one embodiment, the invention provides an immunogenic composition comprising a type 5 or 8 capsular polysaccharide-carrier protein conjugate produced by any of the methods described herein and at least one of an adjuvant, diluent or carrier. In one embodiment, the immunogenic compositions comprise an aluminum based adjuvant that can be selected from the group consisting of aluminum phosphate, aluminum sulfate and aluminum hydroxide. In one embodiment, the immunogenic compositions described herein comprise the adjuvant aluminum phosphate.

The immunogenic compositions described herein can comprise less than 30% and less than 20% free type 5 or 8 polysaccharide compared to the total amount of type 5 or 8 polysaccharide. The immunogenic compositions described herein can be stored in water or a low ionic strength neutral pH buffer.

In one embodiment, the invention provides a method of reducing or preventing a Staphylococcal infection, disease or condition associated with a *Staphylococcus* bacteria in a subject, the method comprising the step of administering a therapeutically or prophylactically amount of an immunogenic composition as described herein to the subject. In one embodiment the infection, disease or condition is selected from the group consisting of invasive *Staphylococcus aureus*, sepsis and carriage.

In one embodiment, the invention provides a method of reducing or preventing a Staphylococcal infection in a subject undergoing a surgical procedure, the method comprising the step of administering a prophylactically effective amount of an immunogenic composition as described herein to the subject prior to the surgical procedure.

In one embodiment, the method of the invention comprises the substitution of CDI for CDT.

In one embodiment, the invention provides a *Staphylococcus aureus* Type 5 or 8 capsular polysaccharide having a molecular weight of between 50 kDa and 800 kDa covalently bound to a carrier protein; wherein the combined molecular weight of the polysaccharide covalently bound to the carrier protein is between about 400 kDa and 5000 kDa.

In one embodiment, the polysaccharide covalently bound to carrier protein comprises a polysaccharide portion that has a molecular weight range of between 70 kDa and 300 kDa. In one embodiment, the polysaccharide covalently bound to carrier protein has a molecular weight range of between 500 kDa and 2500 kDa.

In one embodiment, the carrier protein portion of the polysaccharide covalently bound to carrier protein comprises $CRM_{197}$. In one embodiment the $CRM_{197}$ is covalently linked to the polysaccharide through a carbamate linkage, an amide linkage, or both. In some embodiments, the molar ratio of conjugated lysines to $CRM_{197}$ is about 10:1 to about 25:1. In some embodiments, the polysaccharide covalently bound to carrier protein comprises at least one covalent linkage between $CRM_{197}$ at least at every 5 to 10 saccharide repeat units of the polysaccharide, in some embodiments, the polysaccharide covalently bound to carrier protein comprises at least one linkage between $CRM_{197}$ and polysaccharide occurs at every 5 saccharide repeat units of the polysaccharide. In some embodiments, the $CRM_{197}$ portion of the polysaccharide covalently bound to the $CRM_{197}$ comprises 5 to 22 lysines covalently linked to the polysaccharide. In some embodiments, the $CRM_{197}$ portion of the polysaccharide covalently bound to the $CRM_{197}$ comprises 5 to 23 lysines covalently linked to the polysaccharide. In some embodiments, the $CRM_{197}$ portion of the polysaccharide covalently bound to carrier protein of comprises 8 to 15 lysines covalently linked to the polysaccharide. In some embodiments, the $CRM_{197}$ portion of the polysaccharide covalently bound to carrier protein of comprises 8 to 12 lysines covalently linked to the polysaccharide.

In one embodiment the invention provides an immunogenic composition comprising a S. aureus type 5 or 8 polysaccharide covalently bound to carrier protein as described herein and at least one of an adjuvant, diluent, or carrier.

In one embodiment, the invention provides a method of administering an immunogenic composition comprising a S. aureus type 5 or 8 polysaccharide covalently bound to carrier protein as described herein to a subject to generate an immune response as described herein.

In one embodiment, the invention provides a method of isolating a polysaccharide with a molecular weight between 20 kDa and 1000 kDa.

In one embodiment, the invention provides an antibody generated by a capsular polysaccharide, an immunogenic conjugate, or an immunogenic composition of the present invention.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 2A shows an analysis of fractions from ion exchange chromatography (Q-Sepharose) for S. aureus serotype 8 capsular polysaccharide (O-Acetyl Assay) and teichoic acid (phosphate assay); FIG. 2B shows an analysis of fractions from ion exchange chromatography (Q-Sepharose) for S. aureus serotype 8 capsular polysaccharide by double immunodiffusion assay.

FIG. 3A shows the effect of pH (3.5, 4 or 5) at 95° C. on the reduction of S. aureus serotype 8 capsular polysaccharide molecular weight in heat treatment; FIG. 3B shows the effect of temperature (55° C., 75° C. or 95° C.) at pH 3.5 on the reduction of S. aureus serotype 8 capsular polysaccharide molecular weight in heat treatment.

FIG. 7A shows an analysis of fractions from ion exchange chromatography (Q-Sepharose) for S. aureus serotype 5 polysaccharide (O-Acetyl Assay) and teichoic acid (phosphate assay); FIG. 7B shows an analysis of fractions from ion exchange chromatography (Q-Sepharose) for S. aureus serotype 5 polysaccharide by double immunodiffusion assay.

FIG. 8A shows the effect of pH (3.5, 4 or 5) at 95° C. on the reduction of S. aureus serotype 5 capsular polysaccharide molecular weight in heat treatment; FIG. 8B shows the effect of temperature (55° C., 75° C. or 95° C.) at pH 3.5 on the reduction of S. aureus serotype 5 capsular polysaccharide molecular weight in heat treatment.

FIG. 10 shows colony forming units (CFU) recovered in kidneys alter challenge with S. aureus PFESA0266 in mice vaccinated with high molecular weight (HMW) CP5-CRM, low molecular weight (LMW) CP5-CRM or PP5-CRM control

DETAILED DESCRIPTION

Overview

Figure 1:
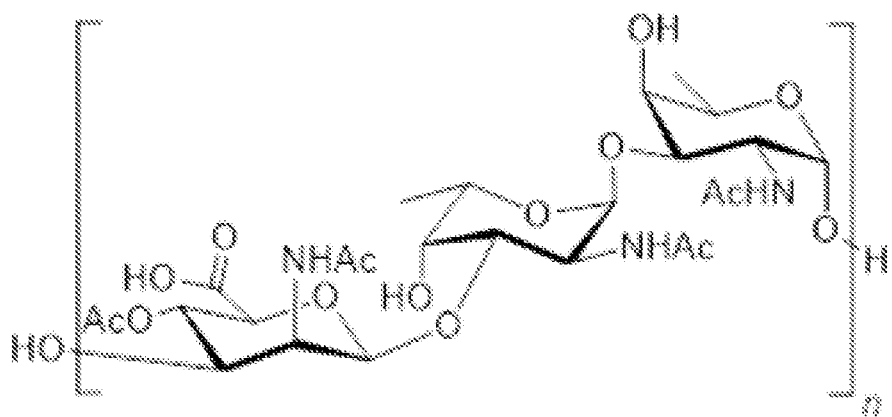
FIG. 1 shows a repeating polysaccharide structure of S. aureus serotype 8 capsular polysaccharide (N-acetyl mannosaminuronic acid is ManNAca, N-acetyl L-fucosamine is L-FucNAc, and N-acetyl D-fucosamine is D-FucNAc).

The present invention relates to immunogenic conjugates comprising S. aureus serotype 5 or 8 capsular polysaccharides conjugated to carrier proteins and methods for their preparation and use. Novel features of the immunogenic conjugates of the invention include the molecular weight profiles of the polysaccharides and resulting conjugates, the ratio of conjugated lysines per $CRM_{197}$ carrier protein and number of lysines covalently linked to the polysaccharide, the number of covalent linkages between the carrier protein and the polysaccharide as a function of repeat units of the polysaccharide, and the relative amount of free polysaccharide compared to the total polysaccharide. The term "free polysaccharide" as used herein means a polysaccharide that is not conjugated to the carrier protein, but is nevertheless present in the conjugate composition.

Methods for making the immunogenic conjugates of the invention involve covalent conjugation of the capsular polysaccharides with the carrier proteins using conjugation chemistry involving CDI (1,1-carbonyldiimidazole), CDT (1,1-carboyl-di-1,2,4-triazole) or PDPH (3-(2-pyridyldithio)-propionyl hydrazide). CDI is specific for CP8 conjugation only. Use of CDI/CDT results in a one-carbon or zero-carbon linker between capsular polysaccharide and carrier protein, while use of PDPH results in a covalent thioether bond between capsular polysaccharide and carrier protein.

Additional cross linkers for —SH (thiolated CP) to —NH$_2$ linkages include but are not limited to: sulfa-LC-SMPT; sulfo-LC-SMPT (4-sulfosuccinimidyl-6-methyl-a-(2-pyridyldithio)toluamido]hexanoate)); sulfo-KMUS (N-[k-maleimidoundecanoyloxy]sulfosuccinimide ester); sulfo-LC-SPDP (sulfosuccinimidyl 6-(3'-[2-pyridyldithio]-propionamido)hexanoate) which cleaves by thiols; sulfo-SMPB (sulfosuccinimidyl 4-[p-maleimidophenyl]butyrate); sulfo-SIAB (N-sulfosuccinimidyl[4-iodoacetyl]aminobenzoate); sulfa-EMCS ([N-e-maleimidocaproyloxy]sulfosuccinimide ester); EMCA (N-e-maleimidocaproic acid); sulfo-SMCC (sulfosuccinimidyl 4-[N-maleimidomethyl] cyclohexane-1-carboxylate); sulfo-MBS (m-maleimidobenzoyl-N-hydroxysulfosuccinimide ester); sulfo-GMBS (N-[g-maleimidobutyryloxy]sulfosuccinimide ester); BMPA (N-β-maleimidopropionic acid); 2-immunothiolane hydrochloride; 3-(2-pyridyldithio)propionic acid N-succinimidyl ester; 3-malemidopropionic acid N-succinimidyl ester; 4-maleimidobutyric acid N-succinimidyl ester; SMPT (4-succinimidyloxycarbonyl-methyl-a-[2-pyridyldithio]toluene); LC-SMCC (succinimidyl-4-[N-maleimidomethyl]cyclohexane-1-carboxy-[6-amidocaproate]); KMUA (N-k-maleimidoundecanoic acid); LC-SPDP (succinimidyl 6-(3-[2-pyridyldithio]-propionamido)hexanoate); SMPH (succinimidyl-6-[β-maleimidopropionamido]hexanoate); SMPB (succinimidyl 4-[p-maleimidophenyl]butyrate); SIAB (N-succinimidyl[4-iodoacetyl]aminobenzoate); EMCS ([N-e-Maleimidocaproyloxy]succinimide ester); SMCC (succinimidyl 4-[N-maleimidomethyl]cyclohexane-1-carboxylate); MBS (m-Maleimidobenzoyl-N-hydroxysuccinimide ester); SBAP (succinimidyl 3-[bromoacetamido]propionate); BMPS (N-[β-maleimidopropyloxylsuccinimide ester); AMAS N-(a-maleimidoacetoxy)succinimide ester); SIA (N-succinimidyl iodoacetate); and N-succinimidyl (4-iodoacetyl)-aminobenzoate.

The agents can also be crosslinked using crosslinkers for —SH to —OH groups. Such cross linkers include but are not limited to PMPI (N-[p-maleimidophenyl]isocyanate).

The compositions and methods described herein are useful in a variety of applications. For example, the conjugates can be used in the production of conjugate immunogenic compositions to protect recipients from S. aureus infections. Alternatively, the various conjugates can be used in the production of antibodies against bacterial capsular polysaccharides, which subsequently can be used in research and clinical laboratory assays, such as bacterial detection and serotyping. Such antibodies may also be used to confer passive immunity to a subject. In some embodiments, the antibodies produced against bacterial polysaccharides are functional in either an animal efficacy model or in an opsonophagocytic killing assay.

Unless defined otherwise, all technical and scientific terms used herein have the same meaning as commonly understood by one of ordinary skill in the art to which the invention pertains. Although any methods and materials similar or equivalent to those described herein can be used in the practice or testing of the present invention, the preferred methods and materials are described herein. In describing the embodiments and claiming the invention, certain terminology will be used in accordance with the definitions set out below.

As used herein, the singular forms "a," "an," and "the" include plural references unless the context clearly dictates otherwise. Thus, e.g., references to "the method" includes one or more methods, and/or steps of the type described herein and/or which will become apparent to one of ordinary skill in the art upon reading this disclosure and so forth.

As used herein, "about" means within a statistically meaningful range of a value such as a stated concentration range, time frame, molecular weight, temperature or pH. Such a range can be within an order of magnitude, typically within 20%, more typically still within 10%, and even more typically within 5% of a given value or range. The allowable variation encompassed by the term "about" will depend upon the particular system under study, and can be readily appreciated by one of ordinary skill in the art. Whenever a range is recited within this application, every whole number integer within the range is also contemplated as an embodiment of the invention.

It is noted that in this disclosure, terms such as "comprises," "comprised," "comprising," "contains," "containing" and the like can have the meaning attributed to them in U.S. patent law; e.g., they can mean "includes," "included," "including" and the like. Such terms refer to the inclusion of a particular ingredients or set of ingredients without excluding any other ingredients. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. patent law; namely, that these terms are closed ended. Accordingly, these terms refer to the inclusion of a particular ingredient or set of ingredients and the exclusion of all other ingredients.

Immunogenic Conjugates

As described above, the present invention relates to immunogenic conjugates comprising S. aureus serotype 5 or 8 capsular polysaccharides conjugated to carrier proteins. One embodiment of the invention provides immunogenic conjugates comprising a S. aureus serotype 5 or 8 capsular polysaccharide conjugated to carrier molecule or protein having one or more of the following features: the polysaccharide has a molecular weight of between 50 kDa and 700 kDa; the immunogenic conjugate has a molecular weight of between 500 kDa to 2500 KDa; and the conjugate comprises less than about 30% free polysaccharide relative to total polysaccharide. In some embodiments, the polysaccharide has a molecular weight of between 20 kDa and 1000 kDa. In some embodiments the immunogenic conjugate has a molecular weight of between 200 kDa and 5000 kDa. In other embodiments, the conjugate comprises less than about 25%, about 20%, about 15%, about 10%, or about 5% free polysaccharide relative to total polysaccharide.

The "conjugates" as used herein comprise a capsule polysaccharide usually of a desired range of molecular weight and a carrier protein, wherein the capsule polysaccharide is conjugated to the carrier protein. Conjugates may or may not contain some amount of free capsule polysaccharide. As used herein, "free capsule polysaccharide" refers to capsule polysaccharide that is non-covalently associated with (i.e., non-covalently bound to, adsorbed to or entrapped in or with) the conjugated capsular polysaccharide-carrier protein. The terms "free capsule polysaccharide," "free polysaccharide" and "free saccharide" may be used interchangeably and are intended to convey the same meaning.

Regardless Of the nature of the carrier molecule, it can be conjugated to the capsular polysaccharide either directly or through a linker. As used herein, "to conjugate," "conjugated" and "conjugating" refer to a process whereby a bacterial capsular polysaccharide is covalently attached to the carrier molecule. Conjugation enhances the immunogenicity of the bacterial capsular polysaccharide. The conjugation can be performed according to the methods described below or by other processes known in the art.

The molecular weight of the *S. aureus* capsular polysaccharide is a consideration for use in immunogenic compositions. High molecular weight capsular polysaccharides are able to induce certain antibody immune responses due to a higher valence of the epitopes present on the antigenic surface. The isolation of "high molecular weight capsular polysaccharides" is contemplated for use in the compositions and methods of the present invention. In one embodiment of the invention, high molecular weight serotype 5 or 8 capsular polysaccharide can be isolated and purified ranging from 20 kDa to 1000 kDa in molecular weight. In one embodiment of the invention, nigh molecular weight serotype 5 or 8 capsular polysaccharide can be isolated and purified ranging from 50 kDa to 700 kDa in molecular weight. In one embodiment of the invention, high molecular weight serotype 5 or 8 capsular polysaccharide can be isolated and purified ranging from 50 kDa to 300 kDa in molecular weight. In one embodiment, high molecular weight serotype 5 or 8 capsular polysaccharide can be isolated and purified ranging from 70 kDa to 300 kDa in molecular weight. In one embodiment, high molecular weight serotype 5 or 8 capsular polysaccharide can be isolated and purified ranging from 90 kDa to 250 kDa in molecular weight. In one embodiment, high molecular weight serotype 5 or 8 capsular polysaccharide can be isolated and purified ranging from 90 kDa to 150 kDa in molecular weight. In one embodiment, high molecular weight serotype 5 or 8 capsular polysaccharide can be isolated and purified ranging from 90 kDa to 120 kDa in molecular weight. In one embodiment, high molecular weight serotype 5 or 8 capsular polysaccharide can be isolated and purified ranging from 80 kDa to 120 kDa in molecular weight. Other ranges of high molecular weight serotype 5 or 8 capsular polysaccharide that can be isolated and purified by the methods of this invention include 70 kDa to 100 kDa in molecular weight; 70 kDa to 110 kDa in molecular weight; 70 kDa to 120 kDa in molecular weight; 70 kDa to 130 kDa in molecular weight; 70 kDa to 140 kDa in molecular weight; 70 kDa to 150 kDa in molecular weight; 70 kDa to 160 kDa in molecular weight; 80 kDa to 110 kDa in molecular weight; 80 kDa to 120 kDa in molecular weight; 80 kDa to 130 kDa in molecular weight; 80 kDa to 140 kDa in molecular weight; 80 kDa to 150 kDa in molecular weight; 80 kDa to 160 kDa in molecular weight; 90 kDa to 110 kDa in molecular weight; 90 kDa to 120 kDa in molecular weight; 90 kDa to 130 kDa in molecular weight; 90 kDa to 140 kDa in molecular weight; 90 kDa to 150 kDa in molecular weight; 90 kDa to 160 kDa in molecular weight; 100 kDa to 120 kDa in molecular weight; 100 kDa to 130 kDa in molecular weight; 100 kDa to 140 kDa in molecular weight; 100 kDa to 150 kDa in molecular weight; 100 kDa to 160 kDa in molecular weight; and similar desired molecular weight ranges. Any whole number integer within any of the above ranges is contemplated as an embodiment of the invention.

In one embodiment, the conjugate has a molecular weight of between about 50 kDa and about 5000 kDa in molecular weight. In one embodiment, the conjugate has a molecular weight of between about 200 kDa and about 5000 kDa in molecular weight. In one embodiment, the immunogenic conjugate has a molecular weight of between about 500 kDa and about 2500 kDa. In one embodiment, the immunogenic conjugate has a molecular weight of between about 500 kDa and about 2500 kDa. In one embodiment, the immunogenic conjugate has a molecular weight of between about 600 kDa and about 2800 kDa. In one embodiment, the immunogenic conjugate has a molecular weight of between about 700 kDa and about 2700 kDa. In one embodiment, the immunogenic conjugate has a molecular weight of between about 1000 kDa and about 2000 kDa; between about 1800 kDa and about 2500 kDa; between about 1100 kDa and about 2200 kDa; between about 1900 kDa and about 2700 kDa; between about 1200 kDa and about 2400 kDa; between about 1700 kDa and about 2600 kDa; between about 1300 kDa and about 2600 kDa; between about 1600 kDa and about 3000 kDa. Any whole number integer within any of the above ranges is contemplated as an embodiment of the invention As used herein, "immunogenic" means an ability of an antigen (or an epitope of the antigen), such as a bacterial capsular polysaccharide or a conjugate immunogenic composition comprising the antigen, to elicit an immune response in a host such as a mammal, either humorally or cellularly mediated, or both. Accordingly, "immunogenic conjugate" or "conjugate" as used herein means any immunogenic conjugate containing an antigen or antigenic determinant (i.e., epitope) of a bacterial capsular polysaccharide conjugated to a carrier molecule that can be used to elicit an immune response. The immunogenic conjugate may serve to sensitize the host by the presentation of the antigen in association with MHC molecules at a cell surface. In addition, antigen-specific T-cells or antibodies can be generated to allow for the future protection of an immunized host. Immunogenic conjugates thus can protect the host from one or more symptoms associated with infection by the bacteria, or may protect the host from death due to the infection with the bacteria associated with the capsular polysaccharide. Immunogenic conjugates may also be used to generate polyclonal or monoclonal antibodies, which may be used to confer passive immunity to a subject. Immunogenic conjugates may also be used to generate antibodies that are functional as measured by the killing of bacteria in either an animal efficacy model or via an opsonophagocytic killing assay.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, unless otherwise indicated by context, the term is intended to encompass not only intact polyclonal or monoclonal antibodies, but also engineered antibodies (e.g., chimeric, humanized and/or derivatized to alter effector functions, stability and other biological activities) and fragments thereof (such as Fab, Fab', F(ab')2, Fv), single chain (ScFv) and domain antibodies, including shark and camelid antibodies), and fusion proteins comprising an antibody portion, multivalent antibodies, multispecific antibodies (e.g., bispecific antibodies so long as they exhibit the desired biological activity) and antibody fragments as described herein, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2 in humans. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Antibody fragments" comprise only a portion of an intact antibody, wherein the portion preferably retains at least one, preferably most or all, of the functions normally associated with that portion when present in an intact antibody.

The term "antigen" generally refers to a biological molecule, usually a protein, peptide, polysaccharide or conjugate in an immunogenic composition, or immunogenic substance that can stimulate the production of antibodies or T-cell responses, or both, in an animal, including compositions that are injected or absorbed into an animal. The immune response may be generated to the whole molecule, or to a various portions of the molecule (e.g., an epitope or hapten). The term may be used to refer to an individual molecule or to a homogeneous or heterogeneous population of antigenic molecules. An antigen is recognized by antibodies, T-cell receptors or other elements of specific humoral and/or cellular immunity. "Antigen" also includes all related antigenic epitopes. Epitopes of a given antigen can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715; each of which is incorporated herein by reference as if set forth in its entirety. Similarly, conformational epitopes may be identified by determining spatial conformation of amino acids such as by, e.g., x-ray crystallography and 2-dimensional nuclear magnetic resonance. See, e.g., Epitope Mapping Protocols, supra. Furthermore, for purposes of the present invention, "antigen" also can be used to refer to a protein that includes modifications, such as deletions, additions and substitutions (generally conservative in nature, but they may be non-conservative), to the native sequence, so long as the protein maintains the ability to elicit an immunological response. These modifications may be deliberate, as through site-directed mutagenesis, or through particular synthetic procedures, or through a genetic engineering approach, or may be accidental, such as through mutations of hosts, which produce the antigens. Furthermore, the antigen can be derived, obtained, or isolated from a microbe, e.g., a bacterium, or can be a whole organism. Similarly, an oligonucleotide polynucleotide, which expresses an antigen, such as in nucleic acid immunization applications, is also included in the definition. Synthetic antigens are also included, e.g., polyepitopes, flanking epitopes, and other recombinant or synthetically derived antigens (Bergmann et al. (1993) *Eur. J. Immunol.* 23:2777 2781; Bergmann et al. (1996) *J. Immunol.* 157:3242-3249; Suhrbier (1997) *Immunol. Cell Biol.* 75:402 408; Gardner et al. (1998) 12th World AIDS Conference, Geneva, Switzerland, Jun. 28 to Jul. 3, 1998).

A "protective" immune response refers to the ability of an immunogenic composition to elicit an immune response, either humoral or cell mediated, or both, which serves to protect a subject from an infection. The protection provided need not be absolute, i.e., the infection need not be totally prevented or eradicated, if there is a statistically significant improvement compared with a control population of subjects, e.g. infected animals not administered the vaccine or immunogenic composition. Protection may be limited to mitigating the severity or rapidity of onset of symptoms of the infection. In general, a "protective immune response" would include the induction of an increase in antibody levels specific for a particular antigen in at least 50% of subjects, including some level of measurable functional antibody responses to each antigen. In particular situations, a "protective immune response" could include the induction of a two fold increase in antibody levels or a four fold increase in antibody levels specific for a particular antigen in at least 50% of subjects, including some level of measurable functional antibody responses to each antigen. In certain embodiments, opsonising antibodies correlate with a protective immune response. Thus, protective immune response may be assayed by measuring the percent decrease in the bacterial count in an opsonophagocytosis assay, for instance those described below. Preferably, there is a decrease in bacterial count of at least 10%, 25%, 50%, 65%, 75%, 80%, 85%, 90%, 95% or more. The "immunogenic amount" of a particular conjugate in a composition are generally dosed based on total polysaccharide, conjugated and non-conjugated for that conjugate. For example, a serotype 5 or 8 capsular polysaccharide conjugate with 20% free polysaccharide will have about 80 mcg of conjugated polysaccharide and about 20 mcg of non-conjugated polysaccharide in a 100 mcg dose. The protein contribution to the conjugate is usually not considered when calculating the dose of a conjugate. The amount of conjugate can vary depending upon the staphylococcal serotype. Generally, each dose will comprise 0.1 to 100 mcg of polysaccharide, particularly 0.1 to 10 mcg, and more particularly 1 to 10 mcg.

The term "subject" refers to a mammal, bird, fish, reptile, or any other animal. The term "subject" also includes humans. The term "subject" also includes household pets. Non-limiting examples of household pets include: dogs, cats, pigs, rabbits, rats, mice, gerbils, hamsters, guinea pigs, ferrets, birds, snakes, lizards, fish, turtles, and frogs. The term "subject" also includes livestock animals. Non-limiting examples of livestock animals include: alpaca, bison, camel, cattle, deer, pigs, horses, llamas, mules, donkeys, sheep, goats, rabbits, reindeer, yak, chickens, geese, and turkeys.

Figure 6:
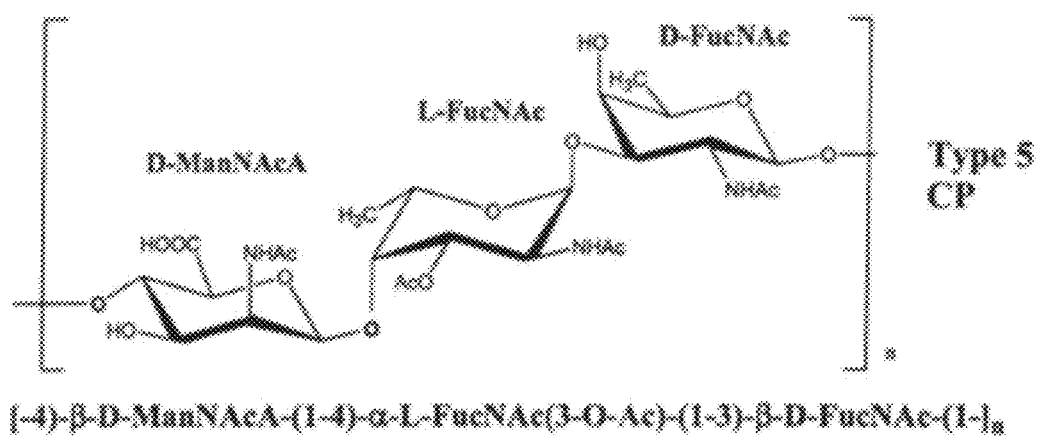
FIG. 6 shows a repeating polysaccharide structure of S. aureus serotype 5 polysaccharide (N-acetyl mannosaminuronic acid is ManNAcA, N-acetyl L-fucosamine is L-FucNAc, and N-acetyl D-fucosamine is D-FucNAcA).

As shown in FIGS. 6 and 1, respectively, *S. aureus* serotype 5 and 8 capsular polysaccharides have the following structures: serotype 5 [→4)-β-D-ManNAcA-(1→4)-α-L-FucNAc (3-O—Ac)-(1→3)-β-D-FucNAc-(1→]$_n$. and serotype 8 [→3)-β-D-ManNAcA(4-O—Ac)-(1→3)-α-L-FucNAc-(1→3)-α-D-FucNAc-(1→]$_n$. See, Jones (2005) *Carbohydr. Res.* 340:1097-1106. Serotype 8 capsular polysaccharide has similar trisaccharide repeating units to serotype 5 capsular polysaccharide; however, they differ in the sugar linkages and in sites of O-acetylation, which produces serologically distinct patterns of immunoreactivity (Fournier et al. (1984) *Infect. Immun.* 45:87-93; and Moreau et al. (1990) *Carbohydr. Res.* 201:285-297). Serotype 8 and 5 capsular polysaccharides are therefore relatively complex carbohydrates that are water soluble, usually acidic, and were previously thought to have molecular weights of approximately 25 kDa (Fattom (1990) *Infect. Immun.* 58, 2367-2374).

In some embodiments, the serotype 5 and/or 8 capsular polysaccharides of the invention are O-acetylated. In some embodiments, the degree of O-acetylation of type 5 capsular polysaccharide or oligosaccharide is 10-100%, 20-100%, 30-100%, 40-100%, 50-100%. 60-100%, 70-100%, 80-100%, 90-100%, 50-90%, 60-90%, 70-90% or 80-90%. In some embodiments, the degree of O-acetylation of type 8 capsular polysaccharide or oligosaccharide is 10-100% 20-100%, 30-100%, 40-100%, 50-100%. 60-100%, 70-100%, 80-100%, 90-100%, 50-90%, 60-90%, 70-90% or 80-90%. In some embodiments, the degree of O-acetylation of type 5 and type 8 capsular polysaccharides or oligosaccharides is 10-100%, 20-100%, 30-100%, 40-100%, 50-100%. 60-100% 70-100%, 80-100%, 90-100%, 50-90%, 60-90%, 70-90% or 80-90%.

The degree of O-acetylation of the polysaccharide or oligosaccharide can be determined by any method known in the art, for example, by proton NMR (Lemercinier and Jones 1996, Carbohydrate Research 296; 83-96, Jones and Lemercinier 2002, J Pharmaceutical and Biomedical analysis 30; 1233-1247, WO 05/033148 or WO 00/56357). Another commonly used method is described by Hestrin. (1949) J. Biol. Chem. 180; 249-261.

In some embodiments, the serotype 5 and/or 8 capsular polysaccharides of the invention are used to generate antibodies that are functional as measured by the killing of bacteria in an animal efficacy model or an opsonophagocytic killing assay that demonstrates that the antibodies kill the bacteria. Functional killing may not be demonstrated using an assay that monitors the generation of antibodies alone, which is not indicative of the importance of O-acetylation in efficacy.

Capsular polysaccharides such as serotype 5 or 8 can be obtained directly from bacteria using isolation procedures known to one of ordinary skill in the art. See, e.g., Fournier et al. (1984), supra; Fournier et al. (1987) *Ann. Inst. Pasteur/ Microbiol.* 138:561-567; US Patent Application Publication No. 2007/0141077; and Int'l Patent Application Publication No. WO 00/56357; each of which is incorporated herein by reference as if set forth in its entirety). In addition, they can be produced using synthetic protocols. Moreover, serotype 5 or 8 capsular polysaccharide can be recombinantly produced using genetic engineering procedures also known to one of ordinary skill in the art (see, Sau et al. (1997) *Microbiology* 143:2395-2405; and U.S. Pat. No. 6,027,925; each of which is incorporated herein by reference as if set forth in its entirety).

One *S. aureus* strain that can be used to obtain isolated serotype 8 capsular polysaccharide is *S. aureus* R2 PFESA0286. This strain was selected by flow cytometry with rabbit anti-serotype 8 polysaccharide antibodies after cultivation of *S. aureus* PFESA0286 (American Type Culture Collection; Manassas, Va.: ATCC Accession No. 495:25;) in Modified Frantz Broth. Two populations, R1 and R2, were observed during flow cytometry. R1 and R2 were purified and re-cultured. R2 yielded a serotype 8 capsular polysaccharide. Flow cytometric analysis showed a homogenous fluorescence intensity. As such, R2 was selected for serotype 8 capsular polysaccharide production.

One *S. aureus* strain that can be used to obtain isolated serotype 5 capsular polysaccharide is *S. aureus* PFESA0266. This strain produces serotype 5 capsular polysaccharide during growth, and production peaks when cells are in a stationary phase. Other *S. aureus* type 5 or type 8 strains can be used to make the respective polysaccharides that are obtained either from established culture collections or clinical specimens.

Another component of the immunogenic conjugate of the invention is a carrier molecule or protein to which the bacterial capsular polysaccharide is conjugated. The term "protein carrier" or "carrier protein," refers to any protein molecule that may be conjugated to an antigen (such as the capsular polysaccharides) against which an immune response is desired. Conjugation to an carrier can enhance the immunogenicity of the antigen. The conjugation can be performed by standard procedures. Preferred protein carriers for the antigens are toxins, toxoids or any mutant cross-reactive material (CRM) of the toxin from tetanus, diphtheria, pertussis, *Pseudomonas, E. coli, Staphylococcus* and *Streptococcus*. In one embodiment, a particularly preferred carrier is of diphtheria toxoid $CRM_{197}$, derived from *C. diphtheriae* strain C7 (β197), which produces $CRM_{197}$ protein. This strain has ATCC accession No. 53281. A method for producing $CRM_{197}$ is described in U.S. Pat. No. 5,614,382, which is incorporated herein by reference as if set forth in its entirety. Alternatively, a fragment or epitope of the protein carrier or other immunogenic protein can be used. For example, a haptenic antigen can be coupled to a T-cell epitope of a bacterial toxin, toxoid or CRM. See, U.S. Pat. No. 150,688, filed Feb. 1, 1988, entitled "Synthetic Peptides Representing a T-Cell Epitope as a Carrier Molecule For Conjugate Vaccines"; incorporated herein by reference as if set forth in its entirety. Other suitable carrier proteins include inactivated bacterial toxins such as cholera toxoid (e.g., as described in Int'l Patent Application No. WO 2004/083251), *E. coli* LT, *E. coli* ST, and exotoxin A from *Pseudomonas aeruginosa*. Bacterial outer membrane proteins such as outer membrane complex c (OMPC), porins, transferrin binding proteins, pneumolysin, pneumococcal surface protein A (PspA), pneumococcal adhesion protein (PsaA) or *Haemophilus influenzae* protein D also can be used. Other proteins, such as ovalbumin, keyhole limpet hemocyanin (KLH), bovine serum albumin (BSA) or purified protein derivative of tuberculin (PPD) also can be used as carrier proteins.

Accordingly, in one embodiment, the carrier protein within the immunogenic conjugate of the invention is $CRM_{197}$, and the $CRM_{197}$ is covalently linked to the capsular polysaccharide via a carbamate linkage, an amide linkage, or both. In some embodiments, the carrier protein within the immunogenic conjugate of the invention is $CRM_{197}$, and the $CRM_{197}$ is covalently linked to the capsular polysaccharide via a thioether bond. The number of lysine residues in the carrier protein that become conjugated to a capsular polysaccharide can be characterized as a range of conjugated lysines. For example, in a given immunogenic composition, the $CRM_{197}$ may comprise 5 to 15 lysines out of 39 covalently linked to the capsular polysaccharide. Another way to express this parameter is that 12% to 40% of $CRM_{197}$ lysines are covalently linked to the capsular polysaccharide. For example, in a given immunogenic composition, the $CRM_{197}$ may comprise 18 to 22 lysines out of 39 covalently linked to the capsular polysaccharide. Another way to express this parameter is that 40% to 60% of $CRM_{197}$ lysines are covalently linked to the capsular polysaccharide. In some embodiments, the $CRM_{197}$ comprises 5 to 15 lysines out of 39 covalently linked to CP8. Another way to express this parameter is that 12% to 40% of $CRM_{197}$ lysines are covalently linked to CP8. In some embodiments, the $CRM_{197}$ comprises 18 to 22 lysines out of 39 covalently linked to CP5. Another way to express this parameter is that 40% to 60% of $CRM_{197}$ lysines are covalently linked to CP5.

As discussed above, the number of lysine residues in the carrier protein conjugated to the capsular polysaccharide can be characterized as a range of conjugated lysines, which may be expressed as a molar ratio. For example, the molar ratio of conjugated lysines to $CRM_{197}$ in the CP8 immunogenic conjugate can be between about 18:1 to about 22:1. In one embodiment, the range of molar ratio of conjugated lysines to $CRM_{197}$ in the CP8 immunogenic conjugate can be between about 15:1 to about 25:1. In one embodiment, the range of molar ratio of conjugated lysines to $CRM_{197}$ in the CP8 immunogenic conjugate can be between about 14:1 to about 20:1; about 12:1 to about 18:1; about 10:1 to about 16:1; about 8:1 to about 14:1; about 6:1 to about 12:1; about 4:1 to about 10:1; about 20:1 to about 26:1; about 22:1 to about 28:1; about 24:1 to about 30:1; about 26:1 to about 32:1; about 28:1 to about 34:1; about 30:1 to about 36:1; about 5:1 to about 10:1; about 5:1 to about 20:1; about 10:1 to about 20:1; or about 10:1 to about 30:1. Also, the molar ratio of conjugated lysines to CRM197 in the CP5 immunogenic conjugate can be between about 3:1 and 25:1. In one embodiment, the range of molar ratio of conjugated lysines to CRM197 in the CP5 immunogenic conjugate can be between about 5:1 to about 20:1. In one embodiment, the range of molar ratio of conjugated lysines to CRM197 in the CP5 immunogenic conjugate can be between about 4:1 to about 20:1; about 6:1 to about 20:1; about 7:1 to about 20:1; about 8:1 to about 20:1; about 10:1 to about 20:1; about 11:1 to about 20:1; about 12:1 to about 20:1; about 13:1 to about 20:1; about 14:1 to about 20:1; about 15:1 to about 20:1; about 16:1 to about 20:1; about 17:1 to about 20:1; about 18:1 to about 20:1; about 5:1 to about 18:1; about 7:1 to about 16:1; or about 9:1 to about 14:1.

Another way to express the number of lysine residues in the carrier protein conjugated to the capsular polysaccharide can be as a range of conjugated lysines. For example, in a given CP8 immunogenic conjugate, the $CRM_{197}$ may comprise 5 to 15 lysines out of 39 covalently linked to the capsular polysaccharide. Alternatively, this parameter can be expressed as a percentage. For example, in a given CP8 immunogenic conjugate, the percentage of conjugated lysines can be between 10% to 50%. In some embodiments, 20% to 50% of lysines can be covalently linked to CP8. Alternatively still, 30% to 50% of $CRM_{197}$ lysines can be covalently linked to CP8; 10% to 40% of $CRM_{197}$ lysines; 10% to 30% of $CRM_{197}$ lysines; 20% to 40% of $CRM_{197}$ lysines; 25% to 40% of $CRM_{197}$ lysines; 30% to 40% of $CRM_{197}$ lysines; 10% to 30% of $CRM_{197}$ lysines; 15% to 30% of $CRM_{197}$ lysines; 20% to 30% of $CRM_{197}$ lysines; 25% to 30% of $CRM_{197}$ lysines; 10% to 15% of $CRM_{197}$ lysines; or 10% to 12% of $CRM_{197}$ lysines are covalently linked to CP8. Also, in a given CP5 immunogenic conjugate, the $CRM_{197}$ may comprise 18 to 22 lysines out of 39 covalently linked to the capsular polysaccharide. Alternatively, this parameter can be expressed as a percentage. For example, in a given CP5 immunogenic conjugate, the percentage of conjugated lysines can be between 40% to 60%. In some embodiments, 40% to 60% of lysines can be covalently linked to CP5. Alternatively still, 30% to 50% of $CRM_{197}$ lysines can be covalently linked to CP5; 20% to 40% of $CRM_{197}$ lysines; 10% to 30% of $CRM_{197}$ lysines; 50% to 70% of $CRM_{197}$ lysines; 35% to 65% of $CRM_{197}$ lysines; 30% to 60% of $CRM_{197}$ lysines; 25% to 55% of $CRM_{197}$ lysines; 20% to 50% of $CRM_{197}$ lysines; 15% to 45% of $CRK_{97}$ lysines; 10% to 40% of $CRM_{197}$ lysines; 40% to 70% of $CRM_{197}$ lysines; or 45% to 75% of $CRM_{197}$ lysines are covalently linked to CP5.

The frequency of attachment of the capsular polysaccharide chain to a lysine on the carrier molecule is another parameter for characterizing conjugates of capsule polysaccharides. For example, in one embodiment, at least one covalent linkage between $CRM_{197}$ and polysaccharide occurs for at least every 5 to 10 saccharide repeat units of the capsular polysaccharide. In another embodiment, there is at least one covalent linkage between $CRM_{197}$ and capsular polysaccharide for every 5 to 10 saccharide repeat units; every 2 to 7 saccharide repeat units, every 3 to 8 saccharide repeat units; every 4 to 9 saccharide repeat units; every 6 to 11 saccharide repeat units; every 7 to 12 saccharide repeat units; every 8 to 13 saccharide repeat units; every 9 to 14 saccharide repeat units; every 10 to 15 saccharide repeat units; every 2 to 6 saccharide repeat units, every 3 to 7 saccharide repeat units; every 4 to 8 saccharide repeat units; every 6 to 10 saccharide repeat units; every 7 to 11 saccharide repeat units; every 8 to 12 saccharide repeat units; every 9 to 13 saccharide repeat units; every 10 to 14 saccharide repeat units; every 10 to 20 saccharide repeat units; or every 5 to 10 saccharide repeat units of the capsular polysaccharide. In another embodiment, at least one linkage between $CRM_{197}$ and capsular polysaccharide occurs for every 2, 3, 4, 5, 6, 7, 8, 9, 10, 11, 12, 13, 14, 15, 16, 17, 18, 19, or 20 saccharide repeat units of the capsular polysaccharide.

One embodiment of the invention provides an immunogenic composition comprising any of the immunogenic conjugates comprising a S. aureus serotype 5 or 8 capsular polysaccharide conjugated to a carrier protein described above.

The term "immunogenic composition" relates to any pharmaceutical composition containing an antigen, e.g., a microorganism or a component thereof, which composition can be used to elicit an immune response in a subject. The immunogenic compositions of the present invention can be used to protect or treat a human susceptible to S. aureus infection, by means of administering the immunogenic compositions via a systemic, dermal or mucosal route or be used to generate a polyclonal or monoclonal antibody preparation that could be used to confer passive immunity on another subject. These administrations can include injection via the intramuscular, intraperitoneal, intradermal or subcutaneous routes; or via mucosal administration to the oral/alimentary, respiratory or genitourinary tracts. In one embodiment, intranasal administration is used for the treatment or prevention of nasopharyngeal carriage of S. aureus, thus attenuating infection at its earliest stage. Immunogenic compositions may also be used to generate antibodies that are functional as measured by the killing of bacteria in either an animal efficacy model or via an opsonophagocytic killing assay.

Optimal amounts of components for a particular immunogenic composition can be ascertained by standard studies involving observation of appropriate immune responses in subjects. Following an initial vaccination, subjects can receive one or several booster immunizations adequately spaced.

The immunogenic compositions of the present invention may also include one or more of the following antigens: ClfA, ClfB, SdrC, SdrD, SdrE MntC/SitC/Saliva Binding Protein, IsdB, IsdA, Opp3a, DltA, HtsA, LtaS, SdrH, SrtA, SpA, SBI, alpha-hemolysin (hla), beta-hemolysin, fibronectin-binding protein A (fnbA), coagulase, map, Panton-Valentine leukocidin (pvl), gamma-toxin (hlg), ica, immunodominant ABC transporter, RAP, autolysin, laminin receptors, IsaA/PisA, IsaB/PisB, SPOIIIE, SsaA, EbpS, Sasf, SasH, EFB (FIB), FnbB, Npase, EBP, bone sialo binding protein II; aureolysin precursor (AUR)/Sepp1, Cna, TSST-1, mecA, dPNAG, GehD, EbhA, EbhB, SSP-1, SSP-2 HBP, vitronectin binding protein, HarA, Enterotoxin A, Enterotoxin B, Enterotoxin C1, and novel autolysin.

In one embodiment, the immunogenic compositions of the invention further comprise at least one of an adjuvant, a buffer, a cryoprotectant, a salt, a divalent cation, a non-ionic detergent, an inhibitor of free radical oxidation, a diluent or a carrier. In one embodiment, the adjuvant within the immunogenic composition of the invention is an aluminum-based adjuvant. In one embodiment, the adjuvant is an aluminum-based adjuvant selected from the group consisting of aluminum phosphate, aluminum sulfate and aluminum hydroxide. In one embodiment, the adjuvant is aluminum phosphate.

An adjuvant is a substance that enhances the immune response when administered together with an immunogen or antigen. A number of cytakines or lymphokines have been shown to have immune modulating activity, and thus may be useful in a manner the same or similar to adjuvants, including, but not limited to, the interleukins 1-α, 1-β, 2, 4, 5, 6, 7, 8, 10, 12 (see, e.g., U.S. Pat. No. 5,723,127), 13, 14, 15, 16, 17 and 18 (and its mutant forms); the interferons-α, β and γ; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors α and β. Still other adjuvants that are useful with the immunogenic compositions described herein include chemokines, including without limitation, MCP-1, MfP-1α, MIP-1β, and RANTES; adhesion molecules, such as a selectin, e.g., L-selectin, P-selectin and E-selectin; mucin-like molecules, e.g., CD34, GlyCAM-1 and MadCAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as B7-1, B7-2, CD40 and CD40L; growth factors including vascular growth factor, nerve growth factor, fibroblast growth factor, epidermal growth factor, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspases, including ICE.

Suitable adjuvants used to enhance an immune response may further include, without limitation, MPL™ (3-O-deacylated monophosphoryi lipid A, Corixa; Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa, and those that are described in U.S. Pat. No. 6,113, 918. One such AGP is 2-[(R)-3-Tetradecanoyloxytetradecanoylamino]ethyl 2-Deoxy-4-O-phosphono-3-O-[(R)-3-tetradecanoyoxytetradecanoyl]-2-[(R1-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-hydroxyphosphoryloxy)-ethylamine (MTP-PE); oil-in-water emulsions, such as MF59 (U.S. Pat. No. 6,299,884) (containing 5% Squalene, 0.5% polysorbate 80, and 0.5% Span 85 (optionally containing various amounts of MTP-PE) formulated into submicron particles using a microfluidizer such as Model 110Y microfluidizer (Microlluidics, Newton, Mass.)), and SAF (containing 10% Squalene, 0.4% polysorbate 80, 5% pluronic-blocked polymer L121, and thr-MDP, either microfluidized into a submicron emulsion or vortexed to generate a larger particle size emulsion); incomplete Freund's adjuvant (IFA); aluminum salts (alum), such as aluminum hydroxide, aluminum phosphate, aluminum sulfate; Amphigen; Avridine; L121/squalene; D-lactide-polylactide/glycoside; pluronic polyols; killed *Bordetella*; saponins, such as Stimulon™ QS-21 (Antigenics, Framingham, Mass.), described in U.S. Pat. No. 5,057,540, Iscomatrix® (CSL Limited, Parkville, Australia), described in U.S. Pat. No. 5,254,339, and immunostimulating complexes (ISCOMS); *Mycobacterium tuberculosis*; bacterial lipopolysaccharides; synthetic polynucleotides such as oligonucleotides containing a CpG motif (e.g., U.S. Pat. No. 6,207,646); IC-31 (Intercell AG, Vienna, Austria), described in EP Patent Nos. 1,296, 713 and 1,326,634; a pertussis toxin (PT) or mutant thereof a cholera toxin or mutant thereof (e.g., U.S. Pat. Nos. 7,285, 281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291, 588).

The immunogenic composition optionally can comprise a pharmaceutically acceptable carrier. The term "pharmaceutically acceptable carrier" means a carrier approved by a regulatory agency of a Federal, a state government, or other regulatory agency, or listed in the U.S. Pharmacopeia or other generally recognized pharmacopeia for use in animals, including humans as well as non-human mammals. The term "carrier" refers to a diluent, adjuvant, excipient, or vehicle with which the pharmaceutical composition is administered. Water, saline solutions and aqueous dextrose and glycerol solutions can be employed as liquid carriers, particularly for injectable solutions. Examples of suitable pharmaceutical carriers are described in "Remington's Pharmaceutical Sciences" by E. W. Martin. The formulation should suit the mode of administration.

The immunogenic compositions of the present invention can further comprise one or more additional "immunomodulators," which are agents that perturb or alter the immune system, such that either up-regulation or down-regulation of humoral and/or cell-mediated immunity is observed. In one embodiment, up-regulation of the humoral and/or cell-mediated arms of the immune system is provided. Examples of certain immunomodulators include, e.g., an adjuvant or cytokine, or Iscomatrix® (CSL Limited; Parkville, Australia), described in U.S. Pat. No. 5,254,339 among others. Non-limiting examples of adjuvants that can be used in the immunogenic composition of the present invention include the RIBI adjuvant system (Ribi Inc.; Hamilton, Mont.), alum, mineral gels such as aluminum hydroxide gel, oil-in-water emulsions, water-in-oil emulsions such as, e.g., Freund's complete and incomplete adjuvants, Block copolymer (CytRx; Atlanta, Ga.), QS-21 (Cambridge Biotech Inc.; Cambridge, Mass.), SAF-M (Chixon; Emeryville, Calif.), Amphigen® adjuvant, saponin, Quil A or other saponin fraction, monophosphoryl lipid A, and Avridine lipid-amine adjuvant. Non-limiting examples of oil-in-water emulsions useful in the immunogenic composition of the invention include modified SEAM62 and SEAM 1/2 formulations. Modified SEAM62 is oil-in-water emulsion containing 5% (v/v) squalene (Sigma), 1% (v/v) Span® 85 Detergent (ICI Surfactants), 0.7% (v/v) polysorbate 80 detergent (ICI Surfactants), 2.5% (v/v) ethanol, 200 mcg/ml Quil A, 100 mcg/ml cholesterol, and 0.5% (v/v) lecithin. Modified SEAM 1/2 is an oil-in-water emulsion comprising 5% (v/v) squalene, 1% (v/v) Span® 85 Detergent, 0.7% v/v) polysorbate 80 detergent, 2.5% (v/v) ethanol, 100 mcg/ml Quil A, and 50 mcg/ml cholesterol. Other "immunomodulators" that can be included in the immunogenic composition include, e.g., one or more interleukins, interferons, or other known cytokines or chemokines. In one embodiment, the adjuvant may be a cyclodextrin derivative or a polyanionic polymer, such as those described in U.S. Pat. Nos. 6,165,995 and 6,610,310, respectively. It is to be understood that the immunomodulator and/or adjuvant to be used will depend on the subject to which the immunogenic composition will be administered, the route of injection and the number of injections to be given.

The immunogenic compositions of the invention may further comprise one or more preservatives in addition to a plurality of staphylococcal capsular polysaccharide-protein conjugates. The FDA requires that biological products in multiple-dose (multi-dose) vials contain a preservative, with only a few exceptions. Vaccine products containing preservatives include vaccines containing benzethonium chloride (anthrax), 2-phenoxyethanol (DTaP, HepA, Lyme, Polio (parenteral)), phenol (Pneumo, Typhoid (parenteral), Vaccinia) and thimerosal (DTaP, DT, Td, HepB, Hib, Influenza, JE, Mening, Pneumo, Rabies). Preservatives approved for use in injectable drugs include, chlorobutanol, m-cresol, methylparaben, propylparaben, 2-phenoxyethanol, benzethonium chloride, benzalkonium chloride, benzoic, acid, benzyl alcohol, phenol, thimerosal and phenylmercuric nitrate.

Formulations of the invention may further comprise one or more of a buffer, a salt, a divalent cation, anon-ionic detergent, a cryoprotectant such as a sugar, and an anti-oxidant such as a free radical scavenger or chelating agent, or any multiple combination thereof. The choice of any one component, e.g., a chelator, may determine whether or not another component (e.g., a scavenger) is desirable. The final composition formulated for administration should be sterile and/or pyrogen free. The skilled artisan may empirically determine which combinations of these and other components will be optimal for inclusion in the preservative containing immunogenic compositions of the invention depending on a variety of factors such as the particular storage and administration conditions required.

In certain embodiments, a formulation of the invention which is compatible with parenteral administration comprises one or more physiologically acceptable buffers selected from, but not limited to, Tris (trimethamine), phosphate, acetate, borate, citrate, glycine, histidine and succinate. In certain embodiments, the formulation is buffered to within a pH range of about 6.0 to about 9.0, preferably from about 6.4 to about 7.4.

In certain embodiments, it may be desirable to adjust the pH of the immunogenic composition or formulation of the invention. The pH of a formulation of the invention may be adjusted using standard techniques in the art. The pH of the formulation may be adjusted to be between 3.0 and 8.0. In certain embodiments, the pH of the formulation may be, or may adjusted to be, between 3.0 and 6.0, 4.0 and 6.0, or 5.0 and 8.0. In other embodiments, the pH of the formulation may be, or may adjusted to be, about 3.0, about 3.5, about 4.0, about 4.5, about 5.0, about 5.5, about 5.8, about 6.0, about 6.5, about 7.0, about 7.5, or about 8.0. In certain embodiments, the pH may be, or may adjusted to be, in a range from 4.5 to 7.5, or from 4.5 to 6.5, from 5.0 to 5.4, from 5.4 to 5.5, from 5.5 to 5.6, from 5.6 to 5.7, from 5.7 to 5.8, from 5.8 to 5.9, from 5.9 to 6.0, from 6.0 to 6.1, from 6.1 to 6.2, from 6.2 to 6.3, from 6.3 to 6.5, from 6.5 to 7.0, from 7.0 to 7.5 or from 7.5 to 8.0. In a specific embodiment, the pH of the formulation is about 5.8.

In certain embodiments, a formulation of the invention which is compatible with parenteral administration comprises one or more divalent cations, including but not limited to $MgCl_2$, $CaCl_2$ and $MnCl_2$, at a concentration ranging from about 0.1 mM to about 10 mM, with up to about 5 mM being preferred.

In certain embodiments, a formulation of the invention which is compatible with parenteral administration comprises one or more salts, including but not limited to sodium chloride, potassium chloride, sodium sulfate, and potassium sulfate, present at an ionic strength which is physiologically acceptable to the subject upon parenteral administration and included at a final concentration to produce a selected ionic strength or osmolarity in the final formulation. The final ionic strength or osmolality of the formulation will be determined by multiple components (e.g., ions from buffering compound(s) and other non-buffering salts. A preferred salt, NaCl, is present from a range of up to about 250 mM with salt concentrations being selected to complement other components (e.g., sugars) so that the final total osmolarity of the formulation is compatible with parenteral administration (e.g., intramuscular or subcutaneous injection) and will promote long term stability of the immunogenic components of the immunogenic composition formulation over various temperature ranges. Salt-free formulations will tolerate increased ranges of the one or more selected cryoprotectants to maintain desired final osmolarity levels.

In certain embodiments, a formulation of the invention which is compatible with parenteral administration comprises one or more cryoprotectants selected from but not limited to disaccharides (e.g., lactose, maltose, sucrose or trehalose) and polyhydroxy hydrocarbons (e.g., dulcitol, glycerol, mannitol and sorbitol).

In certain embodiments, the osmolarity of the formulation is in a range of from about 200 mOs/L to about 800 mOs/L, with a preferred range of from about 250 mOs/L to about 500 mOs/L, or about 300 mOs/L-about 400 mOs/L. A salt-free formulation may contain, for example, from about 5% to about 25% sucrose, and preferably from about 7% to about 15%, or about 10% to about 12% sucrose. Alternatively, a salt-free formulation may contain, for example, from about 3% to about 12% sorbitol, and preferably from about 4% to 7%, or about 5% to about 6% sorbitol. If salt such as sodium chloride is added, then the effective range of sucrose or sorbitol is relatively decreased. These and other such osmolality and osmolarity considerations are well within the skill of the art.

In certain embodiments, a formulation of the invention which is compatible with parenteral administration comprises one or more free radical oxidation inhibitors andior chelating agents. A variety of free radical scavengers and chelators are known in the art and apply to the formulations and methods of use described herein. Examples include but are not limited to ethanol, EDTA, a EDTA/ethanol combination, triethanolamine, mannitol, histidine, glycerol, sodium citrate, inositol hexaphosphate, tripotyphosphate, ascorbic acid/ascorbate, succinic acid/succinate, malic acid/maleate, desferal, EDDHA and DTPA, and various combinations of two or more of the above. In certain embodiments, at least one non-reducing free radical scavenger may be added at a concentration that effectively enhances long term stability of the formulation. One or more free radical oxidation inhibitors/chelators may also be added in various combinations, such as a scavenger and a divalent cation. The choice of chelator will determine whether or not the addition of a scavenger is needed.

In certain embodiments, a formulation of the invention which is compatible with parenteral administration comprises one or more non-ionic surfactants, including but not limited to polyoxyethylene sorbitan fatty acid esters, Polysorbate-80 (Tween 80), Polysorbate-60 (Tween 60), Polysorbate-40 (Tween 40) and Polysorbate-20 (Tween 20), polyoxyethylene alkyl ethers, including but not limited to Brij 58, Brij 35, as well as others such as Triton X-100; Triton X-114, NP40, Span 85 and the Pluronic series of non-ionic surfactants (e. g., Plutonic 121), with preferred components Polysorbate-80 at a concentration from about 0.001% to about 2% (with up to about 0.25% being preferred) or Polysorbate-40 at a concentration from about 0.001% to 1% (with up to about 0.5% being preferred).

In certain embodiments, a formulation of the invention comprises one or more additional stabilizing agents suitable for parenteral administration, e.g., a reducing agent comprising at least one thiol (—SH) group (e.g., cysteine, N-acetyl cysteine, reduced glutathione, sodium thioglycolate, thiosulfate, monothioglycerol, or mixtures thereof). Alternatively or optionally, preservative-containing immunogenic composition formulations of the invention may be further stabilized by removing oxygen from storage containers, protecting the formulation from light (e.g., by using amber glass containers).

Preservative-containing immunogenic composition formulations of the invention may comprise one or more pharmaceutically acceptable carriers or excipients, which includes any excipient that does not itself induce an immune response. Suitable excipients include but are not limited to macromolecules such as proteins, saccharides, polylactic acids, polyglycolic acids, polymeric amino acids, amino acid copolymers, sucrose (Paoletti et al, 2001, *Vaccine,* 19:2118), trehalose, lactose and lipid aggregates (such as oil droplets or liposomes). Such carriers are well known to the skilled artisan. Pharmaceutically acceptable excipients are discussed, e.g., in Gennaro, 2000, Remington: The Science and Practice of Pharmacy, 20$^{th}$ edition, ISBN:0683306472.

Compositions of the invention may be lyophilized or in aqueous form, i.e. solutions or suspensions. Liquid formulations may advantageously be administered directly from their packaged form and are thus ideal for injection without the need for reconstitution in aqueous medium as otherwise required for lyophilized compositions of the invention.

Direct delivery of immunogenic compositions of the present invention to a subject may be accomplished by parenteral administration (intramuscularly, intraperitoneally, intradermally, subcutaneously, intravenously, or to the interstitial space of a tissue); or by rectal, oral, vaginal, topical, transdermal, intranasal, ocular, aural, pulmonary or other mucosal administration. In a preferred embodiment, parenteral administration is by intramuscular injection, e.g., to the thigh or upper arm of the subject. Injection may be via a needle (e.g. a hypodermic needle), but needle free injection may alternatively be used. A typical intramuscular dose is 0.5 mL. Compositions of the invention may be prepared in various forms, e.g., for injection either as liquid solutions or suspensions. In certain embodiments, the composition may be prepared as a powder or spray for pulmonary administration, e.g. in an inhaler. In other embodiments, the composition may be prepared as a suppository or pessary, or for nasal, aural or ocular administration, e.g. as a spray, drops, gel or powder.

The amount of conjugate in each immunogenic composition dose is selected as an amount that induces an immunoprotective response without significant, adverse effects. Such amount can vary depending upon the staphylococcal serotype. Generally, each dose will comprise 0.1 to 100 μg of polysaccharide, particularly 0.1 to 10 μg, and more particularly 1 to 5 μg.

Optimal amounts of components for a particular immunogenic composition may be ascertained by standard studies involving observation of appropriate immune responses in subjects. Following an initial vaccination, subjects can receive one or several booster immunizations adequately spaced.

Packaging and Dosage Forms

Immunogenic compositions of the invention may be packaged in unit dose or multi-dose form (e.g. 2 doses, 4 doses, or more). For multi-dose forms, vials are typically but not necessarily preferred over pre-filled syringes. Suitable multi-dose formats include but are not limited to: 2 to 10 doses per container at 0.1 to 2 mL per dose. In certain embodiments, the dose is a 0.5 mL dose. See, e.g., International Patent Application WO2007/127668, which is incorporated by reference herein.

Compositions may be presented in vials or other suitable storage containers, or may be presented in pre-filled delivery devices, e.g., single or multiple component syringes, which may be supplied with or without needles. A syringe typically but need not necessarily contains a single dose of the preservative-containing immunogenic composition of the invention, although multi-dose, pre-filled syringes are also envisioned. Likewise, a vial may include a single dose but may alternatively include multiple doses.

Effective dosage volumes can be routinely established, but a typical dose of the composition for injection has a volume of 0.5 mL. In certain embodiments, the dose is formulated for administration to a human subject. In certain embodiments, the dose is formulated for administration to an adult, teen, adolescent, toddler or infant (i.e., no more than one year old) human subject and may in preferred embodiments be administered by injection.

Liquid immunogenic compositions of the invention are also suitable for reconstituting other immunogenic compositions which are presented in lyophilized form. Where an immunogenic composition is to be used for such extemporaneous reconstitution, the invention provides a kit with two or more vials, two or more ready-filled syringes, or one or more of each, with the contents of the syringe being used to reconstitute the contents of the vial prior to injection, or vice versa.

Alternatively, immunogenic compositions of the present invention may be lyophilized and reconstituted, e.g., using one of a multitude of methods for freeze drying well known in the art to form dry, regular shaped (e.g., spherical) particles, such as micropellets or microspheres, having particle characteristics such as mean diameter sizes that may be selected and controlled by varying the exact methods used to prepare them. The immunogenic compositions may further comprise an adjuvant which may optionally be prepared with or contained in separate dry, regular shaped (e.g., spherical) particles such as micropellets or microspheres. In such embodiments, the present invention further provides an immunogenic composition kit comprising a first component that includes a stabilized, dry immunogenic composition, optionally further comprising one or more preservatives of the invention, and a second component comprising a sterile, aqueous solution for reconstitution of the first component. In certain embodiments, the aqueous solution comprises one or more preservatives, and may optionally comprise at least one adjuvant (see, e.g., WO2009/109550 (incorporated herein by reference).

In yet another embodiment, a container of the multi-dose format is selected from one or more of the group consisting of, but not limited to, general laboratory glassware, flasks, beakers, graduated cylinders, fermentors, bioreactors, tubings, pipes, bags, jars, vials, vial closures (e.g., a rubber stopper, a screw on cap), ampoules, syringes, dual or multi-chamber syringes, syringe stoppers, syringe plungers, rubber closures, plastic closures, glass closures, cartridges and disposable pens and the like. The container of the present invention is not limited by material of manufacture, and includes materials such as glass, metals (e.g., steel, stainless steel, aluminum, etc.) and polymers (e.g., thermoplastics, elastomers, thermoplastic-elastomers). In a particular embodiment, the container of the format is a 5 mL Schott Type I glass vial with a butyl stopper. The skilled artisan will appreciate that the format set forth above is by no means an exhaustive list, but merely serve as guidance to the artisan with respect to the variety of formats available for the present invention. Additional formats contemplated for use in the present invention may be found in published catalogues from laboratory equipment vendors and manufacturers such as United States Plastic Corp. (Lima, Ohio), VWR.

Methods for Making Immunogenic Conjugates

The present invention also includes methods of making the immunogenic conjugates described herein. Methods for making the immunogenic conjugates of the invention involve covalent conjugation of the capsular polysaccharides with the carrier proteins using conjugation chemistry involving CDI (1,1-carbonyldiimidazole), CDT (1,1-carboyl-di-1,2,4-triazole) or PDPH (3-(2-pyridyldithio)-propionyl hydrazide).

Accordingly, one embodiment of the invention provides a CDT-based method of making an immunogenic conjugate comprising a S. aureus serotype 5 or 8 capsular polysaccharide conjugated to a carrier protein, the method comprising the steps of: a) compounding a S. aureus serotype 5 or 8 capsular polysaccharide with imidazole or triazole to produce a compounded polysaccharide; b) reacting the compounded polysaccharide with CDT in an organic solvent and about 0.1% to about 0.3% w/v water to produce an activated serotype 5 or 8 capsular polysaccharide; c) purifying the activated serotype 5 or 8 capsular polysaccharide to produce a purified activated serotype 5 or 8 capsular polysaccharide; d) reacting the purified activated serotype 5 or 8 capsular polysaccharide with a carrier protein in the organic solvent to produce a serotype 5 or 8 capsular polysaccharide:carrier protein conjugate; and e) hydrolyzing the serotype 5 or 8 capsular polysaccharide:carrier protein conjugate to remove unreacted activation groups; whereby an immunogenic conjugate comprising a S. aureus serotype 5 or 8 capsular polysaccharide conjugated to a carrier protein is produced. In one embodiment, prior to step (d), the purified activated serotype 5 or 8 capsular polysaccharide is compounded with a carrier protein.

In one embodiment of the invention, another CDT-based method of making an immunogenic conjugate is provided comprising a S. aureus serotype 5 or 8 capsular polysaccharide conjugated to a carrier protein, the method comprising the steps of: a) compounding a S. aureus serotype 5 or 8 capsular polysaccharide with imidazole or triazole to produce a compounded polysaccharide; b) reacting the compounded polysaccharide with CDT in an organic solvent and about 0.1% to about 0.3% w/v water to produce an activated serotype 5 or 8 capsular polysaccharide; c) reacting the activated serotype 5 or 8 capsular polysaccharide with a carrier protein in the organic solvent to produce a serotype 5 or 8 capsular polysaccharide:carrier protein conjugate; and d) hydrolyzing the serotype 5 or 8 capsular polysaccharide:carrier protein conjugate to remove unreacted activation groups; whereby an immunogenic conjugate comprising a S. aureus serotype 5 or 8 capsular polysaccharide conjugated to a carrier protein is produced.

In one embodiment, the organic solvent within the CDT-based methods of making an immunogenic conjugate is a polar aprotic solvent. In one embodiment, the organic solvent is a polar aprotic solvent selected from the group consisting of dimethyl sulfoxide (DMSO), dimethylformamide (DMF), dimethylacetamide, N-methyl-2-pyrrolidone, and hexamethylphosphoramide (HMPA). In one embodiment, the organic solvent is DMSO.

In one embodiment, the step of reacting the compounded polysaccharide with CDT within the CDT-based methods of making an immunogenic conjugate comprises providing about 20-fold molar excess of CDT compared to the polysaccharide.

In one embodiment, the step of purifying the activated serotype 5 or 8 capsular polysaccharide within the CDT-based methods of making an immunogenic conjugate comprises diafiltration.

In one embodiment, the carrier protein within the CDT-based methods of making an immunogenic conjugate is $CRM_{197}$. In one embodiment, the activated serotype 5 or 8 capsular polysaccharide within the methods of making an immunogenic conjugate is reacted with the $CRM_{197}$ in a ratio by weight of about 1:1.

In one embodiment, the step of hydrolyzing the serotype 5 or 8 polysaccharide:carrier protein conjugate to remove unreacted activation groups within the CDT-based methods of making an immunogenic conjugate comprises dilution into a buffer and maintaining a pH of about 8.8 to about 9.2 for at least 4 hours at about 20° C. to about 26° C. In one embodiment, the step of hydrolyzing the serotype 5 or 8 capsular polysaccharide:carrier protein conjugate comprises dilution into a buffer and maintaining a pH of about 9.0 for at least 4 hours at about 23° C.

In one embodiment, the serotype 5 or 8 capsular polysaccharide:carrier protein conjugate produced according to the CDT-based methods of making an immunogenic conjugate is purified. In one embodiment, purification of the serotype 5 or 8 capsular polysaccharide:carrier protein conjugate comprises diafiltration.

In one embodiment, prior to reacting the compounded polysaccharide with CDT within the CDT-based methods of making an immunogenic conjugate, the compounded serotype 5 or 8 polysaccharide is lyophilized and resuspended. In one embodiment, both the compounded polysaccharide and the carrier protein are separately lyophilized and re-suspended prior to reacting the compounded polysaccharide with CDT. In one embodiment, the lyophilized compounded polysaccharide and/or the lyophilized carrier protein are resuspended in an organic solvent. In one embodiment, the organic solvent is DMSO.

In one embodiment, prior to reacting the activated serotype 5 or 8 capsular polysaccharide compounded with a carrier protein within the CDT-based method of making an immunogenic conjugate, the purified activated serotype 5 or 8 capsular polysaccharide and the carrier protein are separately lyophilized and re-suspended. In one embodiment, the carrier protein is $CRM_{197}$ and prior to lyophilization the $CRM_{197}$ is diafiltered against NaCl. In one embodiment, prior to lyophilization the $CRM_{197}$ is diafiltered against NaCl and the w/w ratio of NaCl/CRM is adjusted to about 0.5 to about 1.5.

One embodiment of the present invention provides a PDPH-based method of making an immunogenic conjugate comprising a S. aureus serotype 5 or 8 capsular polysaccharide conjugated to a carrier protein, the method comprising the steps of: a) reacting a S. aureus serotype 5 or 8 capsular polysaccharide with PDPH and a carbodiimide an organic solvent to produce a PDPH-linked polysaccharide; b) reacting the PDPH-linked polysaccharide with a reducing agent to produce an activated polysaccharide; c) purifying the activated serotype 5 or 8 capsular polysaccharide to produce a purified activated serotype 5 or 8 capsular polysaccharide; d) reacting a carrier protein with a bromoacetic acid in an organic solvent to produce an activated carrier protein; e) purifying the activated carrier protein to produce a purified activated carrier protein; f) reacting the purified activated serotype 5 or 8 capsular polysaccharide with the purified activated carrier protein to produce a serotype 5 or 8 capsular polysaccharide:carrier protein conjugate; and g) hydrolyzing the serotype 5 or 8 capsular polysaccharide:carrier protein conjugate to remove unreacted activation groups; whereby an immunogenic conjugate comprising a S. aureus serotype 5 or 8 capsular polysaccharide conjugated to a carrier protein is produced.

In one embodiment, the bromoacetic acid used within the PDPH-based methods of making an immunogenic conjugate is a N-hydroxysuccinimide ester of bromoacetic acid (BAANS). In one embodiment, the carrier protein used within the PDPH-based methods of the invention is $CRM_{197}$ and the BAANS is added in a $CRM_{197}$:BAANS ratio by weight of about 1:0.1 to about 1:0.5.

In one embodiment, the organic solvent within the PDPH-based methods of making an immunogenic conjugate is a polar aprotic solvent. In one embodiment, the organic solvent is a polar aprotic solvent selected from the group consisting of DMSO, DMF, dimethylacetamide, N-methyl-2-pyrrolidone, and HMPA. In one embodiment, the organic solvent is DMSO.

In one embodiment, the carbodiimide used within the PDPH-based methods of making an immunogenic conjugate is 1-Ethyl-3-(3-dimethylaminopropyl)-carbodiimide (EDAC). In one embodiment, the step of reacting the serotype 5 or 8 capsular polysaccharide with PDPH and EDAC in an organic solvent comprises maintaining a polysaccharide:PDPH:EDAC ratio by weight of about 1:5:3.

In one embodiment, the reducing agent used within the PDPH-based methods of making an immunogenic conjugate is dithiothreitol (DTT).

In one embodiment, the steps of purifying the activated serotype 5 or 8 capsular polysaccharide and purifying the carrier protein within the PDPH-based methods of making an immunogenic conjugate each comprise diafiltration.

In one embodiment, the carrier protein within the PDPH-based methods of making an immunogenic conjugate is $CRM_{197}$. In one embodiment, the activated serotype 5 or 8 polysaccharide within the methods of making an immunogenic conjugate is reacted with the $CRM_{197}$ in a ratio by weight of about 1:1.

In one embodiment, the step of hydrolyzing the serotype 5 or 8 polysaccharide:carrier protein conjugate to remove unreacted activation groups within the PDPH-based methods of making an immunogenic conjugate comprises the addition of cysteamine hydrochloride.

In one embodiment, the serotype 5 or 8 capsular polysaccharide:carrier protein conjugate produced according to the PDPH-based methods of making an immunogenic conjugate is purified. In one embodiment, purification of the serotype 5 or 8 capsular polysaccharide:carrier protein conjugate comprises diafiltration.

In one embodiment, prior to reacting the purified activated serotype 5 or 8 capsular polysaccharide with the purified activated carrier protein within the PDPH-based methods of making an immunogenic conjugate, both the purified activated polysaccharide and the purified activated carrier protein are separately lyophilized and re-suspended. In one embodiment, the lyophilized activated polysaccharide and/or the lyophilized activated carrier protein are resuspended in an organic solvent. In one embodiment, the organic solvent is DMSO.

As used herein, "lyophilization" means a dehydration process in which the bacterial capsular polysaccharide is frozen while the surrounding pressure is reduced in the presence of enough heat to allow frozen water to sublime directly from a solid phase to gas phase. Any method known in the art for lyophilizing polysaccharides can be used. See, e.g., Harris & Angal (1989) "Protein Purification Methods," In: Kennedy & Cabral, eds. "Recovery Processes for Biological Materials" (John Wiley & Sons; 1993); U.S. Pat. No. 4,134,214; and Int'l Patent Application Publication No. WO 2003/086471; each of which is incorporated herein by reference as if set forth in its entirety. Optionally, a cryoprotectant can be included during lyophilization, such as for example sucrose, glucose, lactose, trehalose, arabinose, xylose, galactose, sorbitol or mannitol.

As used herein, "activate" and "activation" means that a bacterial capsular polysaccharide or carrier protein is modified in such a way that it is rendered amenable to conjugation (i.e., at least one moiety must be rendered capable of covalently bonding to the carrier molecule). For example, with respect to CDT-based conjugation methods of the present invention, the polysaccharide is activated in a low moisture environment (e.g., in DMSO) to form triazole carbamate moieties with available hydroxyls and acyltriazole moieties with carboxylic acids. Activated polysaccharides may then be reacted with $CRM_{197}$ protein, which leads to the nucleophilic displacement of the triazole by lysine residues within $CRM_{197}$ and formation of a carbamate linkage (for activated hydroxyls) and the amide linkage (for activated carboxylic acids). By contrast, with respect to the PDPH-based conjugation methods of the present invention, both the carrier proteins and the polysaccharides are activated prior to conjugation: 1) activation of $CRM_{197}$ involves introducing bromoacetyl groups into the $CRM_{197}$ protein by reaction of amine groups with the N-hydroxysuccimide ester of bromoacetic acid; and 2) activation of polysaccharide involves coupling the carbodiimide-activated carboxylate groups of N-acetylmannosaminouronic acid in the polysaccharide to the hydrazide group of the sulfhydryl-reactive hydrazide heterobifunctional linker PDPH, followed by reduction with DTT. Activated polysaccharides may then be reacted with activated carrier protein such that thiols of PDPH-thiolated polysaccharides react with bromoacetyl groups of activated carrier protein resulting in a covalent thioether linkage formed by bromide displacement.

According to the methods of the invention, the capsular polysaccharides, carrier proteins, and/or polysaccharide-protein conjugates may be purified. Any method known in the art for purifying polysaccharides or proteins can be used, such as concentration/diafiltration, precipitation/elution, column chromatography and depth filtration. See, Farrés et al. (1996) Biotechnol. Tech. 10:375-380; Gonçalves et al. In: Communicating Current Research and Educational Topics and Trends in Applied Microbiology (Antonio Mendez Vilas, ed. 1$^{st}$ ed, Badajoz, Espanha: Formatex; 2007. pp. 450-457); Tanizaki et al. (1996) J. Microbiol. Methods 27:19-23; and U.S. Pat. No. 6,146,902; and US Patent Application Publication No. 2008/0286838; each of which is incorporated herein by reference as if set forth in its entirety.

As used herein, the term "isolated" or "purified" means that the material is removed from its original environment (e.g., the natural environment if it is naturally occurring or from its host organism if it is a recombinant entity, or taken from one environment to a different environment). For example, an isolated polysaccharide, peptide or protein is substantially free of cellular material or other contaminating proteins from the cell or tissue source from which the protein is derived, or substantially free of chemical precursors or other chemicals when chemically synthesized or otherwise present in a mixture as part of a chemical reaction. In the present invention, the protein or polysaccharide can be isolated from the bacterial cell or from cellular debris, so that they are provided in a form useful in the manufacture of an immunogenic composition. The term "isolated" or "isolating" may include purifying, or purification, including for example, the methods of purification of the capsular polysaccharides, as described herein. The language "substantially free of cellular material" includes preparations of a polysaccharide/polypeptide/protein in which the polysaccharide/polypeptide/protein is separated from cellular components of the cells from which it is isolated or recombinantly produced. Thus, a polypeptide/protein, polysaccharide, or conjugate that is substantially free of cellular material or other compounds includes preparations of the polypeptide/protein, polysaccharide, or conjugate having less than about 30%, 20%, 10%, 5%, 2.5% or 1% (by dry weight) of contaminating protein, polysaccharide, or other compounds. When the polypeptide/protein is recombinantly produced, it is also preferably substantially free of culture medium, i.e., culture medium represents less than about 20%, 10%, 5%, 4%, 3%, 2%, or 1% of the volume of the protein preparation. When polypeptide/protein or polysaccharide is produced by chemical synthesis, it is preferably substantially free of chemical precursors or other chemicals, i.e., it is separated from chemical precursors or other chemicals which are involved in the synthesis of the protein or polysaccharide. Accordingly, such preparations of the polypeptide/protein or polysaccharide have less than about 30%, 20%, 10%, 5%, 4%, 3%, 2%, or 1% (by dry weight) of chemical precursors or compounds other than polypeptide/protein or polysaccharide fragment of interest.

Immunogenic conjugates produced by any of the methods described herein may be stored in water or a low ionic strength neutral pH buffer or lyophilized into a dry powder.

Methods for Inducing an Immune Response and Protecting Against S. Aureus Infection The present invention also includes methods of use for immunogenic compositions described herein. For example, one embodiment of the invention provides a method of inducing an immune response against S. aureus comprising administering to a subject an immunogenic amount of any of the immunogenic compositions described herein. One embodiment of the invention provides a method of protecting a subject against an infection with S. aureus, or a method of preventing infection with S. aureus, or a method of reducing the severity of or delaying the onset of at least one symptom associated with an infection caused by S. aureus, the methods comprising administering to a subject an immunogenic amount of any of the immunogenic compositions described herein. One embodiment of the invention provides a method of treating or preventing a Staphylococcal infection, disease or condition associated with a Staphylococcus sp. in a subject, the method comprising the step of administering a therapeutically or prophylactically effective amount of an immunogenic composition described herein to the subject. In some embodiments, the method of treating or preventing a Staphylococcal infection, disease or conditions comprises human, veterinary, animal, or agricultural treatment. Another embodiment provides a method of treating or preventing a Staphylococcal infection, disease or condition associated with a Staphylococcus sp. in a subject, the method comprising generating a polyclonal or monoclonal antibody preparation from the immunogenic composition described herein, and using said antibody preparation to confer passive immunity to the subject. One embodiment of the invention provides a method of preventing a Staphylococcal infection in a subject undergoing a surgical procedure, the method comprising the step of administering a prophylactically effective amount of an immunogenic composition described herein to the subject prior to the surgical procedure.

An "immune response" to an antigen or immunogenic composition is the development in a subject of a humoral and/or a cell-mediated immune response to molecules present in the antigen or vaccine composition of interest. For purposes of the present invention, a "humoral immune response" is an antibody-mediated immune response and involves the induction and generation of antibodies that recognize and bind with some affinity for the antigen in the immunogenic composition of the invention, while a "cell-mediated immune response" is one mediated by T-cells and/or other white blood cells. A "cell-mediated immune response" is elicited by the presentation of antigenic epitopes in association with Class I or Class II molecules of the major histocompatibility complex (MHC), CD1 or other non-classical MHC-like molecules. This activates antigen-specific CD4+ T helper cells or CD8+ cytotoxic lymphocyte cells ("CTLs"). CTLs have specificity for peptide antigens that are presented in association with proteins encoded by classical or non-classical MHCs and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide or other antigens in association with classical or non-classical MHC molecules on their surface. A "cell-mediated immune response" also refers to the production of cytokines, chemokines and other such molecules produced by activated T-cells and/or other white blood cells, including those derived from CD4+ and CD8+ T-cells. The ability of a particular antigen or composition to stimulate a cell-mediated immunological response may be determined by a number of assays, such as by lymphoproliferation (lymphocyte activation) assays, CTL cytotoxic cell assays, by assaying for T-lymphocytes specific for the antigen in a sensitized subject, or by measurement of cytokine production by T cells in response to re-stimulation with antigen. Such assays are well known in the art. See, e.g., Erickson et al. (1993) J. Immunol. 151:4189-4199; and Doe et al. (1994) Eur. J. Immunol. 24:2369-2376.

As used herein, "treatment" (including variations thereof, e.g., "treat" or "treated") means any one or more of the following: (i) the prevention of infection or re-infection, as in a traditional vaccine, (ii) the reduction in the severity of, or, in the elimination of symptoms, and (iii) the substantial or complete elimination of the pathogen or disorder in question. Hence, treatment may be effected prophylactically (prior to infection) or therapeutically (following infection). In the present invention, prophylactic treatment is the preferred mode. According to a particular embodiment of the present invention, compositions and methods are provided that treat, including prophylactically and/or therapeutically immunize, a host animal against a microbial infection (e.g., a bacterium such as Staphylococcus). The methods of the present invention are useful for conferring prophylactic and/or therapeutic immunity to a subject. The methods of the present invention can also be practiced on subjects for biomedical research applications.

As used herein, "mammal" means a human or non-human animal. More particularly, mammal refers to any animal classified as a mammal, including humans, domestic and farm animals, and zoo, sports and pet companion animals such as a household pet and other domesticated animal including, but not limited to, cattle, sheep, ferrets, swine, horses, rabbits, goats, dogs, cats, and the like. Preferred companion animals are dogs and cats. Preferably, the mammal is human.

An "immunogenic amount," and "immunologically effective amount," both of which are used interchangeably herein, refers to the amount of antigen or immunogenic composition sufficient to elicit an immune response, either a cellular (T-cell) or humoral (B-cell or antibody) response, or both, as measured by standard assays known to one skilled in the art.

The amounts of a particular conjugate in a composition is generally calculated based on total polysaccharide, conjugated and non-conjugated for that conjugate. For example, a CP5 conjugate with 20% free polysaccharide will have about 80 mcg of conjugated CP5 polysaccharide and about 20 mcg of non-conjugated CP5 polysaccharide in a 100 mcg CP5 polysaccharide dose. The protein contribution to the conjugate is usually not considered when calculating the dose of a conjugate. The amount of conjugate can vary depending upon the staphylococcal serotype. Generally, each dose will comprise 0.1 to 100 mcg of polysaccharide, particularly 0.1 to 10 mcg, and more particularly 1 to 10 mcg. The "immunogenic amount" of the different polysaccharide components in the immunogenic composition, may diverge and each may comprise 1 mcg, 2 mcg, 3 mcg, 4 mcg, 5 mcg, 6 mcg, 7 mcg, 8 mcg, 9 mcg, 10 mcg, 15 mcg, 20 mcg, 30 mcg, 40 mcg, 50 mcg, 60 mcg, 70 mcg, 80 mcg, 90 mcg, or about 100 mcg of any particular polysaccharide antigen.

S. aureus "invasive disease" is the isolation of bacteria from a normally sterile site, where there is associated clinical signs/symptoms of disease. Normally sterile body sites include blood, CSF, pleural fluid, pericardial fluid, peritoneal fluid, joint/synovial fluid, bone, internal body site (lymph node, brain, heart, liver, spleen, vitreous fluid, kidney, pancreas, ovary) or other normally sterile sites. Clinical conditions characterizing invasive diseases include bacteremia, pneumonia, cellulitis, osteomyelitis, endocarditis, septic shock and more.

The effectiveness of an antigen as an immunogen, can be measured either by proliferation assays, by cytolytic assays, such as chromium release assays to measure the ability of a T-cell to lyse its specific target cell, or by measuring the levels of B-cell activity by measuring the levels of circulating antibodies specific for the antigen in serum. An immune response may also be detected by measuring the serum levels of antigen specific antibody induced following administration of the antigen, and more specifically, by measuring the ability of the antibodies so induced to enhance the opsonophagocytic ability of particular white blood cells, as described herein. The level of protection of the immune response may be measured by challenging the immunized host with the antigen that has been administered. For example, if the antigen to which an immune response is desired is a bacterium, the level of protection induced by the immunogenic amount of the antigen is measured by detecting the percent survival or the percent mortality after challenge of the animals with the bacterial cells. In one embodiment, the amount of protection may be measured by measuring at least one symptom associated with the bacterial infection, e.g., a fever associated with the infection. The amount of each of the antigens in the multi-antigen or multi-component vaccine or immunogenic compositions will vary with respect to each of the other components and can be determined by methods known to the skilled artisan. Such methods would include procedures for measuring immunogenicity and/or in vivo efficacy. In certain embodiments, the term "about" leans within 20%, preferably within 10%, and more preferably within 5%.

The invention further provides antibodies and antibody compositions which bind specifically and selectively to the serotype 5 or 8 capsular polysaccharides or immunogenic conjugates of the present invention. In some embodiments, antibodies are generated upon administration to a subject of the serotype 5 or 8 capsular polysaccharides or immunogenic conjugates of the present invention. In some embodiments, the invention provides purified or isolated antibodies directed against one or more of the serotype 5 or 8 capsular polysaccharides or immunogenic conjugates of the present invention. In some embodiments, the antibodies of the present invention are functional as measured by killing bacteria in either an animal efficacy model or via an opsonophagocytic killing assay. In some embodiments, the antibodies of the invention confer passive immunity to a subject. The present invention further provides polynucleotide molecules encoding an antibody or antibody fragment of the invention, and a cell, cell line (such as hybridoma cells or other engineered cell lines for recombinant production of antibodies) or a transgenic animal that produces an antibody or antibody composition of the invention, using techniques well-known to those of skill in the art.

Antibodies or antibody compositions of the invention may be used in a method of treating or preventing a Staphylococcal infection, disease or condition associated with a *Staphylococcus* sp. in a subject, the method comprising generating a polyclonal or monoclonal antibody preparation, and using said antibody or antibody composition to confer passive immunity to the subject. Antibodies of the invention may also be useful for diagnostic methods, e.g., detecting the presence of or quantifying the levels of CP5, CP8 or a conjugate thereof.

Several animal models known in the an may be used to assess the efficacy of any one of the immunogenic compositions described herein. For example:

Passive Murine Sepsis Model:

Mice are passively immunized intraperitoneally (i.p.) with immune IgG or monoclonal antibody. The mice are challenged 24 hours later with a lethal dose of *S. aureus*. The bacterial challenge is administered intravenously (i.v. or i.p.) ensuring that any survival could be attributed to the specific in vivo interaction of the antibody with the bacteria. The bacterial challenge dose is determined to be the dose required to achieve lethal sepsis of approximately 20% of the un-immunized control mice. Statistical evaluation of survival studies can be carried out by Kaplan-Meier analysis.

Active Immunization and Challenge Model:

In this model, mice are actively immunized subcutaneously (s.c.) with a target antigen at 0, 3 and 6 weeks (or a similar schedule known to those skilled in the art) and challenged with *S. aureus* at week 8 (or other similar schedule known to those skilled in the art) by the intravenous or intraperitoneal route. The bacterial challenge dose is calibrated to achieve approximately 20% survival in the control group over a 14 day period. Statistical evaluation of survival studies can be carried out by Kaplan-Meier analysis.

Passive Infectious Endocarditis Model:

A passive immunization model for infectious endocarditis (IE) caused by *S. aureus* has previously been used to show that ClfA can induce protective immunity. See, Vernachio et al. (2006) *Antmicro. Agents & Chemo.* 50:511-518. In this model of IE, rabbits or rats are used to simulate clinical infections that include a central venous catheter, bacteremia, and hematogenous seeding to distal organs. Catheterized rabbits or rats with sterile aortic valve vegetations are administered a single intravenous injection of a monoclonal or polyclonal antibody specific for the target antigen. After 24 hours, the animals are challenged i.v. with heterologous staphylococcal strains or a MRSA strain. Then 48 hours after challenge, cardiac vegetations, kidneys and blood are harvested and cultured. The frequency of staphylococcal infection in cardiac valve vegetations, kidneys, and blood is then measured. In one study, when animals were challenged with either MRSE ATCC 35984 or MRSA PFESA0003, significant reductions in infection rate were shown using either the polyclonal antibody preparation or the monoclonal antibody to ClfA. See, Vernachio et al., supra.

Passive Infectious Endocarditis Model:

The infectious endocarditis model has also been adapted for active immunization studies. Rabbits or rats are immunized intramuscularly (i.m.) with target antigen and challenged with aureus two weeks later via the i.v. route.

Pyelonephritis Model:

In the pyelonephritis model, mice are immunized on weeks 0, 3 and 6 (or a similar schedule known to those skilled in the art) with the target antigens. On week 8, the animals are challenged by, e.g., i.p. injection of, e.g., $1.7 \times 10^8$ cfu S. aureus PFESA0266. After 48 hours, the kidneys and/or other tissues are harvested and cultured. Finally, colony forming units of challenge bacteria are enumerated in the kidneys and/or other tissues. This model evaluates systemic dissemination in the animal.

Monitoring Functional Antibodies Using Opsonophagocytic Killing Assays

Differentiated effector cells from a cell line (e.g. HL60s) or polymorphonuclear cells (PMNs) isolated from donor human blood using LYMPHOLYTE®-poly solation (Cedarlane laboratories limited, Ontario, Canada) as per manufacturer's protocol can be used for this assay. Effector cells were resuspended in assay buffer (Modified Eagle's media containing 1% bovine serum albumin) at approximately $2 \times 10^7$ cells/ml concentration and placed in 37° C. incubator until ready to use. S. aureus strain PFESA0266 was grown overnight on tryptic soy agar plates. Bacterial cells were scraped, washed twice and resuspended in assay buffer containing 5% glycerol to an $OD_{600}=1$, which equals to approximately $5 \times 10^8$ cfu/ml concentration. One ml aliquots of the bacterial suspension were frozen and stored at −40° C. until ready to use. Frozen bacterial suspension were thawed and adjusted to a concentration of $10^6$ cfu/ml in assay buffer and placed on ice. The assay was performed using a sterile 96 deep well 1 ml polypropylene plates. Two fold serial dilutions of antibody samples (50 μl) were prepared and followed by addition of 300 μl of assay buffer to the antibody mix. Bacteria were added (50 μl) to the plates and placed on a rotary shaker at 4° C. for 30 minutes. The opsonization step was followed by addition of 50 μl of human complement (1% final concentration). Finally, 50 μl of effector cells ($10^7$ cells/ml concentration) were added to the plate and the suspension mixed well by repeated pipetting. A 50 μl aliquot of the suspension was 10 fold serially diluted in sterile 1% saponin solution, vortexed to minimize bacterial clumping and plated on tryptic soy agar in duplicate. The assay plate was incubated at 37° C. for 1 hour with continuous mixing using rotisserie style shaker. At the end of the incubation a 50 μl aliquot of suspension was 10 fold serially diluted in sterile 1% saponin solution, mixed by vortexing to minimize bacterial clumping and plated on tryptic soy agar in duplicate. The percentage killing was calculated by determining the ratio of the number of cfu surviving at 60 minutes in wells with bacteria, antibodies, complement and effector cells to the number of cfu surviving in tubes lacking antibodies but containing bacteria, complement and effector cells. Controls containing bacteria, complement, and sera were included to adjust for any reduction in cfu due to clumping.

Complement Adsorption

Serum from human donors adsorbed against S. aureus strains PFESA0266, PFESA0286 and PFESA0270 can be used as a source of complement in the assay. S. aureus strains were grown overnight on TSA plates at 37° C. Cells were scraped from the plate and resuspended in sterile PBS. Bacterial cells were centrifuged at 10,000 rpm for 10 minutes at 4° C. and cell pellet was resuspended in human serum for adsorption. Serum was incubated with bacteria on a nutator at 4° C. for 30 minutes. Cells were centrifuged, serum transferred to another tube containing bacteria and the adsorption step repeated again for 30 minutes. Finally, the cells were centrifuged and the serum passed through a 0.2 micron filter before 0.5 ml aliquots were frozen down in liquid nitrogen.

Method II—OPA Using HL-60 Cells

HL-60 cells were differentiated according to S. Romero-Steiner, et al., Clin Diagn Lab Immunol 4 (4) (1997), pp. 415-422. Harvested HL-60 cells were resuspended in assay buffer (Modified Eagle's media containing 1% bovine serum albumin) at approximately $10^8$ cells/nil and placed in 37° C. incubator until ready to use. S. aureus was grown overnight on tryptic soy agar plates. Bacterial cells were scraped, washed twice and resuspended in assay buffer containing 5% glycerol to an $OD_{600}=1$, which equals to approximately $5 \times 10^8$ cfu/ml. One ml aliquots of the bacterial suspension were frozen and stored at −40° C. until ready to use. Frozen bacterial suspension were thawed and adjusted to a concentration of $10^6$ cfu/ml in assay buffer and placed on ice. The assay was performed using a sterile 96 deep well 1 ml polypropylene plates. Two fold serial dilutions of monoclonal antibody samples (25 μl) were prepared and followed by addition of 150 μl of assay buffer to the antibody suspension. Bacteria were added (25 μl) to the plates and placed on a rotary shaker at 4° C. for 30 minutes followed by addition of 25 μl of human complement (1% final concentration). Finally, 25 μl of HL-60 cells ($10^7$ cells/ml) were added to the plate and the suspension mixed well by repeated pipetting. A 25 μl aliquot of the suspension was 10 fold serially diluted in sterile 1% saponin solution, mixed by vortexing to minimize bacterial clumping and plated on tryptic soy agar in duplicates. The assay plate was incubated at 37° C. for 1 hour with continuous mixing using rotisserie style shaker. At the end of incubation a 25 μl aliquot of suspension was 10 fold serially diluted in sterile 1% saponin solution, mixed by vortexing to and plated on tryptic soy agar in duplicate. The percentage killing was calculated by determining the ratio of the number of cfu surviving at 60 minutes in wells with bacteria, antibodies, complement and HL-60 cells to the number of cfu surviving in tubes lacking antibodies but containing bacteria, complement and HL-60 cells. Controls containing bacteria, complement and mAb was included to adjust for any reduction in cfu due to clumping.

The following examples are provided by way of illustration, not by way of limitation.

EXAMPLES

Example 1

Preparation of S. aureus Serotype 8 Capsular Polysaccharide

In this example, production of various size ranges of S. aureus serotype 8 capsular polysaccharide is described. The structure S. aureus serotype 8 capsular polysaccharide repeat unit is shown in FIG. 1. The methods described herein are effective in producing serotype 8 capsular polysaccharide with molecular weights ranging from about 20 kDa to 700 kDa. By proper selection of conditions, high molecular weight serotype 8 capsular polysaccharides can be isolated and purified ranging from 50 kDa to 700 kDa in molecular weight. For use in immunogenic compositions, serotype 8 capsular polysaccharide can be isolated and purified ranging from 70 kDa to 300 kDa in molecular weight and many desired ranges. Based on growth characteristics and the quantity of capsule produced, strains PFESA0005 or PFESA0286 were used for the production of serotype 8 capsular polysaccharide. Capsules isolated from strains PFESA0005 or PFESA0286 were shown to be identical.

For production of serotype 8 capsular polysaccharides, the strains were grown in a complex medium consisting primarily of a carbon source (either lactose or sucrose), hydrolyzed soyflour as the nitrogen source, and trace metals. The strains were grown in bioreactors for 2 to 5 days.

Prior to autoclaving, a sample was removed to test the level of Staphylococcal enterotoxin B (SEB) in the culture. In the presence of 0.05% polysorbate 80, the concentration of SEB in the fermentation was 15-20 ng/ml. Previous experiments showed that autoclaving the culture for 1 hour reduced the level of SEB to less than 0.1 ng/ml, which is below the limit of detection for the TECRA kit.

Diafiltered, ethanol-fractionated polysaccharide was loaded onto a Q-Sepharose AEC column and eluted with a linear gradient of NaCl as described above. Fractions were analyzed by the O-acetyl assay and double immunodifusion test for presence of serotype 5 polysaccharide and phosphate assay for the presence of teichoic acid (TA). The presence of serotype 8 polysaccharide was detected in fractions 35 to 95 (FIGS. 2A-B).

To reduce contamination with teichoic acid, fractions 35 to 75 were pooled and any residual teichoic acid was oxidized with sodium-metaperiodate to allow its removal by 3K diafiltration against $diH_2O$.

Purification of serotype 8 capsular polysaccharide used for the preparation of conjugates was performed by two different methods that rely on elevated temperature and low pH to affect the release of capsule from the cell and reduce the molecular weight of the polysaccharide. The resulting molecular weight depended on the time, temperature and pH of the hydrolysis step.

Characterization of serotype 8 capsular polysaccharide was performed using the techniques specified in Table 1.

TABLE 1

Characterization Assays for Purified S. aureus Serotype 8 Capsular Polysaccharides.

| Specificity | Assay |
| --- | --- |
| Residual Protein | Lowry colorimetric assay |
| Residual Nucleic acids | 260 nm scan |
| Residual Teichoic Acid | Phosphate colorimetric assay |
| Residual Peptidoglycan | HPAEC-PAD |
| Size | SEC-MALLS |
| Composition | HPAEC-PAD |
| Identity | 1H-NMR or reaction with specific mAb |
| O-acetylation | 1H-NMR |
| Concentration | MALLS-RI or HPAEC-PAD |

Capsule polysaccharides produced by the methods described below result in pure well characterized polysaccharides with low levels of protein, nucleic acid, peptidoglycan and teichoic acid contaminants.

In the first method, following release of the capsule polysaccharide from the cell and reduction of molecular weight, the preparation was treated with a cocktail of enzymes (e.g., ribonuclease, deoxyribonuclease, lysozyme and protease) to digest impurities. After incubation, residual impurities are precipitated by the addition of ethanol (final concentration about 25%). After removal of the residual ethanol, a solution containing capsule polysaccharide was loaded onto an anion exchange column (Q-Sepharose) and eluted with a linear salt gradient. Fractions containing capsule polysaccharide were pooled and treated with sodium meta-periodate. This treatment resulted in the oxidative hydrolysis of residual teichoic acid contaminant, but did not affect serotype 8 capsular polysaccharide. The reaction was quenched by the addition of ethylene glycol. The material was concentrated and diafiltered against $dH_2O$ to remove any residual reagents and by-products.

The second method was used to produce capsule polysaccharide without the use of enzymes to digest the various cell-derived impurities. In this method, following release of the capsule polysaccharide from the cell and reduction of molecular weight, the hydrolyzed fermentation broth was clarified by microfiltration followed by ultrafiltration and diafiltration. The solution was treated with activated carbon to remove impurities. After carbon treatment, the material was treated with sodium meta-periodate to oxidize residual teichoic acid followed by quenching with propylene glycol. The material was concentrated and diafiltered against $dH_2O$ to remove any residual reagents and by-products.

Preparations produced using either method resulted in pure capsular polysaccharides with low levels of protein, nucleic acid and teichoic acid contaminants. The methods described can be used to produce specific ranges of the desired high molecular weight polysaccharides by varying the conditions of hydrolysis. Examples of capsular polysaccharide obtainable by the methods described herein are shown in Table 2 below. Batches of purified serotype 8 capsular polysaccharide had high purity as indicated by no teichoic acid (TA), peptidoglycan and low residual protein. See, Table 2. The range of lower molecular weights spanned 20.4 kDa to 65.1 kDa, and the purified polysaccharides were highly O-acetylated (~100%). The levels of nucleic acid contamination were low (0.12-2.45%).

TABLE 2

Characterization of Serotype 8 Capsular Polysaccharide Preparations.

| Sample | Total CP8 Purified mg | MW (kDa) (g/mol) | Protein (Lowry) % (w/w) | Nuc. Acid (260 nm scan) % (w/w) | O-Acetyl NMR % |
| --- | --- | --- | --- | --- | --- |
| 1 | 310 | 27.0 | 1.2 | 0.94 | 100 |
| 2 | 438 | 29.0 | 2.4 | 2 | 100 |
| 3 | 179 | 20.4 | 0.37 | 0.12 | 108 |

Molecular Weight Selection a Capsular Polysaccharides:

A kinetic analysis demonstrated that a broad range of molecular weights of capsule polysaccharides can be generated by the methods described herein. Initially, larger polysaccharides were produced by the bacterial cells, and subsequently, a desired molecular weight range selected and then purified by manipulation of the pH and heat conditions of the heat and hydrolysis steps.

Heat treatment of S. aureus fermentation broth is a process step between fermentation and capsular polysaccharide recovery. This process step uses heat to treat pH-adjusted broth for a specified period. The goals of the heat treatment at low pH were to kill cells, inactivate enterotoxins, release cell bound polysaccharide and reduce molecular weight to the desired size. Among these goals, the reduction of molecular weight was the slowest in terms of processing time required in this step. Therefore, the other goals were inevitably achieved within the treatment time considered.

Heat Treatment:

pH and temperature conditions for selecting various molecular weight ranges of capsule polysaccharides were determined. A 15 L Biolafitte Fermenter was used for these studies. The fermentation broth was transferred to the fermenter by a peristaltic pump. Using an agitation speed of about 200 rpm, the broth pH was adjusted with concentrated sulfuric acid. Then, the broth temperature was raised to the set value. The heat treatment time started as soon as the temperature reached the set point. When the desired treatment time was reached, the broth was cooled to room temperature. In-process samples were taken to determine polysaccharide concentration and molecular weight by HPLC and SEC-MALLS systems, respectively. The molecular weight (MW) data was used in the kinetic analysis. The MW profiles were determined over time at pH 3.5, 4.0 and 5.0. See, FIG. 3A.

The kinetics of mild acid hydrolysis of polysaccharides was conducted using purified serotype 8 capsular polysaccharide obtained from the process. The purified polysaccharide solution was adjusted to the desired pH for the experiment with sulfuric acid. About 1.5 mL of the solution was transferred to each of the 15 mL centrifuge tubes. The tubes were placed in an oil bath equipped with a precision temperature control system. The tube was taken out at a predetermined time interval and was quenched in an ice bucket. At the end of the experiment, an aliquot of 1M Tris buffer (pH 7.5) was added to the sample to adjust the pH back to about 7. The samples were analyzed by a SEC-MALLS system. The MW data was used in the kinetic analysis. The effect of temperature on the MW profile of CP8 at pH 3.5 was determined over time. See, FIG. 3B.

Results

As shown in FIG. 3A, a lower pH was more effective in reducing the molecular weight of the polysaccharide. Molecular weights between 300 kDa and 600 kDa can be generated using a pH of 5 at 95° C. for between 15 minutes and 120 minutes. Likewise, molecular weights between 250 kDa and 450 kDa can be generated using a pH of 4 at 95° C. for between 15 minutes and 120 minutes. Moreover, molecular weights between 120 kDa and 450 kDa can be generated using a pH of 3.5 at 95° C. for between 15 minutes and 120 minutes.

As shown in FIG. 3B, the higher the temperature, the faster the rate of hydrolysis and broader the range of the molecular weights of polysaccharide produced with time. Use of a lower temperature, 55° C. versus 95° C. at the same pH, produces a narrower range of polysaccharide molecular weights.

Figure 4:
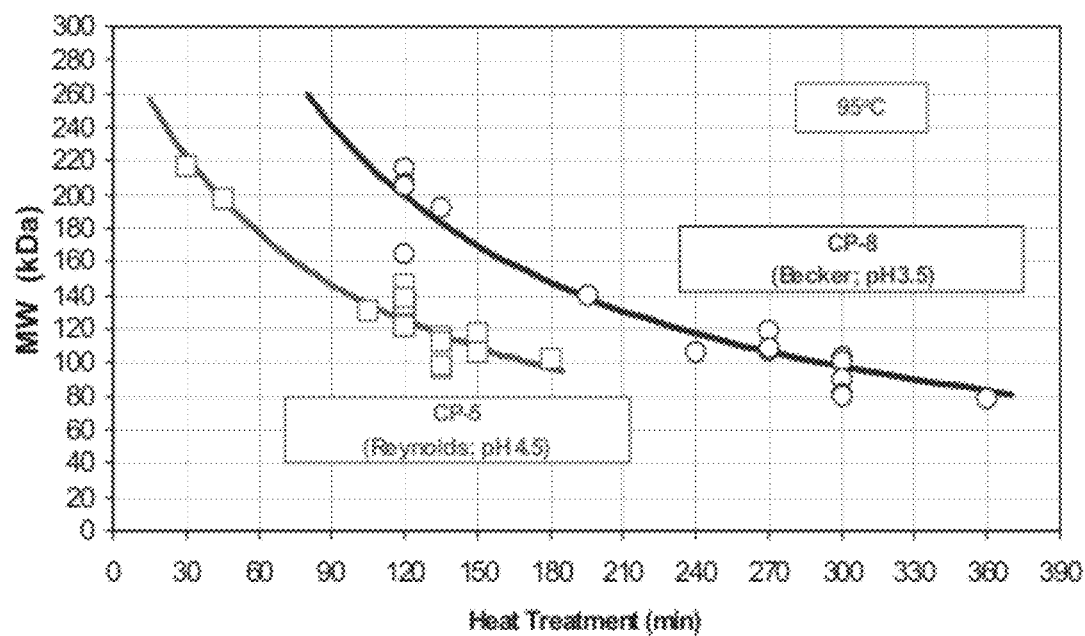
FIG. 4 shows the molecular weight of purified S. aureus serotype 8 capsular polysaccharide compared to serotype 5 capsular polysaccharide over time during heat treatment at pH 3,5 and 4.5, respectively, and 95° C.

Furthermore, FIG. 4 demonstrates a correlation between the molecular weight of purified CP8 with the treatment time for mild acid (pH 3.5 at 95° C.) hydrolysis. The purified polysaccharide is the final product obtained from the recovery process detailed previously. As also shown in FIG. 4, an increase in time of heat treatment of the S. aureus PFESA0005 strain at pH 3.5 resulted in smaller molecular weight CP8, whereas shorter heat treatment times at pH 3.5 resulted in higher molecular weight CP8. The size of the serotype 8 capsular polysaccharides ranged from about 80 kDa to about 220 kDa depending on the length of time of heat treatment at pH 3.5. The correlation between the time of heat treatment at low pH and size of the purified CP8, as shown in FIG. 4, allows for an estimation of the treatment time required to produce purified polysaccharide with a specified range of molecular weight.

It is important to note that as demonstrated above the full range of molecular weights of serotype 8 capsular polysaccharides from 20 kDa to more than 500 kDa can be produced, released and purified. The methods therefore may be used to produce specific ranges of desired high molecular weight capsule polysaccharides such as is shown in Table 3. The relatively narrow range of molecular weight polysaccharide produced where the peak molecular weights range from 87 kDa to 108 kDa represents a well characterized range of molecular weights that may be obtained by the methods described herein. A particularly advantageous range of high molecular weight polysaccharides, ranging from 70 kDa to 300 kDa or from 70 kDa to 150 kDa, is useful in making immunogenic compositions by conjugating the capsular polysaccharide to a carrier molecule or protein (see, Table 3). The conditions used to generate the CP8 capsule polysaccharide having a molecular weight range of from about 80 to 120 kDa are as follows: 95° C., pH 3.5 for 300 minutes.

TABLE 3

Production of Specific Range of High Molecular Weight Serotype 8 Capsular Polysaccharide.

| Run | Serotype 8 Capsular Polysaccharide MW (kDa) |
| --- | --- |
| 1 | 98 |
| 2 | 89 |
| 3 | 108 |
| 4 | 108 |
| 5 | 89 |
| 6 | 100 |
| 1 | 99 |
| 2 | 113 |
| 3 | 105 |
| 4 | 100 |
| 5 | 87 |

Example 2

Conjugation of Serotype 8 Capsular Polysaccharides to $CRM_{197}$

This example describes processes and characterization assays used in the production of S. aureus serotype 8 capsular polysaccharide-$CRM_{197}$ conjugates. Different conjugation chemistries were developed for conjugating S. aureus serotype 8 capsular polysaccharide to this carrier protein. For example, conjugation using PDPH (3-(2-pyridyldithio)-propionyl hydrazide) results in a covalent thioether bond between the CP and the carrier protein. Alternatively, conjugation using CDI/CDT (1,1-carboyldiimidazole/1,1-carboyl-di-1,2,4-triazole) results in a one-carbon or zero-carbon linker between CP and carrier protein.

Conjugation of Serotype 8 Capsular Polysaccharide to $CRM_{197}$ by PDPH Conjugation Chemistry The PDPH conjugation chemistry is a multi-step process that involves activation of the polysaccharide, removal of the thiol protecting group, purification of the activated polysaccharide intermediate, activation and purification of the CRM$_{197}$ protein, and conjugation of the activated components followed by purification. After introduction of a thiol group containing linker to the polysaccharide and a haloacetyl group to the CRM$_{197}$ protein carrier, S. aureus serotype 8 capsular polysaccharide was linked to the protein carrier through a thioether bond. Bromoacetyl groups were introduced into the CRM$_{197}$ protein by reaction of amine groups with the N-hydroxysuccimide ester of bromoacetic acid. To generate thiolated polysaccharide, the carbodiimide activated carboxylate groups of N-acetylmannosaminouronic acid in the polysaccharide were coupled to the hydrazide group of the sulfhydryl-reactive hydrazide heterobifunctional linker 3-(2-pyridyldithio)-propionyl hydrazide (PDPH). Thiols of PDPH-thiolated polysaccharide, generated by reduction with DTT and purified by SEC on a Sephadex G25 column, reacted with bromoacetyl groups of activated protein resulting in covalent thioether linkage formed by bromine displacement between polysaccharide and the carrier protein. Non-reacted bromoacetyl groups were "capped" with cysteamine hydrochloride (2-aminoethanethiol hydrochloride). The reaction mixture was then concentrated and diafiltered. The remaining unconjugated bromoacetyl groups were capped with cysteamine hydrochloride to ensure no reactive bromoacetyl groups were left after conjugation. This formed a covalent bond between the thiol end of cysteamine and the acetyl group on the lysine residue after displacement of bromine.

1. Thiolation of Aureus Serotype 8 Capsular Polysaccharide with PDPH:

The polysaccharide was first activated by thiolation with PDPH. The polysaccharide was mixed with a freshly prepared PDPH stock solution (250 mg/mL DMSO), an EDAC stock solution (90 mg/mL in diH$_2$O), and MES buffer stock solution (0.5M, pH 4.85) to make the final solution 0.1 M MES, and 2 and 4 mg polysaccharide/mL while maintaining a polysaccharide:PDPH:EDAC ratio by weight of 1:0.6:1.25 for serotype 8 capsular polysaccharide. This mixture was incubated for 1 hour at room temperature and then dialyzed against a 1000× volume of distilled H$_2$O four times using a 3500 MWCO dialysis device at between 4° C. and 8° C. to remove unreacted PDPH. The PDPH-linked polysaccharide was made 0.2 M DTT and incubated at room temperature for 3 hours or overnight at between 4° C. and 8° C. Excess DTT as well as the by-products of the reaction were separated from the activated saccharide by SEC using Sephadex G25 resin and distilled water as the mobile phase. Fractions were assayed by the DTDP assay for thiol groups and thiol-positive fractions that eluted near the void volume of the column were pooled. The pool of fractions was assayed by the PAHBAH and the O-acetyl assays to determine the degree of activation which is expressed as a molar percent of the repeat units containing a thiol group (molar concentration of thiols/molar concentration of repeat units). The activated polysaccharide was lyophilized and stored at –25° C. until needed for conjugation.

The results from the reproducibility of serotype 8 polysaccharide thiolation with PDPH are shown in Table 4. Degree of activation of serotype 8 polysaccharide was in the range 12% to 16%, which corresponds to approximately one linker molecule attached per ten capsular polysaccharide repeat units to one linker molecule per five repeat units.

TABLE 4

Activation of Serotype 8 Capsular Polysaccharide with PDPH - Reproducibility Study.

| Serotype 8 polysaccharide-PDPH | Activation (% M$_{SH}$/M$_{RU}$) | Scale mg | Yield mg (%, w/w) |
|---|---|---|---|
| 1 | 14 | 36 | 30 (83) |
| 2 | 16 | 30 | 27 (91) |
| 4 | 16 | 38 | 42 (110) |
| 5 | 12 | 40 | 44 (110) |

2. Carrier Protein Activation:

Separately, the carrier protein was activated by bromoacetylation. CRM$_{197}$ was diluted to 5 mg/mL with 10 mM phosphate buffered 0.9% NaCl pH 7 (PBS) and then made 0.1 M NaHCO$_3$ pH 7.0 using 1 M stock solution. The N-hydroxysuccinimide ester of bromoacetic acid (BAANS) was added at a CRM$_{197}$:BAANS ratio 1:0.25 (w:w) using a BAANS stock solution of 20 mg/mL DMSO. This reaction mixture was incubated at between 4 and 8° C. for 1 hour then purified using SEC on Sephadex G-25. The purified activated CRM$_{197}$ was assayed by the Lowry assay to determine the protein concentration and then diluted with PBS to 5 mg/mL. Sucrose was added to 5% wt/vol as a cryoprotectant and the activated protein was frozen and stored at –25° C. until needed for conjugation.

Bromoacetylation of lysine residues of CRM$_{197}$ was very consistent, resulting in the activation of 19 to 25 lysines from 39 lysines available (see, Table 5). The reaction produced high yields of activated protein.

TABLE 5

Yields and Degree of Bromoacetylation of CRM$_{197}$.

| Preparation | Lysines Activated (n=) | Scale (mg) | Yield (% w/w) |
|---|---|---|---|
| 1 | 24 | 23 | 85 |
| 2 | 20 | 38 | 87 |
| 3 | 19 | 35 | 77 |
| 4 | 22 | 35 | 94 |
| 5 | 23 | 35 | 87 |
| 6 | 25 | 48 | 104 |

3. Coupling Reaction:

Once the activated capsule polysaccharide and activated carrier protein were prepared, the two were combined in a conjugation reaction. The lyophilized and thiolated polysaccharide was dissolved in 0.16 M borate pH 8.95, mixed with thawed bromoacetylated CRM$_{197}$ and distilled water to make the final solution 0.1 M borate, 1:1 wt/wt ratio of CRM$_{197}$:polysaccharide, and 1 mg/mL polysaccharide. This mixture was incubated at room temperature for between 16 and 24 hours. Unreacted bromoacetyl groups on the protein were capped by adding cysteamine hydrochloride at a ratio of CRM$_{197}$:cysteamine of 1:2 (wt/wt) using a 135 mg/mL stock solution of cysteamine dissolved in 0.1 M borate pH 8.95 and incubated for 4 hours at room temperature. The capsule polysaccharide-CRM$_{197}$ conjugate (conjugate) was purified by diafiltering 50-fold against 0.9% NaCl using a 100K polyethersulfone ultrafilter.

The results from the reproducibility of serotype 8 capsular polysaccharide thiolation studies with PDPH demonstrated that the degree of activation of the polysaccharide was in the range 12 to 16% which corresponds to approximately one linker molecule attached per ten polysaccharide repeat units to one linker molecule per live repeat units.

Conjugation Serotype 8 Capsular Polysaccharide to CRM$_{197}$ by CDI/CDT Conjugation Chemistry.

CDI and CDT afford a one-step conjugation process where the polysaccharide is activated in an anhydrous environment (DMSO) to form imidazole or triazole carbamate moieties with available hydroxyls and acytimidazole or acyltriazole moieties with carboxylic acids. Addition of a protein carrier (in DMSO) leads to the nucleophilic displacement of the imidazole or triazole by lysine and formation of a carbamate linkage (for activated hydroxyls) and the amide linkage (for activated carboxylic acids).

Both CDI and CDT conjugation chemistries produced serotype 8 capsular polysaccharide covalently linked to the carrier protein, which was indicated by the presence of the saccharide and protein in the fractions from size exclusion chromatography, and by amino acid analysis of glycolaldehyde capped or cysteamine hydrochloride capped conjugate.

Summary of the results from the preparation of several lots of conjugates prepared by both PDPH and CDI/CDT chemistries for capsular serotype 8 with polysaccharide size in the range of 20 kDa to 40 kDa are shown in Table 6 below. There were no significant differences in the free capsule polysaccharide, ratio of polysaccharide-protein and yields of conjugates generated by these two conjugation methods. The antigenicity of conjugated serotype 8 capsular polysaccharide was not altered by conjugation as portrayed by identity precipitin line between conjugates and native polysaccharide.

TABLE 6

Characterization of Serotype 8 Capsular Polysaccharide-CRM197 Prepared by Two Conjugation Chemistries.

| Chemistry | CP Yield (%) | Protein Yield (%) | Output Ratio | Free sugar (%) | Free Protein (%) | Lysines Modified | Size (MW or Kd (% < 0.3), sacc/prot)) |
|---|---|---|---|---|---|---|---|
| CDI/CDT | 46-62 | 54-55 | 0.8-0.9 | 22-25 | <1 | 7-8 | 34/57 to 60/57 |
| PDPH | 34-70 | 61-83 | 0.6-0.9 | 15-41 | ND | 11-16 | 74-92% |

As shown above, the methods described herein may be used to produce specific ranges of desired high molecular weight capsule polysaccharides. We sought to prepare conjugates from a pre-selected range of high molecular weight that could be filtered and purified serotype 8 capsular polysaccharide for use in immunogenic compositions. Table 7 summarizes the analysis of serotype 8 capsular polysaccharide conjugates where the serotype 8 capsule polysaccharide ranged in molecular weight from about 80 kDa to 12.0 kDa and the imidazole conjugation chemistry was utilized. The molecular weights of the resulting conjugates ranged from 595 kDa to 1708 kDa. The number of conjugated lysines per CRM$_{197}$ ranged from a high of 9 to a low of 3. The free capsule polysaccharide ranged from a high of 6% to a low of 2%.

TABLE 7

Conjugates With Preselected Molecular Weight Range of Serotype 8 Capsular Polysaccharide.

| Run | Poly MW (kDa) | Yield (%) | Free Sacc. (%) | MW by SEC-MALLS (kDa) | Lysines Modified |
|---|---|---|---|---|---|
| 1 | 99 | 88 | 6 | 943 | 4 |
| 2 | 113 | 73 | 5 | 841 | 3 |
| 3 | 105 | 79 | 3 | 719 | 7 |
| 4 | 100 | 86 | 2 | 630 | 9 |
| 5 | 87 | 90 | 3 | 595 | 6 |

Both conjugation chemistries produce serotype 8 capsular polysaccharide covalently linked to carrier protein. There were no significant differences in free capsule polysaccharide, ratio of serotype 8 capsular polysaccharide:protein and yields of conjugates generated by these two methods.

Example 3

One Pot Versus Complex CDI/CDT Process

As described above, methods for making the immunogenic conjugates of the invention involve covalent conjugation of the capsular polysaccharides with the carrier proteins using conjugation chemistry involving CDI (1,1-carbonyldiimidazole), CDT (1,1-carboyl-di-1,2,4-triazole) or PDPH (3-(2-pyridyldithio)-propionyl hydrazide). Use of CDI/CDT results in a one-carbon or zero-carbon linker between capsular polysaccharide and carrier protein, while use of PDPH results in a covalent thioether bond between capsular polysaccharide and carrier protein.

The PDPH-based method was a multi-step process that involved activation of the polysaccharide, removal of a thiol protecting group on the polysaccharide, purification of the activated polysaccharide intermediate, activation and purification of the protein carrier, and conjugation of the activated components followed by purification. In this method, S. aureus serotype 8 capsular polysaccharides were reacted with PDPH and a carbodiimide in an aqueous solution such as 0.1M MES to produce PDPH-linked polysaccharides. The PDPH-linked polysaccharides were reacted with a reducing agent to produce activated polysaccharides that were then purified. Carrier proteins were reacted with bromoacetic acid N-hydroxysuccinimide ester in an aqueous solution to produce activated carrier proteins that were then purified. The purified activated serotype 8 polysaccharides were then reacted with the purified activated carrier proteins to produce serotype 8 polysaccharide:carrier protein conjugates.

In contrast, the CDI- and CDT-based methods were one or two step conjugation processes, in which the capsular polysaccharide was activated in an anhydrous environment (i.e., DMSO) to form imidazole or triazole carbamate moieties with available hydroxyls and acylimidazole or acyltriazole moieties with carboxylic acids. Addition of the protein carrier (in DMSO) lead to a nucleophilic displacement of the imidazole or triazole by lysine and formation of a carbamate linkage (for activated hydroxyls) and the amide linkage (for activated carboxylic acids). Accordingly, two CDI- or CDT-based methods were developed: a more complex process and a simpler one-pot process. In the more complex process, S. aureus serotype 8 capsular polysaccharides were compounded with imidazole or triazole, lyophilized, and then reacted with CDI or CDT in an organic solvent (such as DMSO) to produce activated serotype 8 polysaccharides. The activated serotype 8 polysaccharides were purified and then reacted with carrier proteins in the organic solvent to produce serotype 8 polysaccharide-carrier protein conjugates. The one-pot process was similar to the complex process except that the activated serotype 8 polysaccharides were not purified prior to the reaction with carrier proteins.

CDI/CDT Complex Process.

Activation of Polysaccharide:

Serotype 8 polysaccharide was mixed with 10 g triazole/g serotype 8 and lyophilized. The resulting cake was dissolved in DMSO at 2.0 mg serotype 8 polysaccharide/mL. The water content was determined. A freshly prepared stock solution of CDT at 100 mg/mL in DMSO was added to achieve a molar amount of CDT equivalent to the water. Alternatively, the amount of CDT added may be adjusted to achieve a higher or lower degree of activation. This was held 30 minutes at 23° C.

Purification of Activated Serotype 8 Polysaccharide:

The solution of activated serotype 8 (ACP8) was poured into 25 volumes of water to destroy excess CDT. This was concentrated to its original volume on a 10 kDa PES membrane at approximately 1 mg/cm$^2$ and diafiltered against water for at least 10 volumes. This step was completed in less than 4 hours. The diafiltered material was mixed with 10 g triazole/g of original serotype 8 polysaccharide and lyophilized.

Preparation of Lyophilized CRM:

CRM was diafiltered against 0.4% NaCl/5% sucrose at constant volume on a 10 kDa PES membrane for at least 10 volumes. The protein concentration was determined and sufficient diafiltration buffer was added to bring the protein concentration to 5.0 g/L, thus affording a w/w ratio of NaCl/CRM=0.8. The CRM was lyophilized.

Conjugation:

Activated, diafiltered serotype 8 polysaccharide was dissolved in DMSO at 1 mg/mL. Borate solution at 100 mM was added to achieve 2% v/v.

CRM was resuspended at 2 mg/mL and, when dissolution was complete, combined with the ACP8 solution. This was allowed to react at 23° C. for 20 hours.

The conjugate reaction was poured into 24 volumes of 5 mM borate pH 9.0 and allowed to stir at room temperature for 1 hour. It was then adjusted to pH 7.5 with 0.5 M phosphate buffer, pH 6.5. This was filtered through a 5 micron filter and concentrated to the original volume on a 300 kDa PES membrane at a load of ~1 mg/cm$^2$ and diafiltered against at least 10 volumes of water. The resulting concentrate was filtered through a 0.22 micron filter and stored at 2° C.-8° C.

CDI/CDT One Pot Process.

CRM$_{197}$ Matrix Exchange:

CRM$_{197}$ was diafiltered to exchange from the bulk matrix of approximately 10 mM phosphate/80 mM NaCl/1.5% sucrose, pH 7 to 5 mM imidazole/0.72% NaCl/15 mM octyl-β-D-glucoside, pH 7. The exchange allowed the removal of phosphate and sucrose which are detrimental to the conjugation and defines the sodium chloride content carried into the conjugation. Octyl-β-D-glucopyranoside is added prevent particle formation after sterile filtration.

The matrix of the CRM$_{197}$ was exchanged by tangential flow filtration against 5 mM imidazole/0.72%/15 mM octyl-B-D-glucopyranoside pH 7 through 10 diavolumes using 10K MWCO PES membranes at a retentate concentration of approximately 4 mg/mL. Typical membrane challenge was 2 grams/ft$^2$ and the target final CRM$_{197}$ concentration in the matrix was 6 mg/mL. The CRM$_{197}$ was stored at 2° C.-8° C.

Activation/Conjugation:

The activation/conjugation process for S. aureus serotype 8 capsular polysaccharide consisted of the following steps: 1) Matrix exchange of the CRM197; 2) Compounding of polysaccharide; 3) Shell freezing and lyophilization of CRM$_{197}$ and compounded polysaccharide; 4) Dissolution of the lyophilized polysaccharide and CRM$_{197}$; 5) Activation of the polysaccharide; 6) Conjugation of the activated polysaccharide to CRM$_{197}$; and 7) Purification of the conjugate (dilution, diafiltration, sterile filtration).

The polysaccharide was compounded with 10 grams of 1,2,4-triazole excipient per gram of polysaccharide. The excipient was added as a powder to the polysaccharide, with a solution obtained after less than 15 minutes of mixing at ambient temperature.

The compounded polysaccharide and CRM$_{197}$ were shell frozen separately using a −75° C. ethanol bath. The volume per 1 L bottle was approximately 500 mL.

For the polysaccharide dissolution, DMSO was added to the individual lyophilization bottles of the polysaccharide to obtain a suspension and then transferred to the activation/conjugation reaction vessel for heating. DMSO was added to obtain 2 g/L concentration. A clear solution was obtained as the suspension reached approximately 45° C. with mixing. The solution was then cooled to 23° C.±2° C.

For the CRM$_{197}$ dissolution, DMSO was added to the individual lyophilization bottles containing the CRM$_{197}$ to obtain a suspension and then transferred to a second vessel for mixing. DMSO was added to obtain 2 g/L concentration. A clear solution was typically obtained in less than 15 minutes.

The polysaccharide/DMSO solution was sampled for Karl Fischer analysis to determine moisture content. CDT was prepared as a 100 mg/mL solution in DMSO and was added based on determined moisture content. Continuous addition of the CDT solution was performed over about 5 minutes at 23° C.±2° C. with mixing. The reaction was allowed to proceed for a minimum of 30 minutes at 23° C.±2° C. The reaction was sampled to determine activation level (UV 220/205 nm) and then 100 mM sodium borate, pH 9 was added to obtain a 1.5% aqueous solution. The reaction solution was then stirred for a minimum of 30 minutes at 23° C.±2° C.

For conjugation of the activated polysaccharide to CRM$_{197}$, DMSO was added to target a 0.8 mg/mL reaction concentration. The dissolved CRM$_{197}$ in DMSO was then added to the activated polysaccharide solution with mixing. The reaction was stirred for a minimum of 4 hours at 23° C.±2° C.

The reaction solution was 10× diluted by its addition into 5 mM sodium tetraborate, pH 9 with mixing to hydrolyze residual activation groups. The diluted solution was passed through a 5 μm filter and concentrated to a target retentate concentration of 2 g/L. Tangential flow filtration was performed using 300K regenerated cellulose membranes through 20 diavolumes with 5 mM succinate, pH 7. Typical membrane challenge was 1 gram/ft$^2$. The purified conjugate was passed through a 0.22 micron filter and stored at 2° C.-8° C.

Example 4

Conjugation of Serotype 8 Capsular Polysaccharide Using One-Pot and Complex Conjugation Process This example demonstrates that pre-selected range of molecular weights of capsule polysaccharides can be used for conjugation in either the one-pot or complex process. The larger polysaccharides are initially produced by the bacterial cells, and the resulting molecular weight range purified can be controlled by pH and heat of the hydrolysis process in Example 1 (as shown in Table 3).

In this example, eight batches where the serotype 8 capsule polysaccharide ranged in molecular weight from about 80 kDa to about 120 kDa were selected and conjugation was performed using activation with 1,1-carbonyl-di-(1,2,4-triazole) for serotype 8 capsular polysaccharide. See, Table 8. The molecular weights of the resulting conjugates ranged from 595 kDa to 1708 kDa. The number of conjugated lysines per CRM ranged from a high of 13 to a low of 3. The free sugar ranged from a high of 11% to a low of 1%.

TABLE 8

Serotype 8 Capsular Polysaccharide Conjugates Prepared with 80 kDa to 120 kDa Capsular Polysaccharides.

| Process | Run | Poly MW (kDa) | Sacc Yield (%) | Free Sugar (%) | MW by SEC-MALLS (kDa) | Lysine |
|---|---|---|---|---|---|---|
| One Pot | 1 | 98 | 86 | 1 | 751 | 11 |
|  | 2 | 89 | 80 | 1 | 675 | 13 |
|  | 3 | 108 | 76 | 4 | 1073 | 5.0 |
|  | 4 | 108 | 69 | 4 | 819 | 5.2 |
|  | 5 | 89 | 85.1 | 8 | 1708 | 10 |
|  | 6 | 100 | 94.0 | 11 | 1577 | 5 |
| Complex | 1 | 99 | 88 | 6 | 943 | 4 |
|  | 2 | 113 | 73 | 5 | 841 | 3 |
|  | 3 | 105 | 79 | 3 | 719 | 7 |
|  | 4 | 100 | 86 | 2 | 630 | 9 |
|  | 5 | 87 | 90 | 3 | 595 | 6 |

Example 5

Evaluation of the Conjugated Native- and Base-Treated Serotype 8 Capsular Polysaccharide in a Murine Bacteremia Model The importance of O-acetyl groups present on native serotype 8 capsular polysaccharide before conjugation for induction of functional antibody responses was evaluated for capsular polysaccharide conjugates. Serotype 8 capsular polysaccharide was de-O-Acetylated under mild basic conditions, and both NMR and Ion Chromatography (IC) confirmed absence of O-acetylation in serotype 8 capsular polysaccharide de-O—Ac-CRM. The CP8 de-O—Ac-CRM conjugate was prepared by conjugation of de-O—Ac CP8 polysaccharide to CRM by PDPH chemistry as described in Example 2.

The serotype 8 capsular polysaccharide conjugate unexpectedly showed no measurable acetyl groups by IC method. This could be attributed to differences in the structure, sites of O-acetylation compared to other S. aureus capsular polysaccharides, which in turn could cause the removal or modification of acetyl groups in serotype 8 capsular polysaccharides during conjugation.

The murine bacteremia model was used to evaluate efficacy of the native versus base-treated serotype 8 capsular polysaccharide conjugated to CRM. Groups of female BALB/c mice (15/group) were vaccinated at weeks 0, 3 and 6 with 1 mcg serotype 8 capsular polysaccharide de-O—Ac-CRM or 1 µg serotype 8 capsular polysaccharide O—Ac-CRM. Vaccines were formulated with 22 mcg $AlPO_4$. Animals were challenged with S. aureus PFESA0003, and bacteria were enumerated from the blood three hours later. The data showed that there was a statistically significant (p=0.0362) reduction in bacterial cfu recovered from the blood of animals immunized with untreated native serotype 8 capsular polysaccharide conjugate as determined by the Student t-Test (Table 9). In animals that were immunized with base-treated serotype 8 capsular polysaccharide conjugate, the bacterial cfu recovered from blood were similar to the saline control group.

TABLE 9

Serotype 8 Capsular Polysaccharide-$CRM_{197}$ Conjugate Reduces Bacteremia Caused By S. aureus PFESA0003 In Mice.

| Antigen | Strain/Dose | LogCFU/ Blood | Significance (p value) |
|---|---|---|---|
| Saline | PFESA0003 | 4.35 |  |
| CP8 de-O-Ac-CRM | $1.14 \times 10^8$ | 4.45 |  |
| CP8 O-Ac-CRM |  | 3.93 | 0.03 |

Example 6

Evaluation of the Conjugated Native and Base Treated Serotype 8 Capsular Polysaccharide in a Murine Bacteremia Model Serotype 8 capsular polysaccharide conjugates were evaluated for their ability to protect mice in a pyelonephritis model. Bacterial counts in the blood of mice receiving i.p. S. aureus challenge were significantly reduced as compared to controls immunized with PBS.

Figure 5:
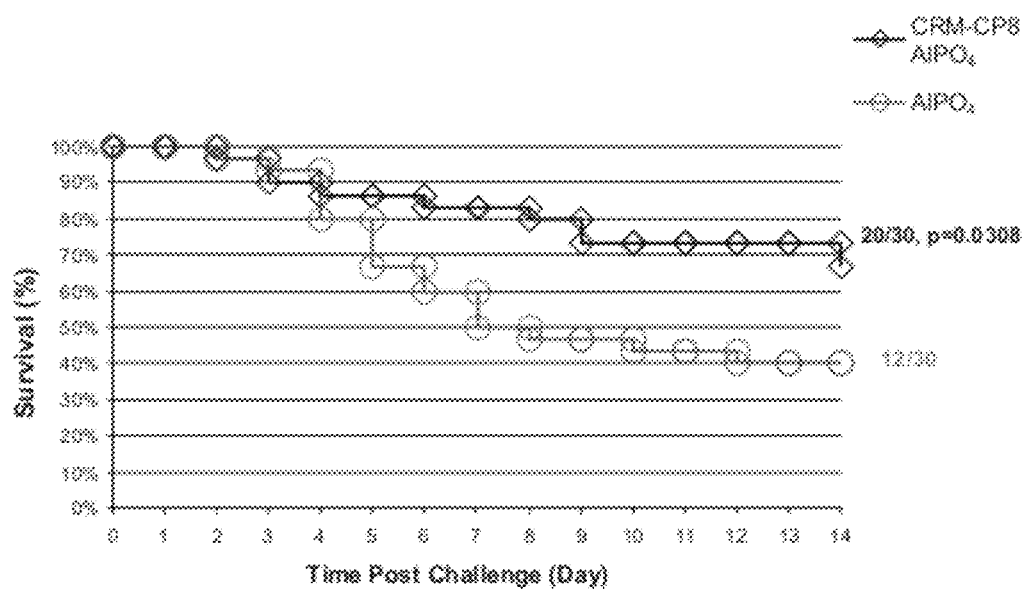
FIG. 5 shows increased survival in mice that received a serotype 8 capsular polysaccharide-$CRM_{197}$ conjugate (diamonds) compared to $AlPO_4$-treated controls (circles).

Two studies were conducted to evaluate efficacy of CP8-$CRM_{197}$ conjugate in the murine bacteremia model, described previously, after challenge with S. aureus PFESA0268 (Type 8). The first study (FIG. 5) showed a significant reduction of bacteremia (p=0.0308). For the study, groups of 6-8 week old Swiss Webster mice (n=30) were actively immunized by subcutaneous injection with 1 µg serotype 8 capsular polysaccharide-$CRM_{197}$ and saline both formulated with 100 µg $AlPO_4$ at 0, 2 and 4 weeks and challenged at week 6 by the intravenous route with S. aureus PFESA0268 (Type 8). Prior challenge experiments were conducted to optimize the dose of challenge strain at the age mice reach after three vaccinations. Statistical evaluation of survival studies was carried out by Kaplan-Meier analysis.

Example 7

Opsonic Activity of Sera from Mice Immunized with Native and Chemically Modified Serotype 8 Capsular Polysaccharide Conjugates Select mouse sera (n=5) with high serotype 8 capsular polysaccharide titers from a vaccination study were compared for opsonic activity using PFESA0005 strain. The OPA results (Table 10) show that only conjugates prepared by the conjugation of native serotype 8 capsular polysaccharide elicited opsonic antibodies in mice. It is noteworthy that the de-OAc serotype 8 capsular polysaccharide conjugate was immunogenic in mice but the antibodies elicited were not opsonic in this assay. OPA titers are reported as reciprocal of dilution at which 40% killing was observed.

TABLE 10

Opsonic Activity of Native Serotype 8 Capsular Polysaccharide vs. de-O-Ac Serotype 8 Capsular Polysaccharide-CRM Immunized Mouse Sera.

| De-O-Ac Serotype 8 Capsular Polysaccharide-CRM | | Serotype 8 Capsular Polysaccharide-CRM | |
|---|---|---|---|
| OP titer Wk 0 sera | OP titer Wk 8 sera | OP titer Wk 0 sera | OP titer Wk 8 sera |
| <50 | <50 | 50 | 150 |
| <50 | <50 | <50 | 1350 |

TABLE 10-continued

Opsonic Activity of Native Serotype 8 Capsular
Polysaccharide vs. de-O-Ac Serotype 8 Capsular
Polysaccharide-CRM Immunized Mouse Sera.

| De-O-Ac Serotype 8 Capsular Polysaccharide-CRM | | Serotype 8 Capsular Polysaccharide-CRM | |
|---|---|---|---|
| OP titer Wk 0 sera | OP titer Wk 8 sera | OP titer Wk 0 sera | OP titer Wk 8 sera |
| <50 | <50 | <50 | 450 |
| <50 | <50 | <50 | 1350 |
| <50 | <50 | <50 | 4050 |

Example 8

Killing of S. aureus Strains by Serotype 8 Conjugate Antisera can be Inhibited by Addition of Native Serotype 8 Capsular Polysaccharide To confirm the specificity of the killing, the opsonophagocytic assay was performed in the presence of native serotype 8 capsular polysaccharide or unrelated pneumococcal polysaccharide (Pn 14 poly), essentially as described above.

The results (Table 11) showed that the presence of native serotype 8 capsular polysaccharide in reaction mixture inhibited opsonophagocytic killing of S. aureus PFESA0286 (Type 8). These results confirm that opsonophagocytic killing by immune sera is mediated by capsule specific antibodies.

TABLE 11

Addition Serotype 8 Capsular Polysaccharide Inhibits Opsonophagocytic Killing of S. aureus by Immune Sera.

| Monkey | Sera Sample | OPA titer |
|---|---|---|
| 02D133 | Wk 0 | <50 |
| | Wk 8 | 4050 |
| | Wk 0 + 20 µg CP8 poly | <50 |
| | Wk 8 + 20 µg CP8 poly | <50 |
| | Wk 0 + 20 µg Pn14 poly | <50 |
| | Wk 8 + 20 µg Pn 14 poly | 4050 |
| A4N122 | Wk 0 | <50 |
| | Wk 8 | 4050 |
| | Wk 0 + 20 µg CP8 poly | <50 |
| | Wk 8 + 20 µg CP8 poly | <50 |
| | Wk 0 + 20 µg Pn14 poly | <50 |
| | Wk 8 + 20 µg Pn 14 poly | 1350 |

Summary

All conjugation chemistries produced serotype 8 capsular polysaccharide covalently linked to the carrier protein $CRM_{197}$. There were no significant differences in free saccharide, ratio of serotype 8 capsular polysaccharide:protein and yields of conjugates generated by these methods.

Example 9

Preparation of S. aureus Serotype 5 Capsular Polysaccharide

In this example, production of various size ranges of S. aureus serotype 5 capsular polysaccharide is described. The structure of S. aureus serotype 5 capsular polysaccharide repeat unit is shown in FIG. 6. The methods described herein are effective in producing serotype 5 capsular polysaccharide with molecular weights ranging from about 20 kDa to 800 kDa. By proper selection of conditions, high molecular weight serotype 5 capsular polysaccharides can be isolated and purified ranging from 50 kDa to 800 kDa in molecular weight. For use in immunogenic compositions, serotype 5 capsular polysaccharide can be isolated and purified ranging from 70 kDa to 300 kDa in molecular weight, from 70 kDa to 150 kDa and many other desired ranges. Strain PFESA0266 was chosen for serotype 5 capsular polysaccharide production based on growth characteristics and the quantity of capsule produced.

For production of serotype 5 capsular polysaccharide, strain PFESA0266 was grown in a complex medium consisting primarily of a carbon source (either lactose or sucrose), hydrolyzed soyflour as the nitrogen source, and trace metals. The strain was grown in bioreactors for 2 to 5 days.

Fermentation of the PFESA0266 strain was carried out as detailed above. At the time of harvest, $OD_{600}$ of the culture was 7.38. The culture was autoclaved for 1 hour and after cooling, the culture was processed as described above to separate cells from supernatant material. Approximately 1 L each of filtered and concentrated supernatant and cells were recovered.

Prior to autoclaving, a sample was removed to test the level of Staphylococcal enterotoxin B (SEB) in the culture. In the presence of 0.05% polysorbate 80, the concentration of SEB in the fermentation was 15-20 ng/ml. Previous experiments showed that autoclaving the culture for 1 hour reduced the level of SEB to less than 0.1 ng/ml, which is below the limit of detection for the TECRA kit.

Diafiltered, ethanol-fractionated polysaccharide was loaded onto a Q-Sepharose AEC column and eluted with a linear gradient of NaCl as described above. Fractions were analyzed by the O-acetyl assay and double immunodifusion test for presence of serotype 5 polysaccharide and phosphate assay for the presence of teichoic acid. The presence of serotype 5 polysaccharide was detected in fractions 60 to 105 (FIGS. 7A-B). To reduce contamination with teichoic acid, fractions 60 to 85 were pooled and any residual teichoic acid was oxidized with sodium-metaperiodate to allow its removal by 3K diafiltration against $diH_2O$.

Purification of serotype 5 capsular polysaccharide used for the preparation of conjugates was performed by two different methods that rely on elevated temperature and low pH to affect the release of capsule from the cell and reduce the molecular weight of the polysaccharide. The resulting molecular weight depended on the time, temperature and pH of the hydrolysis step.

Characterization of serotype 5 capsular polysaccharide was performed using the techniques specified in Table 1, supra.

Capsule polysaccharides produced by the methods described below result in pure polysaccharides with low levels of protein, nucleic acid, peptidoglycan and teichoic acid contaminants.

In the first method, following release of the capsule polysaccharide from the cell and reduction of molecular weight, the preparation was treated with a cocktail of enzymes (e.g., ribonuclease, deoxyribonuclease, lysozyme and protease) to digest impurities. After incubation, residual impurities were precipitated by the addition of ethanol (final concentration about 25%). After removal of the residual ethanol, a solution containing capsule polysaccharide was loaded onto an anion exchange column (Q-Sepharose) and eluted with a linear salt gradient. Fractions containing capsule polysaccharide were pooled and treated with sodium meta-periodate. This treatment resulted in the oxidative hydrolysis of residual teichoic acid contaminant, but did not affect serotype 5 capsular polysaccharide. The reaction was quenched by the addition of ethylene glycol. The material was concentrated and diafiltered against distilled water (dH$_2$0) to remove any residual reagents and by-products.

The second method was used to produce capsule polysaccharide without the use of enzymes to digest the various cell-derived impurities. In this method, following release of the capsule polysaccharide from the cell and reduction of molecular weight, the hydrolyzed fermentation broth was clarified by microfiltration followed by ultrafiltration and diafiltration. The solution was treated with activated carbon to remove impurities. After carbon treatment, the material was treated with sodium meta-periodate to oxidize residual teichoic acid followed by quenching with propylene glycol. The material was concentrated and diafiltered against dH$_2$O to remove any residual reagents and by-products.

Preparations produced using either method resulted in pure capsular polysaccharides with low levels of protein, nucleic acid and teichoic acid contaminants. The methods described can be used to produce specific ranges of the desired high molecular weight polysaccharides by manipulating the conditions of hydrolysis.

Examples of capsular polysaccharide obtainable by the methods described herein are shown in Table 12 below. Batches of purified serotype 5 capsular polysaccharide had high purity as indicated by no teichoic acid (TA), peptidoglycan and low residual protein. See, Tables 12 and 13. The range of molecular weights spanned 132.7 kDa to 800 kDa and the purified polysaccharides were highly O-acetylated, ranging from 90%-100%, and were 100% N-acetylated. The yields of serotype 5 capsular polysaccharide purification were 39% to 63%, and the size of purified serotype 5 polysaccharide varied from 35 kDa to 65 kDa (see, Table 12). The level of teichoic acid (TA) contamination was acceptable and levels of residual proteins and nucleic acid were also in acceptable ranges. NMR spectra of serotype 5 polysaccharide were identical to ones reported in the literature.

TABLE 12

Serotype 5 Capsular Polysaccharide Characterization.

| Sample | Total CP5 Purified mg | Yield % | MW (kDa) (g/mol) | Protein % (w/w) | Nuc. Acid (260 nm scan) % (w/w) | O-acetyl NMR (%) |
|---|---|---|---|---|---|---|
| 1 | 101 | 39 | 47 | 0 | 0.5 | 94 |
| 2 | 91 | 48 | 65 | 1.2 | 2.5 | 96 |
| 3 | 578 | 63 | 35 | 2.5 | 0.7 | 75 |

TABLE 13

Additional Serotype 5 Capsular Polysaccharide Characterization.

| Sample | MW (kDa) | CP5 (mg/ml) | O-acetyl NMR (%) | Identity NMR | N-acetyl NMR (%) |
|---|---|---|---|---|---|
| 1 | 800.1 | 3.164 | 100 | Pass | 100 |
| 2 | 132.7 | 1.172 | 90 | Pass | 100 |
| 3 | 335.4 | 0.975 | 90 | Pass | 100 |
| 4 | 366.8 | 0.865 | 90 | Pass | ND |

ND = not detected

Molecular Weight Selection of Capsular Polysaccharides:

A kinetic analysis demonstrated that a broad range of molecular weights of capsule polysaccharides can be generated by the methods described herein. Initially, larger polysaccharides were produced by the bacterial cells, and subsequently, a desired molecular weight range selected and then purified by manipulation of the pH and heat conditions of the heat and hydrolysis steps.

Heat treatment of S. aureus fermentation broth is a process step between fermentation and capsular polysaccharide recovery. This process step uses heat to treat pH-adjusted broth for a specified period. The goals of the heat treatment at low pH were to kill cells, inactivate enterotoxins, release cell bound polysaccharide and reduce molecular weight to the desired size. Among these goals, the reduction of molecular weight was the slowest in terms of processing time required in this step. Therefore, the other goals were inevitably achieved within the treatment time considered.

Heat Treatment:

pH and temperature conditions for selecting various molecular weight ranges of capsule polysaccharides were determined. A 15 L Biolafitte Fermenter was used for these studies. The fermentation broth was transferred to the fermenter by a peristaltic pump. Using an agitation speed of about 200 rpm, the broth pH was adjusted with concentrated sulfuric acid. Then, the broth temperature was raised to the set value. The heat treatment time started as soon as the temperature reached the set point. When the desired treatment time was reached, the broth was cooled to room temperature. In-process samples were taken to determine polysaccharide concentration and molecular weight by HPLC and SEC-MALLS systems, respectively. The molecular weight (MW) data was used in the kinetic analysis. The MW profiles were determined over time at pH 3.5, 4.0 and 5.0. See, FIG. 8A.

The kinetics of mild acid hydrolysis of polysaccharides was conducted using purified serotype 8 capsular polysaccharide obtained from the process. The purified polysaccharide solution was adjusted to the desired pH for the experiment with sulfuric acid. About 1.5 mL of the solution was transferred to each of the 15 mL centrifuge tubes. The tubes were placed in an oil bath equipped with a precision temperature control system. The tubes were taken out at a predetermined time intervals and quenched in an ice bucket. At the end of the experiment, an aliquot of 1M Tris buffer (pH 7.5) was added to the sample to adjust the pH back to about 7. The samples were analyzed by a SEC-MALLS system. The MW data was used in the kinetic analysis. The effect of temperature on MW profile of CP5 at pH 4.5 was determined over time. See, FIG. 8B.

Results

As shown in FIG. 8A, a lower pH was more effective in reducing the molecular weight of the polysaccharide. In this example, ranges of molecular weights between about 300 kDa and about 600 kDa can be generated using a pH of 5 at 95° C. for between 15 minutes and 120 minutes. See FIG. 8A. Likewise, choosing a pH of 4.5 at 95° C. for between 15 minutes and 120 minutes can yield polysaccharide molecular weight ranges between 200 kDa and 400 kDa. In addition, choosing a pH of 4.0 at 95° C. for between 15 minutes and 120 minutes can yield polysaccharide molecular weight ranges between 120 kDa and 300 kDa.

As shown in FIG. 8B, the higher the temperature, the faster the rate of hydrolysis and broader the molecular weights of polysaccharide produced with time. Expressed another way, use of a lower temperature, 55° C. versus 95° C. at the same pH, produces a narrower range of polysaccharide molecular weights.

Furthermore, FIG. 4 demonstrates a correlation between the molecular weight of purified serotype 5 capsular polysaccharide with the treatment time for mild acid (pH 4.5 at 95°

C.) hydrolysis. The purified polysaccharide is the final product obtained from the recovery process detailed previously. As also shown in FIG. 4, an increase in time of heat treatment of the S. aureus PFESA0266 strain at pH 4.5 resulted in smaller molecular weight serotype 8 capsular polysaccharide, whereas shorter heat treatment times at pH 4.5 resulted in higher molecular weight serotype 5 capsular polysaccharide. The size of serotype 5 capsular polysaccharides ranged from about 90 kDa to about 220 kDa depending on the length of time of heat treatment at pH 4.5. A correlation between the time of heat treatment at low pH and size of the purified serotype 5 capsular polysaccharides, as shown in FIG. 4, allows for an estimation of the treatment time required to produce purified polysaccharide with a specified range of molecular weight.

As demonstrated above, the full range of molecular weights of serotype 5 capsular polysaccharides from 20 kDa to more than 500 kDa can be produced, released and purified. The methods described may be used to produce specific ranges of desired high molecular weight capsule polysaccharides such as is shown in Table 14. The relatively narrow range of molecular weight polysaccharide produced where the peak molecular weights range from 63 kDa to 142 kDa represents a well characterized range of molecular weights that may be obtained by the methods described herein. A particularly advantageous range of high molecular weight polysaccharides, ranging from 70 kDa to 300 kDa or from 70 kDa to 150 kDa, is useful in making immunogenic compositions by conjugating the capsular polysaccharide to a carrier molecule or protein. The conditions used to generate the CP5 capsule polysaccharide having a molecular weight range of from about 100 to 140 kDa are as follows: 95° C., pH 4.5 for 135 minutes. Different combinations of pH, temperature, and time, however, will also generate CP5 molecules with a molecular weight range of about 100 to 140 kDa.

TABLE 14

Production of Specific Range of High Molecular Weight Serotype 5 Capsular Polysaccharide.

| Run | Serotype 5 Capsular Polysaccharide MW (kDa) |
|---|---|
| 1 | 142 |
| 2 | 108 |
| 3 | 142 |
| 4 | 108 |
| 5 | ND |
| 6 | ND |
| 7 | 63 |
| 8 | 72 |
| 9 | 74 |
| 10 | 63 |
| 11 | ND |

ND = not done

Example 10

Conjugation of Serotype 5 Capsular Polysaccharides to $CRM_{197}$

This example describes processes and characterization assays used in the production of S. aureus serotype 5 capsular polysaccharide-$CRM_{197}$ conjugates. Different conjugation chemistries were developed for conjugating S. aureus serotype 5 capsular polysaccharide to this carrier protein. For example, conjugation using PDPH (3-(2-pyridyldithio)-propionyl hydrazide) results in covalent thioether bond between the CP and the carrier protein; whereas conjugation using CDT (1,1-carboyl-di-1,2,4-triazole) results in a one-carbon or zero-carbon linker between the capsular polysaccharide and carrier protein.

Conjugation of Serotype 5 Capsular Polysaccharide to $CRM_{197}$ by PDPH Conjugation Chemistry.

The PDPH conjugation chemistry is a multi-step process that involves activation of the polysaccharide, removal of the thiol protecting group, purification of the activated polysaccharide intermediate, activation and purification of the $CRM_{197}$ protein, and conjugation of the activated components followed by purification. After introduction of a thiol group containing linker to the polysaccharide and a haloacetyl group to the $CRM_{197}$ protein carrier, S. aureus serotype 5 capsular polysaccharide was linked to the protein carrier through a thioether bond. Bromoacetyl groups were introduced into the $CRM_{197}$ protein by reaction of amine groups with the N-hydroxysuccimide ester of bromoacetic acid. To generate thiolated polysaccharide, the carbodiimide activated carboxylate groups of N-acetylmannosaminouronic acid in the polysaccharide were coupled to the hydrazide group of the sulfhydryl-reactive hydrazide heterobifunctional linker 3-(2-pyridyldithio)-propionyl hydrazide (PDPH). Thiols of PDPH-thiolated polysaccharide, generated by reduction with DTT and purified by SEC on a Sephadex G25 column, reacted with bromoacetyl groups of activated protein resulting in covalent thioether linkage formed by bromine displacement between polysaccharide and the carrier protein. Non-reacted bromoacetyl groups were "capped" with cysteamine hydrochloride (2-aminoethanethiol hydrochloride). The reaction mixture was then concentrated and diafiltered. The remaining unconjugated bromoacetyl groups were capped with cysteamine hydrochloride to ensure no reactive bromoacetyl groups were left after conjugation. This formed a covalent bond between the thiol end of cysteamine and the acetyl group on the lysine residue after displacement of bromine.

1. Thiolation of S. aureus Serotype 5 Capsular Polysaccharide with PDPH:

The polysaccharide was first activated by thiolation with PDPH. The polysaccharide was mixed with a freshly prepared PDPH stock solution (250 mg/mL in DMSO), an EDAC stock solution (90 mg/mL in $diH_2O$), and MES buffer stock solution (0.5M, pH 4.85) to make the final solution 0.1 M MES, and 2 mg and 4 mg capsular polysaccharide/mL while maintaining a capsular polysaccharide:PDPH:EDAC ratio by weight of 1:5:3 for serotype 5 capsular polysaccharide. This mixture was incubated for 1 hour at room temperature and then dialyzed against a 1000× volume of distilled $H_2O$ four times using a 3500 MWCO dialysis device at between 4° C. and 8° C. to remove unreacted PDPH. The PDPH-linked polysaccharide was made 0.2 M DTT and incubated at room temperature for 3 hours or overnight at between 4° C. and 8° C. Excess DTT as well as the by-products of the reaction were separated from the activated saccharide by SEC using Sephadex G25 resin and distilled water as the mobile phase. Fractions were assayed by the DTDP assay for thiol groups and thiol-positive fractions that eluted near the void volume of the column were pooled. The pool of fractions was assayed by the PAHBAH and the O-acetyl assays to determine the degree of activation, which is expressed as a molar percent of the repeat units containing a thiol group (molar concentration of thiols/molar concentration of repeat units). The activated polysaccharide was lyophilized and stored at −25° C. until needed for conjugation.

The results from the reproducibility of serotype 5 polysaccharide thiolation with PDPH are shown in Table 15. Degree of activation of serotype 5 polysaccharide was in the range 11% to 19%, which corresponds to approximately one linker molecule attached per ten capsular polysaccharide repeat units to one linker molecule per five repeat units.

TABLE 15

Activation of Serotype 5 Capsular Polysaccharide with PDPH - Reproducibility Study.

| Serotype 5 polysaccharide-PDPH | Activation (% $M_{SH}/M_{RU}$) | Scale mg | Yield mg (%, w/w) |
|---|---|---|---|
| 1 | 11 | 23 | 19.6 (85) |
| 2 | 13 | 30 | 28 (93) |
| 3 | 19 | 30 | 23 (77) |
| 4 | 15 | 32 | 29 (90) |

2. Carrier Protein Activation:

Separately, the carrier protein was activated by bromoacetylation. $CRM_{197}$ was diluted to 5 mg/mL with 10 mM phosphate buffered 0.9% NaCl pH 7 (PBS) and then made 0.1 M $NaHCO_3$ pH 7.0 using 1 M stock solution. The N-hydroxysuccinimide ester of bromoacetic acid (BAANS) was added at a $CRM_{197}$:BAANS ratio 1:0.25 (w:w) using a BAANS stock solution of 20 mg/mL DMSO. This reaction mixture was incubated at between 4 and 8° C., for 1 hour then purified using SEC on Sephadex G-25. The purified activated $CRM_{197}$ was assayed by the Lowry assay to determine the protein concentration and then diluted with PBS to 5 mg/mL. Sucrose was added to 5% wt/vol as a cryoprotectant and the activated protein was frozen and stored at −25° C. until needed fir conjugation.

Bromoacetylation of lysine residues of $CRM_{197}$ was very consistent, resulting in the activation of 19 to 25 lysines from 39 lysines available (see, Table 16). The reaction produced high yields of activated protein.

TABLE 16

Yields and Degree of Bromoacetylation of $CRM_{197}$.

| Preparation | Lysines Activated (n=) | Scale (mg) | Yield (% w/w) |
|---|---|---|---|
| 1 | 24 | 23 | 85 |
| 2 | 20 | 38 | 87 |
| 3 | 19 | 35 | 77 |
| 4 | 22 | 35 | 94 |
| 5 | 23 | 35 | 87 |
| 6 | 25 | 48 | 104 |

3. Coupling Reaction:

Once the activated capsule polysaccharide and activated carrier protein were prepared, the two were combined in a conjugation reaction. The lyophilized and thiolated polysaccharide was dissolved in 0.16 M borate pH 8.95, mixed with thawed bromoacetylated $CRM_{197}$ and distilled water to make the final solution 0.1 M borate, 1:1 wt/wt ratio of $CRM_{197}$:polysaccharide, and 2 mg/mL serotype 5 capsular polysaccharide. This mixture was incubated at room temperature for between 16 and 24 hours. Unreacted bromoacetyl groups on the protein were capped by adding cysteamine hydrochloride at a ratio of $CRM_{197}$:cysteamine of 1:2 (wt/wt) using a 135 mg/mL stock solution of cysteamine dissolved in 0.1 M borate pH 8.95 and incubated for 4 hours at room temperature. The capsule polysaccharide-$CRM_{197}$ conjugate (conjugate) was purified by diafiltering 50-fold against 0.9% NaCl using a 100K polyethersulfone ultrafilter.

The results from the reproducibility of serotype 5 capsular polysaccharide thiolation studies with PDPH demonstrated that the degree of activation was in the range of 11% to 19%, which corresponds to approximately one linker molecule attached per ten CP repeat units to one linker molecule per five repeat units.

Conjugation of Serotype 5 Capsular Polysaccharide to $CRM_{197}$ by CDT Conjugation Chemistry.

CDT affords a one-step conjugation process where the polysaccharide is activated in an anhydrous environment (DMSO) to form triazole carbamate moieties with available hydroxyls and acylimidazole or acyltriazole moieties with carboxylic acids. Addition of a protein carrier (in DMSO) leads to the nucleophilic displacement of the triazole by lysine and formation of a carbamate linkage (for activated hydroxyls) and the amide linkage (for activated carboxylic acids). The reaction solution is diluted 10-fold into an aqueous solution in preparation for purification by tangential flow filtration.

CDT conjugation chemistry produced serotype 5 capsular polysaccharide covalently linked to the carrier protein, which was indicated by the presence of the saccharide and protein in the fractions from size exclusion chromatography, and by amino acid analysis of glycolaldehyde capped or cysteamine hydrochloride capped conjugate.

A summary of the results from the preparation of several lots of conjugates prepared by both PDPH and CDT chemistries for serotype 5 capsular polysaccharide sizes in the range of 20 kDa to 40 kDa is shown in Table 17 below. There were no significant differences in the free capsule polysaccharide, ratio of polysaccharide:protein and yields of conjugates generated by these conjugation chemistries. The antigenicity of conjugated serotype 5 capsular polysaccharide was not altered by conjugation as portrayed by identity precipitin line between conjugates and native polysaccharide.

TABLE 17

Characterization of Serotype 5 Capsular Polysaccharide-$CRM_{197}$ Prepared by Two Conjugation Chemistries.

| Chemistry | CP Yield (%) | Protein Yield (%) | Output Ratio | Free sugar (%) | Free Protein (%) | Lysines Modified | Size (MW or Kd (% < 0.3), sacc/prot)) |
|---|---|---|---|---|---|---|---|
| CDT | 19-27 | 35 | 0.5-0.8 | 10-40 | <1 | 18-22 | 38/61 to 76/74 |
| PDPH | 26-52 | 40-99 | 0.4-1.0 | 23-50 | ND | ND | 7.5 × $10^5$ to 2.3 × $10^6$ |

ND = not detected

As shown above, the methods described herein may be used to produce specific ranges of desired high molecular weight capsule polysaccharides. We sought to prepare conjugates from a pre-selected range of high molecular weight that could be filtered and purified serotype 5 capsular polysaccharide for use in immunogenic compositions. Table 18 summarizes the analysis of serotype 5 capsular polysaccharide conjugates where the serotype 5 capsule polysaccharide ranged in molecular weight from about 92 kDa to about 119 kDa and activated with triazole (CDT). The molecular weights of the resulting conjugates ranged from 1533 kDa to 2656. The number of conjugated lysines per $CRM_{197}$ ranged from a high of 22 to a low of 15. The free capsule polysaccharide ranged from a high of 18% to a low of 11%.

TABLE 18

Conjugates With Preselected Molecular Weight Range of Serotype 5 Capsular Polysaccharide

| Run | Poly MW (kDa) | Yield (%) | Free Sacc. (%) | MW by SEC-MALLS (kDa) | Lysines Modified |
|---|---|---|---|---|---|
| 1 | 121 | 63 | 11 | 2130 | 19 |
| 2 | 92 | 72 | 16 | 1533 | 22 |
| 3 | 119 | 74 | 14 | 2656 | 15 |
| 4 | 115 | 63 | 18 | 1911 | 15 |

Both conjugation chemistries produce serotype 5 capsular polysaccharide covalently linked to carrier protein. There were no significant differences in free capsule polysaccharide, ratio of serotype 5 capsular polysaccharide:protein and yields of conjugates generated by these two methods.

Example 11

Complex Versus One-Pot CDT Processes

As described above, methods fir making the immunogenic conjugates of the invention involve covalent conjugation of the capsular polysaccharides with the carrier proteins using conjugation chemistry involving CDT (1,1-carboyl-di-1,2,4-triazole) or PDPH (3-(2-pyridyldithio)-propionyl hydrazide). Use of CDT resulted in a one-carbon or zero-carbon linker between capsular polysaccharide and carrier protein, white use of PDPH results in a five carbon linker containing covalent thioether bond between capsular polysaccharide and carrier protein.

The PDPH-based method was a multi-step process that involved activation of the polysaccharide, removal of a thiol protecting group on the polysaccharide, purification of the activated polysaccharide intermediate, activation and purification of the protein carrier, and conjugation of the activated components followed by purification. In this method, S. aureus serotype 5 capsular polysaccharides were reacted with PDPH and a carbodiimide in an organic solvent such as DMSO to produce PDPH-linked polysaccharides. The PDPH-linked polysaccharides were reacted with a reducing agent to produce activated polysaccharides that were then purified. Carrier proteins were reacted with bromoacetic acid in an organic solvent to produce activated carrier proteins that were then purified. The purified activated serotype 5 polysaccharides were then reacted with the purified activated carrier proteins to produce serotype 5 polysaccharide:carrier protein conjugates.

In contrast, the CDT-based methods were one-step conjugation processes, in which the capsular polysaccharide was activated in an anhydrous environment (i.e., DMSO) to form triazole carbamate moieties with available hydroxyls and acylimidazole or acyltriazole moieties with carboxylic acids. Addition of the protein carrier (in DMSO) lead to a nucleophilic displacement of the imidazole or triazole by lysine and formation of a carbamate linkage (for activated hydroxyls) and the amide linkage (for activated carboxylic acids), thereby permitting the conjugation to proceed in "one pot." Accordingly, two CDT-based methods were developed: a more complex process and a simpler one-pot process. In the more complex process, S. aureus serotype 5 capsular polysaccharides were compounded with imidazole or triazole and then reacted with CDT in an organic solvent (such as DMSO) and about 0.2% w/v water to produce activated serotype 5 polysaccharides. The activated serotype 5 polysaccharides were purified and then reacted with carrier proteins in the organic solvent to produce serotype 5 polysaccharide:carrier protein conjugates. The one-pot process was similar to the complex process except that the activated serotype 5 polysaccharides were not purified prior to the reaction with carrier proteins.

CDT Complex Process

Activation of Serotype 5 Capsular Polysaccharide:

Serotype 5 capsular polysaccharide was mixed with 10 g triazole/g serotype 5 capsular polysaccharide and lyophilized. The resulting cake was dissolved in DMSO at 2.0 mg serotype 5 capsular polysaccharide/mL. The water content was determined and adjusted to 0.2%. A freshly prepared stock solution of CDT at 100 mg/mL in DMSO was added to achieve a 20 fold molar excess amount of CDT compared to the amount of CP5. Alternatively, the amount of CDT added may be adjusted to achieve a higher or lower degree of activation. This was held 30 minutes at 23° C.

Purification of Activated Serotype 5 Capsular Polysaccharide:

The solution of activated serotype 5 capsular polysaccharide (ACP5) was poured into 25 volumes of water to destroy excess CDT. This was concentrated to its original volume on a 10 kDa PES membrane at approximately 1 mg/cm2 and diafiltered against water for at least 10 volumes. This step was completed in less than 4 hours. The diafiltered material was mixed with 10 g triazole/g of original serotype 5 polysaccharide and lyophilized.

Preparation of Lyophilized CRM:

CRM was diafiltered against 0.4% NaCl/5% sucrose at constant volume on a 10 kDa PES membrane for at least 10 volumes. The protein concentration was determined and sufficient diafiltration buffer was added to bring the protein concentration to 5.0 g/L, thus affording a w/w ratio of NaCl/CRM=0.8. The CRM was lyophilized.

Conjugation:

Activated, diafiltered serotype 5 capsular polysaccharide was dissolved in DMSO at 1 mg/mL. Borate solution at 100 mM was added to achieve 2% v/v.

CRM was resuspended at 2 mg/mL and, when dissolution was complete, combined with the ACP5 solution. This was allowed to react at 4° C. for 20 hours.

The conjugate reaction was poured into 24 volumes of 5 mM borate pH 9.0 and allowed to stir at room temperature for 1 hour. It was then adjusted to pH 7.5 with 0.5 M phosphate buffer, pH 6.5. This was filtered through a 5 micron filter and concentrated to the original volume on a 300 kDa PES membrane at a load of ~1 mg/cm$^2$ and diafiltered against at least 10 volumes of water. The resulting concentrate was filtered through a 0.22 micron filter and stored at 2° C.-8° C.

CDT One Pot Process

CRM$_{19}$ Matrix Exchange:

CRM$_{197}$ was diafiltered to exchange from the bulk matrix of approximately 10 mM phosphate/80 mM NaCl/15% sucrose, pH 7 to 5 mM imidazole/0.72% NaCl/15 mM octyl-β-D-glucopyranoside, pH 7. The exchange allowed the removal of phosphate and sucrose which are detrimental to the conjugation and defines the sodium chloride content carried into the conjugation. Octyl-β-D-glucopyranoside is added prevent particle formation after sterile filtration.

The matrix of the CRM$_{197}$ was exchanged by tangential flow filtration against 5 mM imidazole/0.72% Nacl/15 mM octyl-β-D-ghicopyranoside, pH 7 through 10 diavolumes using 10K MWCO PES membranes at a retentate concentration of approximately 4 mg/mL. Typical membrane challenge was 2 grams/ft2 and the target final $CRM_{197}$ concentration in the matrix was 6 mg/mL. The $CRM_{197}$ was stored at 2° C.-8° C.

Activation/Conjugation:

The activation/conjugation process for *S. aureus* serotype 5 capsular polysaccharide consisted of the following steps: 1) Compounding of polysaccharide; 2) Shell freezing and lyophilization of $CRM_{197}$ and compounded polysaccharide; 3) Dissolution of the lyophilized polysaccharide and $CRM_{197}$; 4) Activation of the polysaccharide; 5) Conjugation of the activated polysaccharide to $CRM_{197}$; and 6) Purification of the conjugate (dilution, diafiltration, sterile filtration).

The polysaccharide was compounded with 10 grams of 1,2,4-triazole excipient per gram of polysaccharide. The excipient was added as a power the polysaccharide, with a solution obtained after less than 15 minutes of mixing at ambient temperature.

The compounded polysaccharide and $CRM_{197}$ were shell frozen separately using a −75° C. ethanol bath. The volume per 1 L bottle was approximately 500 mL.

For the polysaccharide dissolution, DMSO was added to the individual lyophilization bottles of the polysaccharide to obtain a suspension and then transferred to the activation/conjugation reaction vessel for heating. DMSO was added to obtain 2 g/L concentration. A clear solution was obtained after 5-10 minutes of mixing.

For the $CRM_{197}$ dissolution, DMSO was added to the individual lyophilization bottles containing the $CRM_{197}$ to obtain a suspension and then transferred to a second vessel for mixing. DMSO was added to obtain 2 g/L concentration. A clear solution was typically obtained in less than 15 minutes.

The polysaccharide/DMSO solution was sampled for Karl Fischer analysis to determine moisture content. CDT was prepared as a 100 mg/mL solution in DMSO and was added at a 5 molar excess to type 5 polysaccharide (the complex process used 20 molar equivalents CDT while the one-pot process used 5 molar equivalents CDT:CP5). Continuous addition of the CDT solution was performed over about 5 minutes at 23° C.±2° C. with mixing. The reaction was allowed to proceed for a minimum of 30 minutes at 23° C.±2° C. The reaction was sampled to determine activation level (UV 220/205 nm) and then 100 mM sodium borate, pH 9 was added to obtain a 1.5% aqueous solution. The reaction solution was then stirred for a minimum of 30 minutes at 23° C.±2° C.

For conjugation of the activated polysaccharide to $CRM_{197}$, DMSO was added to target a 0.55 mg/mL reaction concentration. The dissolved $CRM_{197}$ in DMSO was then added to the activated polysaccharide solution with mixing. The reaction was stirred for a minimum of 16 hours at 23° C.±2° C.

The reaction solution was 10× diluted with 5 mM sodium tetraborate, pH 8.6 to obtain a final diluted pH of 9±0.2. The solution was stirred a 23±3° C. for a minimum of 4 hours. The diluted solution was passed through a 5 μm filter and concentrated to a target retentate concentration of 2 g/L. Tangential flow filtration was performed using 300K regenerated cellulose membranes through 20 diavolumes with 5 mM succinate, pH 7. Typical membrane challenge was 1 gram/ft2. The purified conjugate was passed through a 0.22 micron filter and stored at 2° C.-8"C.

Example 12

Conjugation of Serotype 5 Capsular Polysaccharide Using One-Pot and Complex Conjugation Process This example demonstrates that pre-selected range of molecular weights of capsule polysaccharides can be used for conjugation in either the one-pot or complex process. The larger polysaccharides are initially produced by the bacterial cells and the resulting molecular weight range purified can be controlled by pH and heat of the hydrolysis process in Example 9. In this example, eight batches where the serotype 5 capsular polysaccharide ranged in molecular weight from about 90 kDa to about 140 kDa were selected and conjugation was performed using activation with triazole (CDT) in either the one-pot or complex processes described above. See, Table 19. The molecular weights of the resulting conjugates ranged from 1125 kDa to 2656 kDa. The number of conjugated lysines per CRM ranged from a high of 22 to a low of 15. The free sugar ranged from a high of 23% to a low of 11%.

TABLE 19

Serotype 5 Capsular Polysaccharide Conjugates Prepared with 90 kDa to 140 kDa Capsular Polysaccharides.

| Process | Run | Poly MW (kDa) | Sacc Yield (%) | Free Sugar (%) | MW by SEC-MALLS (kDa) | Lysine |
|---|---|---|---|---|---|---|
| One Pot | 1 | 142 | 93 | 11 | 1932 | 19 |
|  | 2 | 108 | 93 | 14 | 1117 | 20 |
|  | 3 | 142 | 85 | 17 | 1609 | 15 |
|  | 4 | 108 | 86 | 23 | 1125 | 15 |
| Complex | 1 | 121 | 63 | 11 | 2130 | 19 |
|  | 2 | 92 | 77 | 16 | 1533 | 22 |
|  | 3 | 119 | 74 | 14 | 2656 | 15 |
|  | 4 | 115 | 63 | 18 | 1911 | 15 |

Example 13

Serotype 5 Capsular Polysaccharide Conjugates Consistently Exhibit Protection in Murine Pyelonephritis Model Serotype 5 capsular polysaccharide conjugates were evaluated for their ability to protect mice in a pyelonephritis model. Bacterial counts in the blood of mice receiving i.p. *S. aureus* challenge were significantly reduced as compared to controls immunized with PBS.

Figure 9:
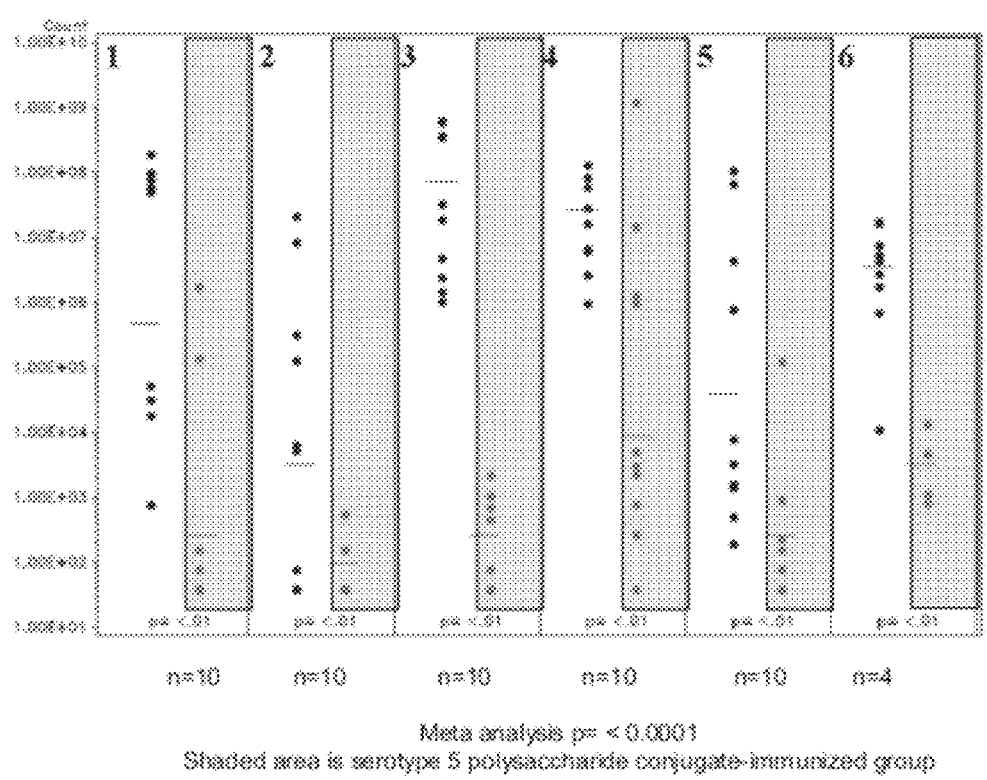
FIG. 9 shows reduced pyelonephritis, in mice that received a serotype 5 polysaccharide-$CRM_{497}$ conjugate compared to PBS-treated controls (shaded area is the treated mice).

All six individual studies showed a significant reduction in cfu/ml kidneys in immunized animals (FIG. 9). When these studies were pooled for meta analysis, the overall significance for the studies as a whole increased to below 0.0001. The data showed consistent reduction of kidney colonization after active vaccinations with the capsular polysaccharide conjugate.

Example 14

Serotype 5 Capsular Polysaccharide Conjugates Prepared by Different Conjugation Chemistries Protect Mice Against Experimental Infections Active immunization studies in the murine pyelonephritis model were conducted with serotype 5 capsular polysaccharide conjugates prepared either by PDPH or CDT chemistry. The methods for conjugating capsular polysaccharides to $CRM_{197}$ are described above. Results showed that both conjugates reduce colonization in mice compared to the sham immunized animals (Table 20).

TABLE 20

Effect of PDPH vs. CDT Conjugation on Protection Against
S. aureus Challenge in Pyelonephritis Model.

| Study # | Antigens | Strain/Dose | logCFU/Kidney | Significance |
|---|---|---|---|---|
| Study 1 | Saline + AlPO$_4$ | PFESA0266 2 × 10$^8$ | 5.53 ± 1.90 | — |
| | 1 mcg CP5-CRM (PDPH) + AlPO$_4$ | | 3.01 ± 1.83 | p < 0.001 |
| | 1 mcg CP5-CRM (CDT) + AlPO$_4$ | | 1.67 ± 0.23 | p < 0.0001 |
| Study 2 | Saline + AlPO$_4$ | PFESA0266s 2.7 × 10$^8$ | 6.17 ± 1.76 | — |
| | 1 mcg CP5-CRM (PDPH) + AlPO$_4$ | | 3.06 ± 1.69 | p < 0.0001 |
| | 1 mcg CP5-CRM (CDT) + AlPO$_4$ | | 1.87 ± 0.69 | p < 0.0001 |

Example 15

Active Immunization of Serotype 5 Capsular Polysaccharide Conjugate Protects Rats in a Rat Endocarditis Model Four studies were conducted with CP5-CRM$_{197}$ PDPH conjugate. The serotype 5 capsular polysaccharide conjugates significantly reduced recovered CPU after challenge with S. aureus PFESA0266 in both the heart and kidneys in 2 of 3 experiments (Table 21). In the third study, the Geometric Mean Titer (GMT) anti-CP5 titer was the lowest of the three experiments, but it was only slightly lower than in the previous experiment.

TABLE 21

Serotype 5 Capsular Polysaccharide-CRM$_{197}$ Immunization Reduces CFU in a Rat Endocarditis Model.

| Immunogenic Composition | Challenge Strain/Dose | Log CFU Recovered Heart | Log CFU Recovered Kidney | Significance Heart | Significance Kidney | GMT CP Titer |
|---|---|---|---|---|---|---|
| 1 mcg CP5-CRM | PFESA0266 | 4.34 ± 1.78 | 3.92 ± 1.73 | | | 103,000 |
| 1 mcg PP5-CRM | 2.21 × 10$^8$ cfu | 7.94 ± 0.78 | 6.77 ± 0.79 | p <0.001 | p < 0.05 | |
| 1 mcg CP5-CRM | PFESA0266 | 4.43 ± 2.30 | 3.11 ± 2.33 | | | 51,000 |
| Saline | 6.5 × 10$^7$ cfu | 5.63 ± 2.48 | 4.19 ± 2.05 | No | No | |
| 1 mcg CP5-CRM | PFESA0266 | 4.01 ± 2.49 | 3.90 ± 1.92 | | | 67,000 |
| Saline | 4.0 × 10$^8$ cfu | 7.52 ± 1.38 | 6.52 ± 1.17 | p < 0.0002 | p < 0.0002 | |

Example 16

Figure 11:
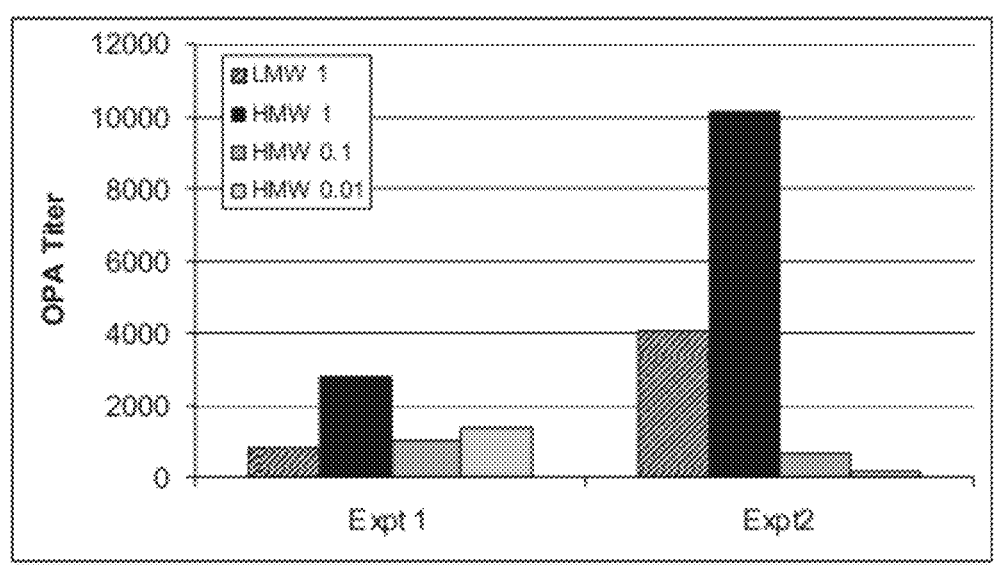
FIG. 11 shows a comparison of OPA titers (geomean) from serum obtained from mice vaccinated with different formulations of polysaccharide conjugate (high molecular weight (HMW) CP5-CRM, low molecular weight (LMW) CP5-CRM). Groups consisted of 5 to 9 mice.

Enhanced Immunogenicity of HMW CP5 Conjugate Vaccines in Mice Compared to LMW CP5 Conjugate Vaccines A murine pyelonephritis study was conducted to evaluate the immunogenicity and effectiveness of different CP5 conjugate formulations. Two formulations were tested: The first formulation was composed of a high molecular weight (HMW) CP5 (approximately 300 kDa) conjugated to CRM197. The second formulation contained a low molecular weight (LMW) CP5 (approximately 25 kDa) conjugated to CRM197. Three dose levels were tested for the HMW vaccine (1, 0.1 and 0.01 mcg). The LMW vaccine was tested at 1 mcg. A negative control group was also included composed of a polysaccharide conjugate vaccine derived from Streptococcus pneumoniae conjugated to CRM197 (PP5). Polysaccharides were formulated with 22 mcg AlPO4 on weeks 0, 3 and 6 and challenged with S. aureus PFESA0266 on week 8. Kidneys were harvested and bacterial colonies enumerated 48 hours after challenge. Both vaccines were effective at generating an immune response and a reduction in CFUs of S. aureus PFESA0266 was observed from the kidneys of mice vaccinated with the 1 µg groups of both HMW and LMW vaccine. This was dosage dependent as demonstrated by reduced effectiveness from the lower vaccine dosages (FIG. 10). The CFU readout was not sensitive enough to detect a difference in efficacy for the HMW and LMW vaccines. Sera from the mice were therefore tested by OPA. OPA titers were defined as the dilution of serum required to kill 40% of S. aureus Strain PFESA0266 in an OPA assay. Enhanced OPA titers were seen for the HMW vaccine compared to the LMW formulation (FIG. 11).

Example 17

Capsule Polysaccharide Conjugates Comprising High Molecular Weight Polysaccharides Show Enhanced Immunogenicity Compared to Conjugates Comprising Low Molecular Weight Polysaccharides Non human primate (NHP) studies were conducted to evaluate the immunogenicity of different capsule conjugate formulations. Two formulations were tested at two different dosage levels (2 and 20 µg). The first formulation contained a high molecular weight (HMW) polysaccharide (approximately 130 kDa) conjugated to CRM$_{197}$. The second formulation contained a low molecular weight (LMW) polysaccharide (approximately 25 kDa) conjugated to CRM$_{197}$. Groups of five primates were vaccinated with a single dose of either vaccine and immune titers were monitored prior to vaccination and two weeks post vaccination. OPA titers were defined as the dilution of serum required to kill 40% of S. aureus Strain PFESA0266 in an OPA assay. Antibody titers were also monitored by ELISA. Enhanced activity was seen for the HMW vaccine compared to the LMW formulation (Table 22), evidenced by a ten fold rise in antibody titers for the HMW vaccine compared to the LMW vaccine. The OPA responder rate for the NHPs that received the HMW vaccine were also higher (80% compared to 40%).

TABLE 22

Enhanced Immunogenicity is observed for HMW polysaccharide conjugate vaccines compared to LMW polysaccharide conjugate vaccine.

| | CP5-CRM197 dose level (mcg) per animal | Geometric Mean of PD1* | OPA Responder Rate (%)± |
|---|---|---|---|
| HMW (125 kDa) | 20 | 32 | 80 |
| | 2 | 21 | 80 |
| LMW (25 kDa) | 20 | 3 | 40 |
| | 2 | 8 | 40 |

*Fold rise calculated from CP5 ELISA titer 2 weeks post vaccination compared to pre vaccine titers.
±Responder rate calculated from monkeys generating a rise in OPA titer following a single dose of vaccine 2 weeks post vaccination.
Each group contained 5 Rhesus maccaques and vaccines were formulated with AlPO4 (250 mcg/dose)

Example 18

Polysaccharide O-Acetylation is Important for Induction of Protective Antibody Responses to Serotype 5 Capsular Polysaccharide Conjugate To evaluate the importance of O-acetylation of serotype 5 capsular polysaccharide, the native capsular polysaccharide was de-O-acetylated (dOAc) and conjugated to $CRM_{197}$ (dOAc-$CRM_{197}$) using PDPH conjugation chemistry, as discussed above. The efficacy of dOAcCP-$CRM_{197}$ conjugate was compared side-by-side with CP5-$CRM_{197}$ in a murine pyelonephritis model.

Immunization with conjugates lacking O-acetyl groups (dOAc CP5-CRM) failed to reduce recovered bacterial CFU in the kidneys. These data (Table 23) indicate that O-acetylation is important for elicitation of functional antibodies against CP5.

TABLE 23

Immunization with De-O-Acetylated Serotype 5 Capsular Polysaccharide Conjugates Did Not Protect Mice from Kidney Colonization.

| Study # | Antigens | Strain/Dose | LogCFU/ Kidney | Significance |
|---|---|---|---|---|
| Study 1 | 1 mcg PP5-CRM | PFESA0266 | 3.89 ± 2.24 | |
| | 1 mcg dOAc CP5-CRM | 7 × 10$^8$ | 4.20 ± 1.75 | |
| | 1 mcg CP5-CRM | | 1.75 ± 0.39 | p-value < 0.008 |
| Study 2 | Saline | PFESA0266 | 5.08 ± 1.96 | |
| | 1 mcg dOAc CP5-CRM | 2.4 × 10$^8$ | 5.89 ± 1.29 | |
| | 1 mcg CP5-CRM | | 2.93 ± 2.11 | p-value < 0.02 |

Example 19

Confirmation of the Importance of O-Acetylation as Functional Epitope of Serotype 5 Capsular Polysaccharide by OPA Using Monoclonal Antibodies with Known Specificities Serotype 5 capsular polysaccharide monoclonal antibodies with specificities to OAc+ (CP5-7-1), OAc-1+/− (CP5-5-1) and OAc− (CP5-6-1) were evaluated for OP killing activity against the type 5 strain PFESA0266 (Table 24). Monoclonal antibodies to serotype 8 capsular polysaccharide (CP8-3-1 specific to CP8 OAc+) were used as negative control.

The OAc-specific anti-CP5 mAb CP5-7-1 mediated killing of S. aureus PFESA0266 (Table 24). Also monoclonal antibody CP5-5-1, which recognizes epitopes shared by both CP5 OAc+ and CP5 OAc−, mediated killing of the PFESA0266 strain. The monoclonal antibody specific for epitopes present on serotype 5 OAc− capsular polysaccharide did not mediate killing of the PFESA0266 strain. These results indicate that O-Acetyl epitopes on serotype 5 capsular polysaccharide are necessary to elicit functional activity of serotype 5-specific antibodies.

Antibodies need to be functional as measured by the killing of bacteria in an animal efficacy model or an opsonophagocytic killing assay that demonstrates the antibodies kill the bacteria. Functional killing may not be demonstrated using an assay that monitors the generation of antibodies alone, which is not indicative of the importance of O-acetylation in efficacy.

TABLE 24

Monoclonal Antibodies Specific to O-Acetylated (+) Serotype 5 Capsular Polysaccharide and O- and de-O-Acetylated (+/−) Serotype 5 Capsular Polysaccharide Are Opsonic Against S. aureus PFESA0266 (Type 5).

| CP5-5-1 (O—Ac+/−) (mcg) | | | | CP5-6-1 (O—Ac−) (mcg) | | | | CP5-7-1 (O—Ac+) (mcg) | | | | CP8-3-1 (−control) (mcg) | | | |
|---|---|---|---|---|---|---|---|---|---|---|---|---|---|---|---|
| 20 | 10 | 5 | 2.5 | 20 | 10 | 5 | 2.5 | 20 | 10 | 5 | 2.5 | 20 | 10 | 5 | 2.5 |
| 28 | 33 | 30 | 21 | −12 | −5 | −12 | −5 | 31 | 46 | 49 | 55 | −18 | −3 | −13 | −5 |

Data reported as percent killing and was calculated by determining the ratio of the number of CFU surviving at 60 minutes in wells with bacteria, antibodies, complement and HL-60 cells to the number of CFU surviving in wells lacking antibodies but containing bacteria, complement and HL-60 cells.

Example 20

Enhanced Immunogenicity is Observed for CP5 Conjugates Composed of High Molecular Weight Polysaccharides Compared to Low Molecular Weight Polysaccharides in Non Human Primates (NHP)

Non human primate (NHP) studies were conducted to evaluate the immunogenicity of different capsule conjugate formulations. Two formulations were tested at two different dosage levels (2 and 20 μg). The first formulation was composed of a high molecular weight (HMW) polysaccharide (approximately 130 kDa) conjugated to CRM197. The second formulation contained a low molecular weight (LMW) polysaccharide (approximately 25 kDa) conjugated to CRM197. Groups of five primates were vaccinated with a single dose of either vaccine and immune titers were monitored prior to vaccination and two weeks post vaccination. OPA titers were defined as the dilution of serum required to kill 40% of S. aureus Strain PFESA0266 in an OPA assay. Antibody titers were also monitored by ELISA. Enhanced activity was seen for the HMW vaccine compared to the LMW formulation (Table 25). There was a three to ten fold rise in antibody titers for the HMW vaccine compared to the LMW vaccine. The OPA responder rate for the NHPs that received the HMW vaccine were also higher (80% compared to 40%).

TABLE 25

Enhanced Immunogenicity is observed for HMW polysaccharide conjugate vaccines compared to LMW polysaccharide conjugate vaccine.

| | CP5-CRM197 dose level (mcg) per animal | Geometric Mean of PD1* | OPA Responder Rate (%)± |
|---|---|---|---|
| HMW (125 kDa) | 20 | 32 | 80 |
| | 2 | 21 | 80 |
| LMW (25 kDa) | 20 | 3 | 40 |
| | 2 | 8 | 40 |

*Fold rise calculated from CP5 ELISA titer 2 weeks post vaccination compared to pre vaccine titers.
±Responder rate calculated from monkeys generating a rise in OPA titer following a single dose of vaccine 2 weeks post vaccination.
Each group contained 5 Rhesus maccaques and vaccines were formulated with AlPO4 (250 mcg/dose)

Summary

Both conjugation chemistries, described herein, produced serotype 5 capsular polysaccharide covalently linked to the carrier protein CRM197. There were no significant differences in free saccharide, ratio of serotype 5 polysaccharide: protein and yields of conjugates generated by these two methods.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

What is claimed is:

1. An immunogenic polysaccharide-protein conjugate comprising an isolated Staphylococcus aureus capsular polysaccharide conjugated to a carrier protein, wherein the polysaccharide has a molecular weight of between 70 kDa and 300 kDa, wherein the conjugate has a molecular weight range of between about 600 kDa and about 2800 kDa, and wherein the conjugate comprises a one-carbon or zero-carbon linker between the polysaccharide and the carrier protein.

2. The immunogenic conjugate of claim 1, wherein the immunogenic conjugate has a molecular weight of between 595 kDa and 1708 kDa.

3. The immunogenic conjugate of claim 1, wherein the polysaccharide has a molecular weight range of between 70 kDa and 150 kDa.

4. An immunogenic polysaccharide-protein conjugate comprising an isolated Staphylococcus aureus capsular polysaccharide conjugated to a carrier protein, wherein the polysaccharide has a molecular weight of between 70 kDa and 300 kDa, wherein the conjugate has a molecular weight range of between 500 kDa and 2500 kDa, and wherein the conjugate comprises a one-carbon or zero-carbon linker between the polysaccharide and the carrier protein.

5. The immunogenic conjugate of claim 1, wherein the polysaccharide has a degree of O-acetylation between 10-100%.

6. The immunogenic conjugate of claim 5, wherein the polysaccharide has a degree of O-acetylation between 50-100%.

7. The immunogenic conjugate of claim 6, wherein the polysaccharide has a degree of O-acetylation between 75-100%.

8. The immunogenic conjugate of claim 1, wherein the carrier protein is CRM197.

9. The immunogenic conjugate of claim 8, wherein the CRM197 is covalently linked to the polysaccharide through a carbamate linkage, an amide linkage, or both.

10. The immunogenic conjugate of claim 9, wherein the molar ratio of the conjugated lysines in the CRM197 to the CRM197 is about 10:1 to about 25:1.

11. The immunogenic conjugate of claim 9, wherein at least one covalent linkage between CRM197 and polysaccharide occurs at least at every 5 to 10 saccharide repeat units of the polysaccharide.

12. The immunogenic conjugate of claim 11, wherein at least one linkage between CRM197 and polysaccharide occurs at every 5 saccharide repeat units of the polysaccharide.

13. The immunogenic conjugate of claim 9, wherein the CRM197 comprises 5 to 23 lysines covalently linked to the polysaccharide.

14. The immunogenic conjugate of claim 13, wherein the CRM197 comprises 5 to 15 lysines covalently linked to the polysaccharide.

15. An immunogenic composition comprising the immunogenic conjugate of claim 1 and at least one of an adjuvant, diluent, or carrier.

16. A method of inducing an immune response against Staphylococcus aureus in a subject comprising administering to the subject an immunologically effective amount of the immunogenic composition of claim 15.

17. A method of reducing a Staphylococcal infection, disease or condition associated with a Staphylococcus bacteria in a subject, the method comprising the step of administering an immunologically effective amount of the immunogenic composition of claim 15 to the subject.

18. The immunogenic conjugate of claim 1, wherein the capsular polysaccharide is a serotype 5 or a serotype 8 capsular polysaccharide.

19. An immunogenic polysaccharide-protein conjugate comprising an isolated Staphylococcus aureus capsular polysaccharide conjugated to a carrier protein, wherein the polysaccharide has a molecular weight of between 70 kDa and 300 kDa, wherein the conjugate has a molecular weight range of between 1600 kDa and 3000 kDa, and wherein the conjugate comprises a one-carbon or zero-carbon linker between the polysaccharide and the carrier protein.

20. The immunogenic conjugate of claim 13, wherein the CRM197 comprises 18 to 22 lysines covalently linked to the polysaccharide.

21. The immunogenic conjugate of claim 1, wherein the conjugate has a molecular weight range of between 1533 kDa and 2656 kDa.

22. The immunogenic conjugate of claim 1, wherein the conjugate has a molecular weight range of between about 1300 kDa and about 2600 kDa.

23. The method of claim 17, wherein the infection, disease or condition is selected from the group consisting of invasive *Staphylococcus aureus* disease, sepsis and carriage.

24. The method of claim 17, wherein the method comprises the step of administering the immunologically effective amount of the immunogenic composition to the subject prior to a surgical procedure.

25. The immunogenic composition of claim 15, wherein the capsular polysaccharide is a serotype 5 or a serotype 8 capsular polysaccharide.

26. The immunogenic composition of claim 25, wherein the composition comprises less than 30% free serotype 5 or serotype 8 polysaccharide compared to the total amount of serotype 5 or serotype 8 polysaccharide.

27. The immunogenic composition of claim 26, wherein the composition comprises less than 20% free serotype 5 or serotype 8 polysaccharide compared to the total amount of serotype 5 or serotype 8 polysaccharide.

* * * * *